US012661479B2

(12) United States Patent
Labbé

(10) Patent No.: US 12,661,479 B2
(45) Date of Patent: Jun. 23, 2026

(54) METHOD, SYSTEM, AND MEDIUM FOR AFFECTIVE MUSIC RECOMMENDATION AND COMPOSITION

(71) Applicant: LUCID INC., Toronto (CA)

(72) Inventor: Aaron Labbé, Toronto (CA)

(73) Assignee: Lucid Inc., Toronto (CA)

( * ) Notice: Subject to any disclaimer, the term of this patent is extended or adjusted under 35 U.S.C. 154(b) by 975 days.

(21) Appl. No.: 17/801,587

(22) PCT Filed: Feb. 24, 2021

(86) PCT No.: PCT/CA2021/050220
§ 371 (c)(1),
(2) Date: Aug. 23, 2022

(87) PCT Pub. No.: WO2021/168563
PCT Pub. Date: Sep. 2, 2021

(65) Prior Publication Data
US 2023/0113072 A1      Apr. 13, 2023

Related U.S. Application Data

(60) Provisional application No. 63/144,307, filed on Feb. 1, 2021, provisional application No. 63/074,109, filed
(Continued)

(51) Int. Cl.
*A61M 21/02*       (2006.01)
*A61M 21/00*       (2006.01)
(Continued)

(52) U.S. Cl.
CPC .............. *A61M 21/02* (2013.01); *G10G 1/00* (2013.01); *G10H 1/0025* (2013.01);
(Continued)

(58) Field of Classification Search
CPC ..... A61M 21/00–02; A61B 5/165–167; G10H 1/0025; G10H 2210/111–121;
(Continued)

(56) References Cited

U.S. PATENT DOCUMENTS

2006/0143647 A1      6/2006   Bill
2010/0145892 A1      6/2010   Yang et al.
(Continued)

FOREIGN PATENT DOCUMENTS

AU         2021228385          9/2022
CA          3169171            9/2021
(Continued)

OTHER PUBLICATIONS

"European Application Serial No. 21761481.7, Response filed Feb. 23, 2024 to Communication Pursuant to Article 94(3) EPC mailed Nov. 24, 2023", 115 pgs.
(Continued)

*Primary Examiner* — Thaddeus B Cox
(74) *Attorney, Agent, or Firm* — Schwegman Lundberg & Woessner, P.A.

(57)                ABSTRACT

A method, system, and medium for affective music recommendation and composition. A listener's current affective state and target affective state are identified, and an audio stream, such as a music playlist, is generated with the intent of effecting a controlled trajectory of the listener's affective state from the current state to the target state. The audio stream is generated by a machine learning system trained using data from the listener and/or other users indicating the effectiveness of specific audio segments, or audio segments having specific features, in effecting the desired affective trajectory. The audio stream is presented to the user as an auditory stimulus. The machine learning system may be updated based on the affective state changes induced in the
(Continued)

listener after exposure to the auditory stimulus. The machine learning system may also be used to compose, master, and/or adapt music configured to induce specific affective responses in listeners.

18 Claims, 38 Drawing Sheets

Related U.S. Application Data on Sep. 3, 2020, provisional application No. 63/073, 252, filed on Sep. 1, 2020, provisional application No. 62/980,979, filed on Feb. 24, 2020.

(51) Int. Cl.
*G10G 1/00* (2006.01)
*G10H 1/00* (2006.01)

(52) U.S. Cl.
CPC .............. *A61M 2021/0027* (2013.01); *A61M 2205/3303* (2013.01); *G10H 2210/111* (2013.01); *G10H 2210/125* (2013.01); *G10H 2220/116* (2013.01); *G10H 2240/085* (2013.01); *G10H 2240/131* (2013.01); *G10H 2250/311* (2013.01)

(58) Field of Classification Search
CPC .......... G10H 2210/145; G10H 2240/081–085; G16H 20/70
See application file for complete search history.

(56) References Cited

U.S. PATENT DOCUMENTS

| | | | |
|---|---|---|---|
| 2012/0233164 A1 | 9/2012 | Rowe et al. | |
| 2014/0052731 A1 | 2/2014 | Dahule et al. | |
| 2015/0242679 A1 | 8/2015 | Naveh | |
| 2015/0297109 A1 | 10/2015 | Garten et al. | |
| 2021/0168450 A1* | 6/2021 | Gritzman | ........... H04N 21/4668 |

FOREIGN PATENT DOCUMENTS

| | | |
|---|---|---|
| CN | 110795944 | 2/2020 |
| CN | 115428070 | 12/2022 |
| EP | 4111448 | 12/2023 |
| JP | 2014526057 A | 10/2014 |
| JP | 2018504719 A | 2/2018 |
| JP | 2019121401 A | 7/2019 |
| JP | 7740716 B2 | 9/2025 |
| KR | 20220146528 | 11/2022 |
| WO | 2021168563 | 9/2021 |

OTHER PUBLICATIONS

"Canadian Application Serial No. 3,169,171, Office Action mailed Jul. 29, 2024", 4 pgs.
European Application Serial No. 21761481.7, Communication Pursuant to Article 94(3) EPC mailed Sep. 2, 2025, 9 pgs.
Indian Application Serial No. 202217054043, Response filed Aug. 20, 2025 to First Examination Report mailed Mar. 25, 2025, w/ English claims, 20 pgs.

Japanese Application Serial No. 2022-550664, Notification of Reasons for Rejection mailed Apr. 30, 2025, W/English Translation, 8 pgs.
Japanese Application Serial No. 2022-550664, Response filed Jul. 22, 2025 to Notification of Reasons for Rejection mailed Apr. 30, 2025, w/ English claims, 11 pgs.
Yang et al. "Midinet: A Convolutional Generative Adversarial Network for Symbolic-Domain Music Generation", arXiv: 1703.10847v2 Jul. 18, 2017.
H. Chen , Q. Xiao and X. Yin, "Generating Music Algorithm with Deep Convolutional Generative Adversarial Networks", IEEE 2nd International Conference on Electronic Technology (ICET) 2019.
H. Liu and Y. Yang, "Lead Sheet Generational and Arrangement by Conditional Generative Adversarial Network", 2018 17th IEEE International Conference on Machine Learning and Applications (ICMLA), 2018.
Li et al., "Automatic Melody Composition Using Enhanced GAN", Mathematics, 7(10:883 Sep. 23, 2019.
"European Application Serial No. 21761481.7, Communication Pursuant to Article 94(3) EPC mailed Nov. 24, 2023", 20 pgs.
"Canadian Application Serial No. 3,169,171, Response filed Feb. 5, 2024 to Examiners Rule 86(2) Report mailed Oct. 16, 2023", 224 pgs.
"Korean Application Serial No. 10-2022-7032538, Voluntary Amendment filed Dec. 5, 2023", w English claims, 15 pgs.
"Canadian Application Serial No. 3,169,171, Response Filed Nov. 7, 2024 to Office Action mailed Jul. 29, 2024", w Amended Claims, 21 pgs.
"Israel Application Serial No. 295812, Notification of Defects in Patent Application mailed Feb. 23, 2025", W English Translation, 12 pgs.
"Indian Application Serial No. 202217054043, First Examination Report mailed Mar. 25, 2025", w English Translation, 8 pgs.
"International Application Serial No. PCT CA2021 050220, International Search Report mailed May 10, 2021", 4 pgs.
"International Application Serial No. PCT CA2021 050220, Written Opinion mailed May 10, 2021", 7 pgs.
"International Application Serial No. PCT CA2021 050220, International Preliminary Report on Patentability mailed Sep. 9, 2022", 9 pgs.
"Israel Application Serial No. 295812, Notification Prior to Examination mailed Mar. 26, 2023", with machine translation, 4 pgs.
"Mexican Application Serial No. MX a 2022 010358, Office Action mailed Sep. 2, 2022", with machine translation, 5 pgs.
"Mexican Application Serial No. MX a 2022 010358, Office Action mailed Nov. 11, 2022", with machine translation, 5 pgs.
"European Application Serial No. 21761481.7, Partial Supplementary European Search Report mailed Aug. 11, 2023", 26 pgs.
"Canadian Application Serial No. 3,169,171, Examiners Rule 86(2) Report mailed Oct. 16, 2023", 4 pgs.
Ogino, "Music Playlist Generation System for Changing a Listener's Mood to a Positive State", International Symposium on Affective Science and Engineering ISASE2019, (2019), 1-4 pgs.
"Indian Application Serial No. 202217054043, Hearing Notice mailed Dec. 19, 2025", 3 pgs.
"Indian Application Serial No. 202217054043, Hearing Notice mailed Jan. 6, 2026", 3 pgs.
"Israeli Application Serial No. 295812, Office Action mailed Jan. 8, 2026", 8 pgs.
"Australian Application Serial No. 2021228385, First Examination Report mailed Jan. 7, 2026", 5 pgs.
"Korean Application Serial No. 10-2022-7032538, Notification of Reasons for Rejection mailed Jan. 21, 2026", W English Translation, 14 pgs.

\* cited by examiner

1700c

Composition Lead Sheet Process
2300

MIR blueprint
1730

Data Transform
2302

Composition
Lead Sheet
2400

METHOD, SYSTEM, AND MEDIUM FOR AFFECTIVE MUSIC RECOMMENDATION AND COMPOSITION

FIELD

At least some example embodiments relate to music recommendation and music composition systems, and in particular to systems for composing and recommending music intended to induce specific changes in a listener's affective state.

BACKGROUND

Affect is a concept used in psychology to describe the experience of emotion, mood, or feeling. Humans experience different affective states under different conditions. External stimuli can affect a person's mood or affect.

Many people have a particularly acute affective response to various kinds of musical stimuli. Music plays a sizable role in human culture in large part because of its effectiveness in inducing specific affective state in listeners. Individual listeners commonly select music to listen to based on a desire to maintain or achieve a target affective state, for example, energized, relaxed, melancholy, nostalgic, happy, or aggressive.

Music recommendation systems attempt to recommend music to a listener based on an inference of what the listener may prefer. These inferences are typically based on data gathered from the listener. The data may be gathered through interaction with the listener at the time of the recommendation or during a prior interaction indicating overall listener preferences. A recommendation system may present the listener with a set of themes and recommend music based on the listener's selected theme(s). These themes can be organized on any of a number of principles, including genre (classical, country, rap), season or setting (Christmas music, beach music), or historical period (1960s, 1980s, contemporary). Some themes may be organized around mood or other affective state information, such as music intended to induce or align with a listener's affective state (sad, happy, relaxing, energizing). Themes may also be organized around an activity that implies the targeting of certain affective states (calm music for cooking or meditating, aggressive music for working out, upbeat rhythmic music for dancing).

Some music recommendation systems also infer listener preferences through data relating the listener to specific musical compositions. The system may, for example, gather data on prior musical listening selections by the listener or prior purchases of musical recordings by the listener. These selection or purchases may be cross-referenced with other available musical compositions, such as by identifying compositions having similar characteristics to those preferred by the listener. Some systems may use collaborative filtering to identify compositions preferred by other users with similar tastes, or similar selection or purchase histories, to the listener. Some systems may gather feedback from the listener in relation to the system's recommendations and update their model of the user's preferences and their confidence in their inferences accordingly.

Systems that include affect-related themes typically identify musical compositions matching a given theme based on overall characteristics of the compositions that are not specific to an individual listener. Affect-related characteristics of a musical composition are typically identified with respect of the composition as a whole. Trained experts in musical classification are typically employed to listen to and characterize musical compositions according to a process called music information retrieval (MIR). MIR involves extracting and representing features of the music. Standards for the representation of MIR features have been promulgated by the Institute for Research and Coordination in Acoustics/Music (IRCAM), and software exists to assist with MIR, such as the MIRtoolbox software package for Matlab. Some existing collections of MIR data include affect-related tags or features associated with specific musical compositions, based on the evaluation of the affect-related features of a composition as a whole by an expert listener.

Music composition is not typically assisted by a sophisticated formal model of human affect in relation to musical elements. Music intended to achieve specific affective state changes in a listener is generally composed by human composers based on subjective criteria held by the composer.

SUMMARY

The present disclosure describes example devices, methods, systems, and non-transitory media for affective music recommendation and composition. In some embodiments, a listener's current affective state and target affective state are identified, and an audio stream (such as a music playlist, sound design or an algorithmically composed piece of music) is generated with the intent of effecting a controlled trajectory of the listener's affective state from the current state to the target state. The audio stream is generated by a machine learning model trained using data from the listener and/or other users indicating the effectiveness of specific audio segments, or audio segments having specific features, in effecting the desired affective trajectory. In some embodiments, a song may be composed to achieve a particular target affective state or a particular affective trajectory based on a model of how a particular listener, or a population of listeners, respond affectively to particular musical elements.

Example embodiments are directed to a method for generating an audio stream for inducing an affective state change in a listener. The method comprises the steps of identifying the listener's current affective state, identifying the listener's target affective state, identifying an affective trajectory from the current affective state to the target affective state, using a trained segment identification machine learning model to identify a first audio segment likely to induce in the listener a desired affective response corresponding to at least an initial portion of the affective trajectory when the first audio segment is presented to the listener as an auditory stimulus, generating the audio stream based at least in part on the first audio segment, and sending audio stream data based on the audio stream to a listener device.

A second embodiment is directed to a system for generating an audio stream for inducing an affective state change in a listener. The system comprises a processor system, a communication system, and a memory system. The memory system has stored thereon an executable trained segment identification machine learning model, and executable instructions. When executed by the processor system, the executable instructions cause the system to identify the listener's current affective state based on listener state data received by the communication system, identify the listener's target affective state based on target affective state data received by the communication system, identify an affective trajectory from the current affective state to the target affective state, execute the trained segment identification machine learning model to identify a first audio segment likely to induce in the listener a desired affective response corresponding to at least an initial portion of the affective trajectory in the listener when presented to the listener as an auditory stimulus, generate the audio stream based at least in part on the first audio segment, and use the communication system to send audio stream data based on the audio stream to a listener device.

According to a further aspect which can be combined with other embodiments disclosed herein, after using the trained segment identification machine learning model to identify the first audio segment, an affective inference process is used to infer an inferred new affective state based on the current affective state and a set of audio feature values of the first audio segment. An updated affective trajectory from the inferred new affective state data to the target affective state is identified. The trained segment identification machine learning model is used to identify a subsequent audio segment likely to induce in the listener a subsequent desired affective response corresponding to at least an initial portion of the updated affective trajectory when the subsequent audio segment is presented to the listener as an auditory stimulus. The audio stream is generated based at least in part on the first audio segment and the subsequent audio segment.

According to a further aspect which can be combined with other embodiments disclosed herein, the trained segment identification machine learning model is trained using reward data received from the affective inference process, and the affective inference process generates the reward data by inferring an inferred affective response of the listener to a set of audio feature values of the audio stream, and generating the reward data based on a comparison of the inferred affective response to the desired affective response.

According to a further aspect which can be combined with other embodiments disclosed herein, the affective inference process comprises a trained affect inference machine learning model, and the trained affect inference machine learning model is trained using training data comprising training audio feature data corresponding to a plurality of training audio segments, and affective state data gathered from one or more human subjects in association with exposure of each human subject to each of a plurality of audio stimuli corresponding to the plurality of training audio segments.

According to a further aspect which can be combined with other embodiments disclosed herein, the one or more human subjects comprises the listener.

According to a further aspect which can be combined with other embodiments disclosed herein, the trained segment identification machine learning model comprises a reinforcement learning model.

According to a further aspect which can be combined with other embodiments disclosed herein, the trained segment identification machine learning model comprises a deep learning neural network.

According to a further aspect which can be combined with other embodiments disclosed herein, the audio stream data comprises recommendation data recommending the audio stream.

According to a further aspect which can be combined with other embodiments disclosed herein, the audio stream data comprises the audio stream.

According to a further aspect which can be combined with other embodiments disclosed herein, after sending the audio stream data to the listener device updated current affective state data is received from the listener. The trained affect inference machine learning model using runtime training data comprising audio feature data corresponding to each of the first audio segment and the plurality of subsequent audio segments, and the updated current affective state data.

According to a further aspect which can be combined with other embodiments disclosed herein, identifying the listener's target affective state comprises receiving target affective state data from the listener via the listener device, and identifying the listener's target affective state based on the target affective state data.

According to a further aspect which can be combined with other embodiments disclosed herein, identifying the listener's current affective state comprises receiving affective self-evaluation data from the listener via the listener device, and identifying the listener's current affective state based on the affective self-evaluation data.

According to a further aspect which can be combined with other embodiments disclosed herein, identifying the listener's current affective state comprises receiving physiological data correlated with or more physiological states of the listener, and identifying the listener's current affective state based on the physiological data.

A further embodiment is directed to a non-transitory processor-readable medium containing instructions for executing one or more of the methods above.

A further embodiment is directed to a non-transitory storage medium containing the audio stream generated by one or more of the methods above.

A further embodiment is directed to a method for training a machine learning model to predict human affective responses to musical features, comprising: presenting a listener with music having a set of musical features; obtaining affective response data from the listener indicating the listener's affective response to presentation of the music; labelling the musical features of the music with the affective response data to generate labelled musical feature data; and using the labelled musical feature data as training data to train the machine learning model to predict the affective response data based on the musical feature data.

A further embodiment is directed to a system for predicting human response to music, comprising: a processor system; and a memory system having stored thereon: a machine learning model trained according to one of the methods described above.

According to a further aspect which can be combined with other embodiments disclosed herein, the machine learning model is a generative model for: receiving desired affective response data indicating a desired affective response; and generating music having musical features predicted by the machine learning model to induce the desired affective response in a listener.

According to a further aspect which can be combined with other embodiments disclosed herein, generating the music comprises: using the generative model to process the desired affective response data to generate musical feature data indicating the musical features; and generating the music based on the musical feature data.

According to a further aspect which can be combined with other embodiments disclosed herein, the musical feature data is music information retrieval (MIR) data.

According to a further aspect which can be combined with other embodiments disclosed herein, the MIR data is a MIR blueprint for the music.

According to a further aspect which can be combined with other embodiments disclosed herein, the generative model is a generative adversarial network (GAN).

According to a further aspect which can be combined with other embodiments disclosed herein, the GAN comprises a generator network, a probability network, and a control network.

According to a further aspect which can be combined with other embodiments disclosed herein, the GAN comprises a conditional GAN.

According to a further aspect which can be combined with other embodiments disclosed herein, the generator network comprises a generator neural network.

According to a further aspect which can be combined with other embodiments disclosed herein, the probability network comprises a discriminator neural network.

According to a further aspect which can be combined with other embodiments disclosed herein, the generator neural network and discriminator neural network each comprise a recurrent neural network (RNN) with long short-term memory (LSTM).

According to a further aspect which can be combined with other embodiments disclosed herein, generating the music based on the musical feature data comprises: generating a score based on the musical feature data; and generating the music based on the score.

According to a further aspect which can be combined with other embodiments disclosed herein, the score is a musical instrument digital interface (MIDI) score.

According to a further aspect which can be combined with other embodiments disclosed herein, generating the score comprises: receiving composition intention information; and generating the score based on the musical feature data and the composition intention information.

According to a further aspect which can be combined with other embodiments disclosed herein, the composition intention information comprises one or more of: score type information, instrumentation information, and score length information.

According to a further aspect which can be combined with other embodiments disclosed herein, the composition intention information is indicated by composition intention user input received from a user.

According to a further aspect which can be combined with other embodiments disclosed herein, the memory further stores a score generation machine learning model; and generating the score comprises using the score generation machine learning model to process the musical feature data to generate the score.

According to a further aspect which can be combined with other embodiments disclosed herein, the score generation machine learning model is a score generation generative adversarial network (GAN).

According to a further aspect which can be combined with other embodiments disclosed herein, the score generation GAN comprises a generator network, a probability network, and a control network.

According to a further aspect which can be combined with other embodiments disclosed herein, the score generation GAN comprises a conditional GAN.

According to a further aspect which can be combined with other embodiments disclosed herein, the generator network comprises a generator neural network.

According to a further aspect which can be combined with other embodiments disclosed herein, the probability network comprises a discriminator neural network.

According to a further aspect which can be combined with other embodiments disclosed herein, the generator neural network and discriminator neural network each comprise a recurrent neural network (RNN) with long short-term memory (LSTM).

According to a further aspect which can be combined with other embodiments disclosed herein, generating the music based on the score comprises: presenting the score to a user; receiving rough mix user input from the user; generating a rough mix based on the rough mix user input; and generating the music based on the rough mix.

According to a further aspect which can be combined with other embodiments disclosed herein, generating the music based on the score further comprises: generating a composition lead sheet based on the musical feature data; and presenting the composition lead sheet to the user.

According to a further aspect which can be combined with other embodiments disclosed herein, generating the music based on the rough mix comprises: generating a production lead sheet based on the musical feature data and the rough mix; presenting the composition lead sheet to the user; receiving final mix user input from the user; generating a final mix based on the final mix user input; and generating the music based on the final mix.

According to a further aspect which can be combined with other embodiments disclosed herein, the memory further stores a mastering machine learning model; and generating the final mix comprises using the mastering machine learning model to process the musical feature data and the final mix to generate the music.

According to a further aspect which can be combined with other embodiments disclosed herein, the mastering machine learning model is further configured to: receive an existing piece of music; and process the musical feature data and the existing piece of music to generate the music having the musical features.

According to a further aspect which can be combined with other embodiments disclosed herein, the mastering machine learning model is further configured to generate the music having the musical features based on a plurality of existing musical stems.

According to a further aspect which can be combined with other embodiments disclosed herein, the mastering machine learning model comprises a recurrent deep Q network (DQN).

According to a further aspect which can be combined with other embodiments disclosed herein, the mastering machine learning model comprises a branching recurrent DQN.

According to a further aspect which can be combined with other embodiments disclosed herein, the mastering machine learning model includes a long short term memory (LSTM).

A further embodiment is directed to a non-transitory storage medium containing the audio stream generated by the system described above.

According to a further aspect which can be combined with other embodiments disclosed herein, the machine learning model is further configured to: receive a plurality of existing pieces of music; receive the desired affective response data; and identify an existing piece of music of the plurality of existing pieces of music likely to induce the desired affective response in a listener.

BRIEF DESCRIPTION OF THE DRAWINGS

Embodiments will now be described by way of examples with reference to the accompanying drawings, in which like reference numerals may be used to indicate similar features.

DETAILED DESCRIPTION OF EXAMPLE EMBODIMENTS

Example embodiments will now be described with respect to methods, systems, and non-transitory media for affective music recommendation and composition. Music recommendation systems will be described first, with reference to FIGS. 1-15; the components of these music recommendation system will then be referred to in describing music composition systems with reference to FIGS. 16-30.

The described music recommendation systems and methods generate an audio stream for inducing an affective state change in a listener. Some embodiments leverage two separate machine learning models to generate audio streams, such as music playlists, likely to induce a desired affective response in the listener. One machine learning model is an affective inference model that estimates affective responses to a set of audio feature values of an audio segment, such as MIR feature values of a musical segment. The other machine learning system is a reinforcement learning model with a deep learning neural network—also called a Deep Q Network (DQN)—that is trained to estimate affective responses to audio segments using a set of audio segments (such as songs, or epochs excerpted from songs) and using feedback from the affective inference model based on the audio feature values (e.g. MIR feature values) of the audio segment.

A first example embodiment of an affective music recommendation system 100 for generating an audio stream for inducing an affective state change in a listener will now be described with reference to FIG. 1.

Figure 1:
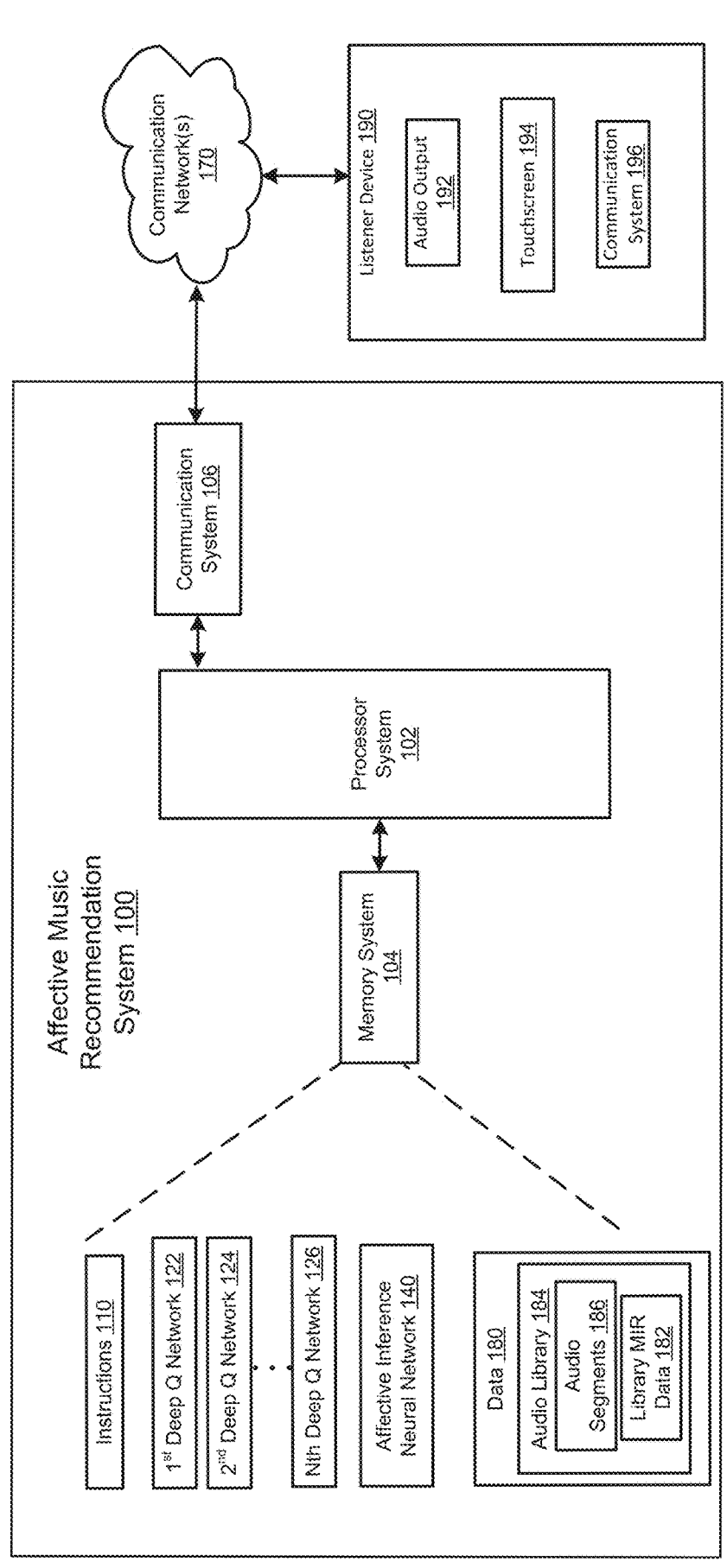
FIG. 1 is a block diagram of an example system for affective music recommendation according to example embodiments described herein.

FIG. 1 shows an affective music recommendation system 100 including a processor system 102 for executing computer program instructions, a memory system 104 for storing executable instructions and data, and a communication system 106 for communicating data with other devices or components.

The affective music recommendation system 100 may be implemented on one or more computer systems. It may be embodied by a single computer, multiple computers, a virtual machine, a distributed computing or cloud computing platform, or any other platform of platforms capable of carrying out the method steps described herein. In some embodiments, the affective music recommendation system 100 may encompass one or more electronic devices used by listeners (listener devices 190), while in other embodiments the affective music recommendation system 100 is in communication with such devices, directly or indirectly (e.g. via a communication network 170) using the communication system 106.

The processor system 102 may be embodied as any processing resource capable of executing computer program instructions, such as one or more processors on a computer or computing platform(s). The memory system 104 may be embodied as any data storage resource, such as one or more disk drives, random access memory, or volatile or non-volatile memory on one or more computing platforms. The communication system 106 may be embodied as one or more communication links or interfaces, including wired or wireless communication interfaces such as Ethernet, Wifi, or Bluetooth interfaces. In some embodiments, one or more of the listener devices 190 may be implemented on the same platform as the affective music recommendation system 100; in such embodiments, the communication system 106 may comprise an internal communication bus or other intra-platform data transfer system.

The memory system 104 may have stored thereon several types of computer programs in the form of executable instructions. There may be stored thereon a set of executable instructions 110 for carrying out the method steps described herein. There may also be one or more machine learning models for identifying audio segments intended to induce a specific affective response in a listener, shown here as a plurality of deep Q networks (also called deep learning neural networks): first deep Q network 122, second deep Q network 124, and so on through an Nth deep Q network 126. The memory system 104 may also have stored thereon an affective inference machine learning model for inferring affective states induced by exposure of a listener to an audio segment having a particular set of audio feature values, shown here as an affective inference neural network 140. These machine learning models may be deployed on the affective music recommendation system 100 after being trained as further described below.

The memory system 104 may have stored thereon several types of data 180. The data 180 may include data pertaining to previous records of experiences with the affective recommendation system 100 (affective data, and segment selections for instance). The data 180 may also include an audio library 184, comprising a plurality of audio segments 186 and audio feature data corresponding to each of the plurality of audio segments 186. The audio segments 186 may comprise digital audio data stored as individual audio clips, or they may be extracts from audio clips stored in the audio library 184, such as epochs of fixed duration extracted from songs of variable durations. The audio feature data is shown here as library MIR data 182. It may include MIR metadata associated with each audio segment 186 indicating MIR features of the audio segment 186 with corresponding values. The audio feature data may also, in some embodiments, include non-MIR data or metadata.

The listener device 190 may be an electronic device operated by a listener or end user of the affective music recommendation system 100, such as a computer or smart phone in communication with the affective music recommendation system 100 via the communication network 170. The affective music recommendation system 100 may support multiple types of listener device 190. Some listener devices 190 include user interface components, such as a touchscreen 194 for displaying visual data and receiving user input and an audio output 192, such as speakers and/or a wired or wireless interface to headphones. Communication with the affective music recommendation system 100 is effected by a communication system 196, which may communicate via the communication network 170.

Figure 2A:
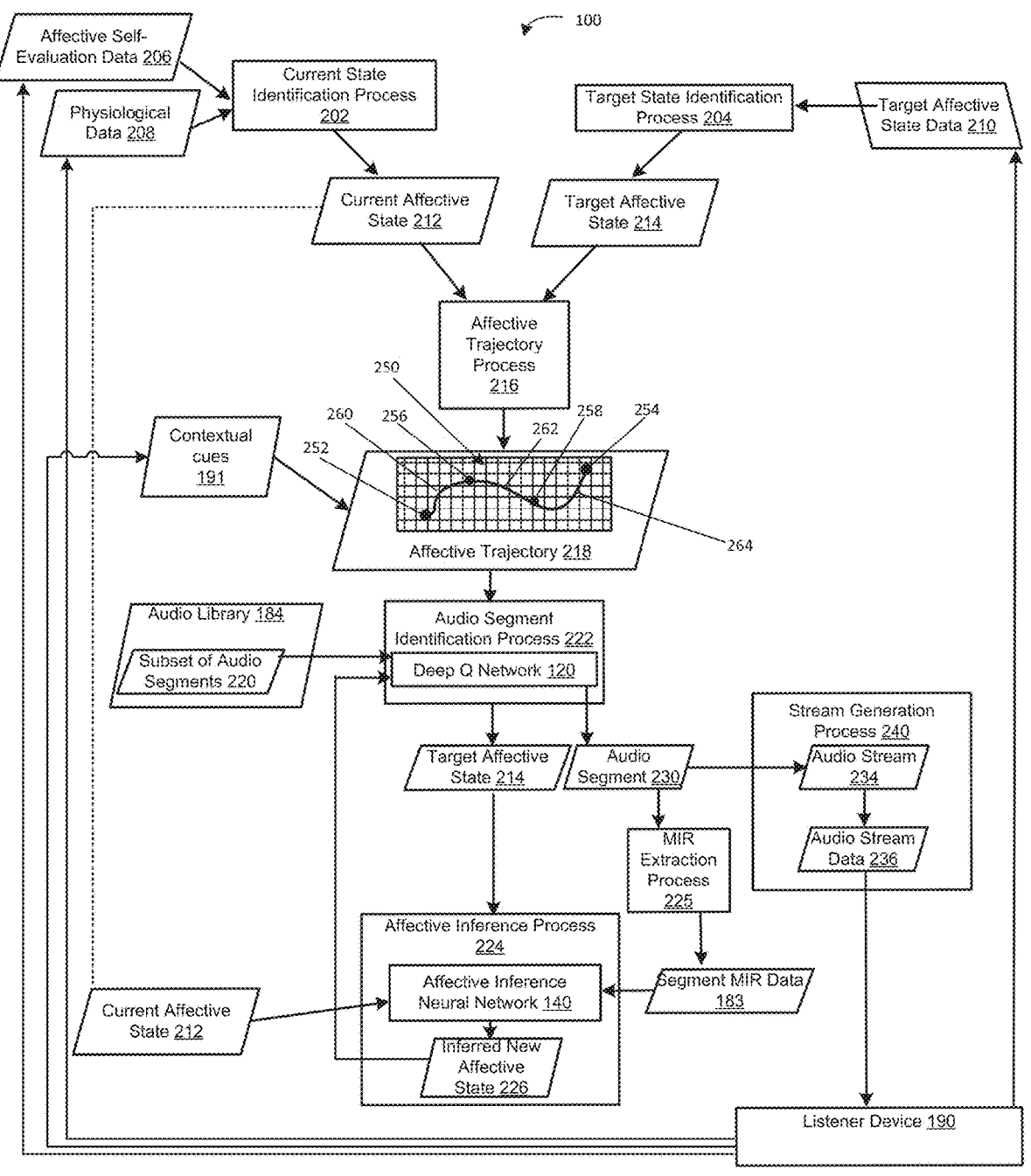
FIG. 2A is a system diagram of an example system for affective music recommendation operating in stream generation mode according to example embodiments described herein.

FIG. 2A shows a functional system diagram of the affective music recommendation system 100. Various functional steps are carried out by the affective music recommendation system 100 by using the processor system 102 to execute the executable instructions 110 stored in the memory system 104.

The affective music recommendation system 100 executes the instructions 110 to carry out methods for generating an audio stream 234 for inducing an affective state change in a listener. To carry out the method steps, the affective music recommendation system 100 uses a number of functional blocks implemented by execution of the instructions 110, the segment identification machine learning model (e.g. deep Q networks 122, 124 through 126), and the affective inference machine learning model (e.g. affective inference neural network 140). The affective music recommendation system 100 operates in two distinct modes: an audio stream generation mode, which typically takes place during a user session, and a training mode, which may take place in between user sessions. The operation of the affective music recommendation system 100 in the audio stream generation mode will be described first, with reference to FIG. 2A, followed by a description of the training mode with reference to FIG. 2B.

Listener state data relating to a listener are received via the communication system 106 and used at current state identification process 202 to identify the listener's current affective state 212. The listener state data may in various embodiments include affective self-evaluation data 206, physiological data 208, and/or other types of data potentially relevant to identifying the listener's affective state. The listener state data may be received from one or more sources, including from the listener device 190, from other devices, and/or from sources internal to the affective music recommendation system 100. Affective self-evaluation data 206 may be generated by the listener device 190 as described in further detail below. Physiological data 208 may be received from the listener device 190 or another device configured to gather physiological sensor data from the listener, as further described below. Other listener state data used to determine a listener's affective state may include camera data showing the listener's facial expressions or behavior, voice data indicating the listener's intonation or speech content, or any other data that may be used to assist in identifying a listener's affective state.

In the field of affective computing, there exist a number of known techniques for identifying human affective states using physiological, self-reported, and/or other data types, and for representing affective states in data. One common model for representation of affective states is a two-dimensional model of affect, sometimes called the circumplex model, where a given affective state is represented as a valence value (representing the degree of positive or negative emotion) and an arousal or activation value (representing the degree of emotional alertness or energy). In a two-dimensional valence-activation model of affect, for example, sadness might be represented by a negative valence and low activation, anger might be represented as negative valence and high activation, enthusiasm might be represented as positive valence and high activation, and relaxation might be represented as positive valence and low activation. Examples described herein will generally refer to a two-dimensional model of affect with valence and activation values. However, some embodiments may use other affect models, including models that use more or fewer than two dimensions to characterize affective states, models that use time-varying affective values to model affective states, and models that use a list of discrete affective states without using numerical values.

The current state identification process 202 may in some embodiments receive listener state data that explicitly identifies the listener's current affective state. In other embodiments, the current state identification process 202 may use an affect identification engine, such as a further machine learning model trained to identify affective states in a specific listener or in humans generally, to identify the listener's affective state based on the listener state data. Additional biomarkers inferred from physiological data can also be used as inputs to the current state identification process, even beyond the two-dimensional valence and activation values, such as anxiety level, focus levels, agitation levels, etc.

Some embodiments may receive listener state data at specific times during the operation of the affective music recommendation system 100, such as at the beginning of a user session and at the end of a user session. Other embodiments may receive listener state data continuously or at times determined by the timing of user input. For example, some embodiments may receive a constant stream of physiological data 208, and others may receive user-initiated affective self-evaluation data 206 at times dictated by the listener.

A target state identification process 204 is used to identify the listener's target affective state 214 based on target affective state data 210 received from a source such as the listener device 190. In some embodiments, the target affective state data 210 may be predetermined by the nature of the intended application: for example, a relaxation application may always provide target affective state data 210 indicating a low-activation, positive-valence state, whereas a concentration application may provide target affective state data

210 indicating a high-activation, positive-to-neutral valence state. Other embodiments may identify the listener's target affective state 214 based on listener preference data received from the listener device 190 before or during a user session.

In some embodiments, based on the current affective state 212 and target affective state 214, an affective trajectory process 216 identifies an affective trajectory 218 from the current affective state 212 to the target affective state 214. In embodiments employing a two-dimensional affect model, the affective trajectory 218 may be represented as a curve 250 in two dimensions. The example curve 250 is plotted in an example affect space defined, e.g., by valence in the horizontal dimension (left=negative, right=positive) and activation in the vertical dimension (active=up, passive=down). The current affective state 212 of the listener is plotted as a starting point 252 for the curve 250. The target affective state 214 is plotted as an endpoint 254 of the curve 250. One or more intermediate waypoints may be plotted along the curve 250, such as first waypoint 256 and second waypoint 258, indicating intermediate affective states on the affective trajectory 218. An initial portion 260 of the curve 250 is defined by the starting point 252 and first waypoint 256. A second subsequent portion 262 of the curve 250 is defined by the first waypoint 256 and the second waypoint 258. A third and final subsequent portion 264 of the curve 250 is defined by the second waypoint 258 and the endpoint 254. Machine learning techniques can also be implemented to learn the best trajectory for individuals using the system, making these trajectories dynamic based on previous success at achieving the user's target affective state. In other embodiments, this trajectory can be omitted in its entirety and the user's current affective state and target affective state can be the only drivers for a session. In embodiments where the affective trajectory process is used, the intent is to enforce a controlled affective state change over time through a moving target for the DQN.

An audio segment identification process 222 is used to select or identify an audio segment that, when presented to the listener as an auditory stimulus, is likely to induce at least the initial portion 260 of the affective trajectory 218 in the affective state of the listener. The audio segment 230 is identified using a trained segment identification machine learning model, shown as DQN 120, that selects the audio segment 230 from a subset of the audio segments 220 stored in the audio library 184. The audio segment 230 is selected based on an assessment by the DQN 120 that the audio segment 230 is more likely than other audios segments in the subset of the audio segments 220 to induce at least the initial portion 260 of the affective trajectory 218 in the listener, i.e., that the audio segment 230, when played to the listener as an auditory stimulus, is likely to induce an affective state in the listener close to the state represented by the first waypoint 256 or one of the subsequent points 258, 254 on the affective trajectory 218.

The audio segment identification process 222 may also use as input contextual cues 191 received from the listener device 190, such as time of day, whether the listener is in a private environment, whether the listener is in a noisy environment, etc.

The DQN 120 used by the affective music recommendation system 100 may, under different circumstances, be any of the various DQNs from FIG. 1 (first DQN 122 through Nth DQN 126). In some embodiments, each of the plurality of DQNs 122, 124 through 126 is used to select from a different subset of the audio segments 220 from the audio library 184. These subsets of audio segments may be generated on various criteria: example subsets of audio segments may comprise songs selected based on preference data indicated by the listener, based on musical genre, or based on other grouping criteria. One purpose of the use of subsets instead of the entire audio library 184 may be to simplify the computation carried out by the DQN 120 by limiting the number of audio segments included in the subset of audio segments 220 to a maximum set size, such as 100 or 120 audio segments. Multiple DQNs (e.g. DQNs 122, 124 through 126) may be used as alternatives to each other in different user sessions to select audio segments from different audio segment subsets 220 depending on context.

In some embodiments, the DQN 120 may then identify one or more subsequent audio segments 230 likely to induce one or more subsequent desired affective responses corresponding to subsequent portions of the affective trajectory 218 (e.g. portions 262 and/or 264) in the listener when presented to the listener as auditory stimuli.

One iteration of the process of identifying an audio segment 230 may be referred to as one "step". After each step (i.e. after identifying the first audio segment, and after identifying each of the plurality of subsequent audio segments), a trained affect inference machine learning model (shown here as affective inference neural network 140) may be used to generate inferred new affective state data 226 and feed the inferred new affective state data 226 back to the DQN 120 in order to inform the decisions made by the DQN 120. This is carried out as part of an affective inference process 224, which receives the target affect data 214 and the audio segment 230 identified by the audio segment identification process 222 using the affective inference neural network 140 to infer an inferred new affective state 226 of the listener likely to result from exposure of the listener to an audio stimulus having audio features that match the audio features (e.g. the segment MIR data 183) of the audio segment 230.

In some embodiments, the affect inference process 224 may use a different technique to generate the inferred new affective state 226, such as a different machine learning or artificial intelligence model, or a set of predetermined correlations or rules.

Thus, the affective inference neural network 140 simulates the environment operated upon by, and providing feedback and reinforcement to, the DQN 120: namely, the affective inference neural network 140 simulates the affective responses of the listener, by inferring the likely affective responses of a user as determined by the prior training of the affective inference neural network 140 using audio feature data (e.g. segment MIR data 183) and one or more current affective states 212 of the listener. Training of example affective inference neural networks 140 is described in detail below.

It is also possible in some embodiments for the affective inference process 224 to be substituted fully, or in part, by a stream of real-time affective data measurement from an actual user. In these embodiments, the data stream is reliable enough to provide the necessary affective state data to inform the next "step" of the decision-making process made by DQN 120.

A stream generation process 240 generates an audio stream 234 based on the one or more audio segments 230 identified by the audio segment identification process 222. The audio stream may in some embodiments be a music playlist, which may be represented as a series of identifiers and/or other metadata corresponding to the one or more audio segments 230. The stream generation process 240 also generates audio stream data 236 for transmission to the listener device 190 over the communication system 106. In some embodiments, the audio stream data may include metadata corresponding to the one or more audio segments 230 included in the audio stream 234. This metadata may be sent to the listener device to allow the listener to review the proposed playlist and provide input via the touchscreen 194 to play or alter the playlist. In some embodiments, the audio stream data may include audio segment data corresponding to the one or more audio segments 230. The listener device may be configured to present this audio data to the listener as auditory stimuli via the audio output 192. The communications between the affective music recommendation system 100 and the listener device 190, including the transmission of different kinds of audio stream data 236 at different times and under different conditions, may in various embodiments include typical interactions between users and online music recommendation, curation, or playlist services.

The curve 250 of the affective trajectory 218 identified by the trajectory identification process 216 may have different characteristics in different embodiments and/or in different circumstances. Some embodiments may further include a process, such as a further machine learning model, for shaping the curve 250 to a user-dependent or user-independent shape based on affective feedback data collected over time. The curve 250 may be a simple linear trajectory (i.e. a straight ramp in two dimensions) from a first state to a second state, or it may be curved according to principles or patterns extracted from the scientific literature or affective data analysis. In embodiments that do not use an affective model using numerical values, the affective trajectory 218 may not be plotted in an affective space but may instead proceed through one or more intermediate affective states identified as being necessary intermediate affective states in transitioning from the current state to the target state.

The embodiments described herein are configured to induce one or more intermediate affective states (e.g. waypoints 256, 258) along the affective trajectory 218 before inducing the final target affective state 214. This approach to affective state alteration using musical stimuli follows the iso principle used in music therapy for mood management, which states that music should initially be matched to a listener's current mood and then gradually migrated toward a desired target mood over time. However, some embodiments may take different approaches to inducing affective responses, such as embodiments that attempt to induce an affective estate change using a single audio segment or embodiments that use a non-linear affective trajectory curve 250.

The description above provides an overview of the operation of the various functional blocks and data used by the affective music recommendation system 100 in audio stream generation mode. In training mode, the various functional blocks and data shown in FIG. 2A may be used for different purposes and may be supplemented by additional functional blocks and data, as described below with reference to FIG. 2B.

Figure 2B:
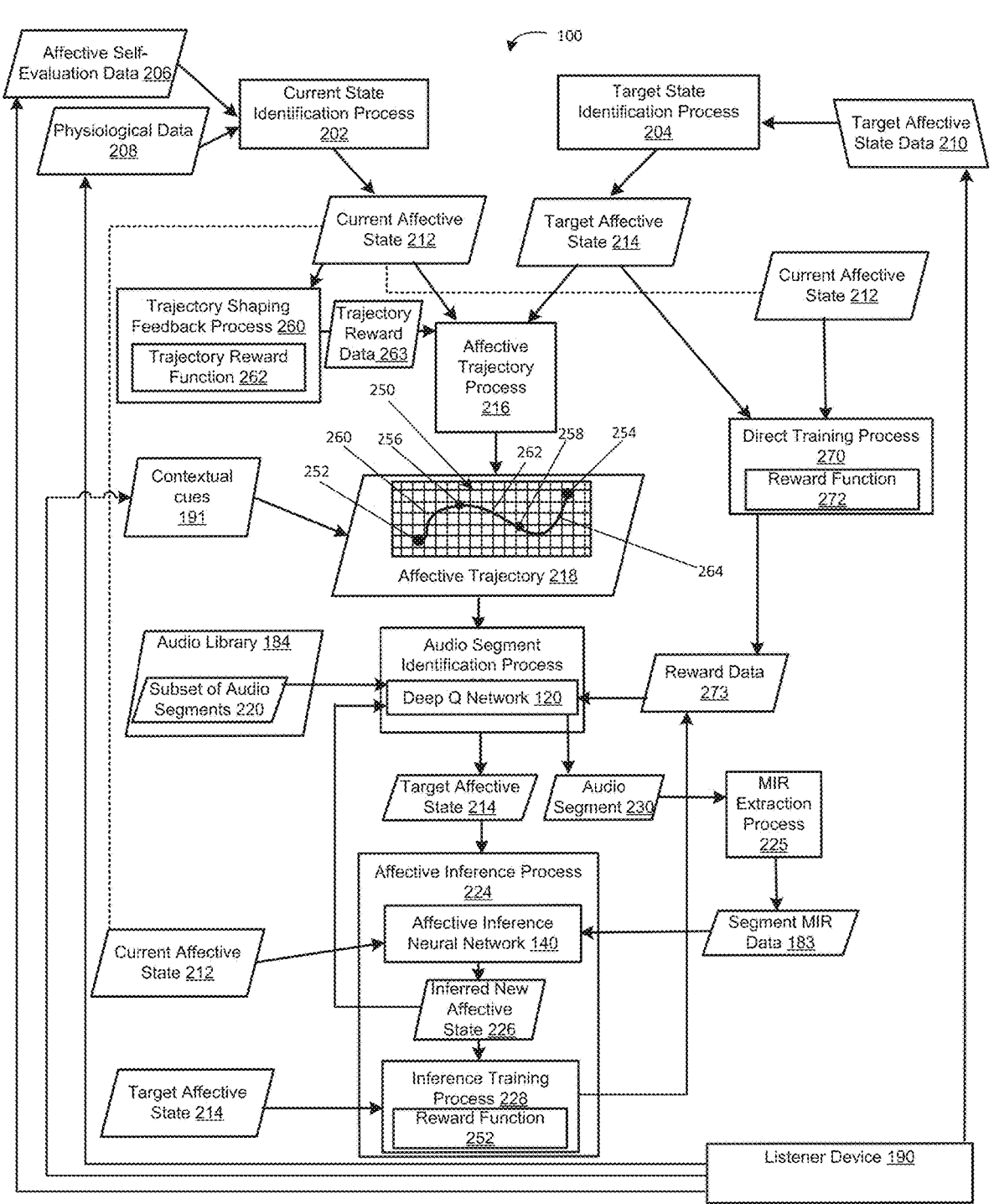
FIG. 2B is a system diagram of an example system for affective music recommendation operating in training mode according to example embodiments described herein.

FIG. 2B shows the affective music recommendation system 100 of FIG. 2A operating in training mode. For example, in training mode, the inferred new affective state 226 is compared to the target affective state 214 by an inference training process 228, which generates reward data 273 on the basis of this comparison. In some embodiments, the reward data 273 provides a positive reward to the DQN 120 if the inferred new affective state 226 is similar to the target affective state 214, but a negative reward if the inferred new affective state 226 is dissimilar to the target affective state 214.

In some embodiments, a reward function 272 may be used by the inference training process 228 to generate the reward data 273. The reward function 272 may vary over the course of a multiple sessions. In a direct training process 270, the reward function 272 receives affective self-evaluation data 206 and/or physiological data 208 from the listener device 190 at the end of a session (or after a user finishes listening to the audio stream 234), indicating a final affective state of the listener. The reward function 272 generates the reward data 273 based on a comparison between the listener's current affective state 212 at the end of the session (i.e. the listener's final affective state after listening to the audio segment 230) and the target affective state 214, either rewarding (i.e. positive reward) or punishing (i.e. negative reward) the DQN's 120 decisions throughout a session.

In some embodiments, the final affective state data includes all affective state data collected from the listener throughout a session and the current affective state data 212 collected from the listener at the end of or after a session. The reward data 273 is used to re-train the DQN 120 to make better decisions in future sessions, effectively personalizing the model. In other embodiments, an intermediate affective state target and long term affective state target may be set in order to reward actions taken at individual steps, as well as rewarding full sequences. Some embodiments may also use additional feedback data (not shown) collected from the listener device 190. Some embodiments may also discourage repeated selection of the same audio segment 230 by negatively rewarding a repeat selection, or may negatively reward selection of a particular audio segment if a user 'skips' that particular audio segment while listening to the audio stream 234.

In some embodiments, the final affective state data (i.e. the current affective state data 212 collected at the session end), correlated with the segment MIR data 183 of the audio segments played throughout a session, can also be used to re-train the affective inference neural network 140 to make better predictions in future sessions.

In some embodiments, the shape of the affective trajectory 218 may be adapted to a specific user by using a trajectory shaping machine learning model to implement the affective trajectory process 216. The final affective state data (i.e. the current affective state data 212 collected at the session end) and a trajectory reward function 252 can be used by a trajectory shaping feedback process 216 to shape the affective trajectory 218 based on successful outcomes from previous sessions. In embodiments where a trajectory shaping machine learning model is implemented to optimize the best affective trajectories for a particular user, the final affective state data and additional reward data 263 is used to train and optimize the model to personalize the trajectory based on the user.

In some embodiments, the affective trajectory 218 can be skipped entirely and the reward function 272 can generate reward data 273 by simply comparing the user's final affective state with the target affective state 214 and rewarding the full sequences predicted by DQN 120 accordingly.

In some embodiments, the DQN 120 may be replaced with any machine learning algorithm that learns through trial-and-error in the real world during an experience with a user (at runtime) and through a simulated environment (outside of runtime). This can be accomplished by any model-based or model-free reinforcement learning algorithm. All instances of functions of the DQN 120 described herein can be replaced in some embodiments with a different model-free or model-based reinforcement learning agent, including but not limited to approaches such as MBAC (model-based actor critic), A3C with advantage (model-free actor critic with advantage), Q-Learning, Deep Q Learning, and TDM (temporal difference models).

Figure 3:
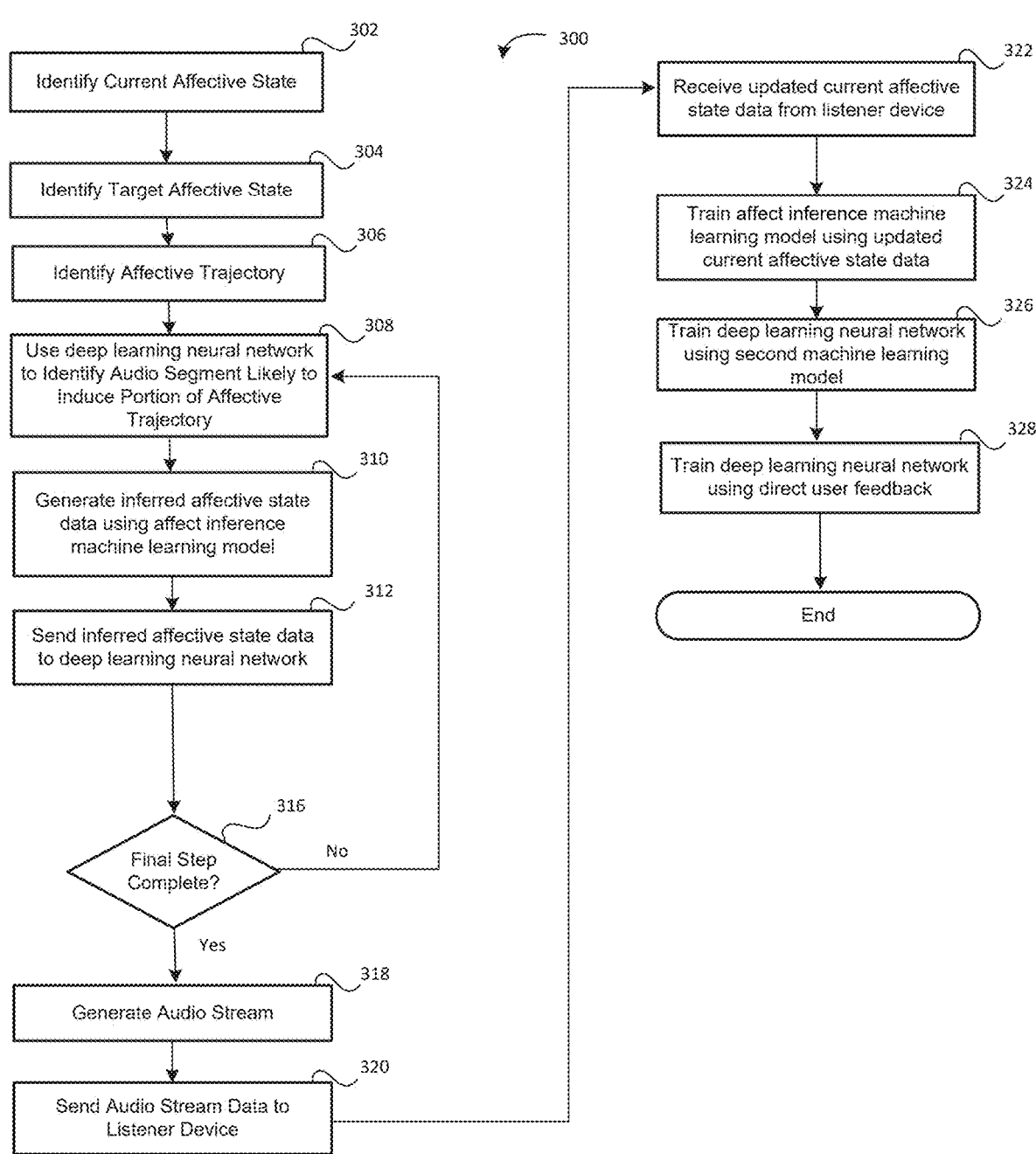
FIG. 3 is a flowchart of an example method for affective music recommendation according to example embodiments described herein.

FIG. 3 shows a flowchart for an example method 300 for generating an audio stream for inducing an affective state change in a listener. At step 302, the listener's current affective state 212 is identified, as described above. At step 304, the listener's target affective state 214 is identified, as described above. At step 306, the affective trajectory 218 is identified, as described above. At step 308, a trained segment identification machine learning model (e.g. DQN 120) is used to identify a first audio segment (e.g. audios segment 230) likely to induce in the listener a desired affective response corresponding to at least an initial portion (e.g. initial portion 260) of the affective trajectory 218 when the first audio segment is presented to the listener as an auditory stimulus, as described above.

At step 310, the affect inference process 224 uses the trained affect inference machine learning model 140 to predict how the audio segment selected by the deep learning neural network 120 at step 308 will affect the user. This inferred new affective state data 226 is generated by the affect inference machine learning model 140 at step 310 and sent to the DQN 120 as a state data input at step 312.

At step 316, the affective music recommendation system 100 may determine whether the method 300 has reached a final audio segment identification step out of a plurality of such steps, or whether one or more subsequent audio segments remain to be identified and added to the audio stream 234. In some embodiments, the audio stream may have a fixed length and/or require a fixed number of audio segment identification steps: the audio stream 234 may always be a first fixed duration (e.g., 240 seconds in duration), and each audio segment may be a second fixed duration (e.g., an 80-second epoch excerpted from a song), thereby requiring three audio segment identification steps to generate the audio stream 234. If the method 300 determines at step 316 that the final step has not been reached, subsequent audio segments likely to induce subsequent portions of the affective trajectory are identified as described above with reference to FIG. 2A. The method returns to step 308 to identify a subsequent audio segment and proceeds back to step 316 until the final step has been completed. The deep neural network at step 308 then uses the inferred affective state data 226 from the affective inference model 140 at step 310 as the 'current' affective state 212 for the next audio segment prediction.

Once the final step is completed, the audio stream 234 is generated at step 318, as described above. At step 320, the audio stream data 236 is generated and sent to the listener device 190 as described above. This completes the process of generating the audio stream and sending it to the listener for potential presentation as an auditory stimulus.

In some embodiments, the listener may be prompted or presented with the option to provide updated current affective state data after listening to all or part of the audio stream 234. This updated current affective state data may be used to train the affect inference machine learning model and improve its inferences with respect to the listener's likely affective response to the audio features of the audio segments making up the audio stream 234. This data can also be used to generate reward data 273 using the reward function 272 to reinforce the selections made by the DQN 120 at step 308 in the method outlined in FIG. 3.

At step 322, updated current affective state data is received, e.g. from the listener device 190 via the communication system 106. At step 324, the affect inference machine learning model (e.g. affective inference neural network 140) is trained using the updated current affective state data as described in detail below. This step typically concludes a user session.

In the embodiment described herein, the segment identification machine learning model (e.g. DQN 120) is also trained using one or both of an inference training process 224 and/or a direct training process 270. This training may take place at the end of a user session or during idle time when the listener is not using the system 100. At step 326, the segment identification machine learning model (e.g. DQN 120) is re-trained using the inference training process 228. The reward data 273 is generated by the reward function 272 based on the inferred new affective state 226 and the target affective state 214. This training step may reiterate the initial training of the DQN 120, as described in further detail below. This training can occur asynchronously and/or offline.

At step 328, the segment identification machine learning model (e.g. DQN 120) is re-trained using the direct training process 270. The reward data 273 is generated by the reward function 272 using the updated current affective state data 212 received from the listener through the listener device 190 at the end of the session. This training can also occur asynchronously and/or offline.

In some embodiments, it is possible to perform step 318 and 320 immediately after step 308, generating an audio stream after the first prediction made at 308. In these embodiments, a continuous stream of reliable current affective state data 212 is received from the user, avoiding the need for the inferred affective state data 226. In these embodiments, step 318 occurs after step 308, then step 320 and step 322 follow, returning to step 308 with the new affective state data 226 acquired through direct user feedback. This process could be repeated multiple times until an audio experience of a desired length is complete. In these embodiments, the training process of DQN 120 is done only using direct user feedback, removing the need for steps 310, 312, 324 and 326.

Figure 4A:
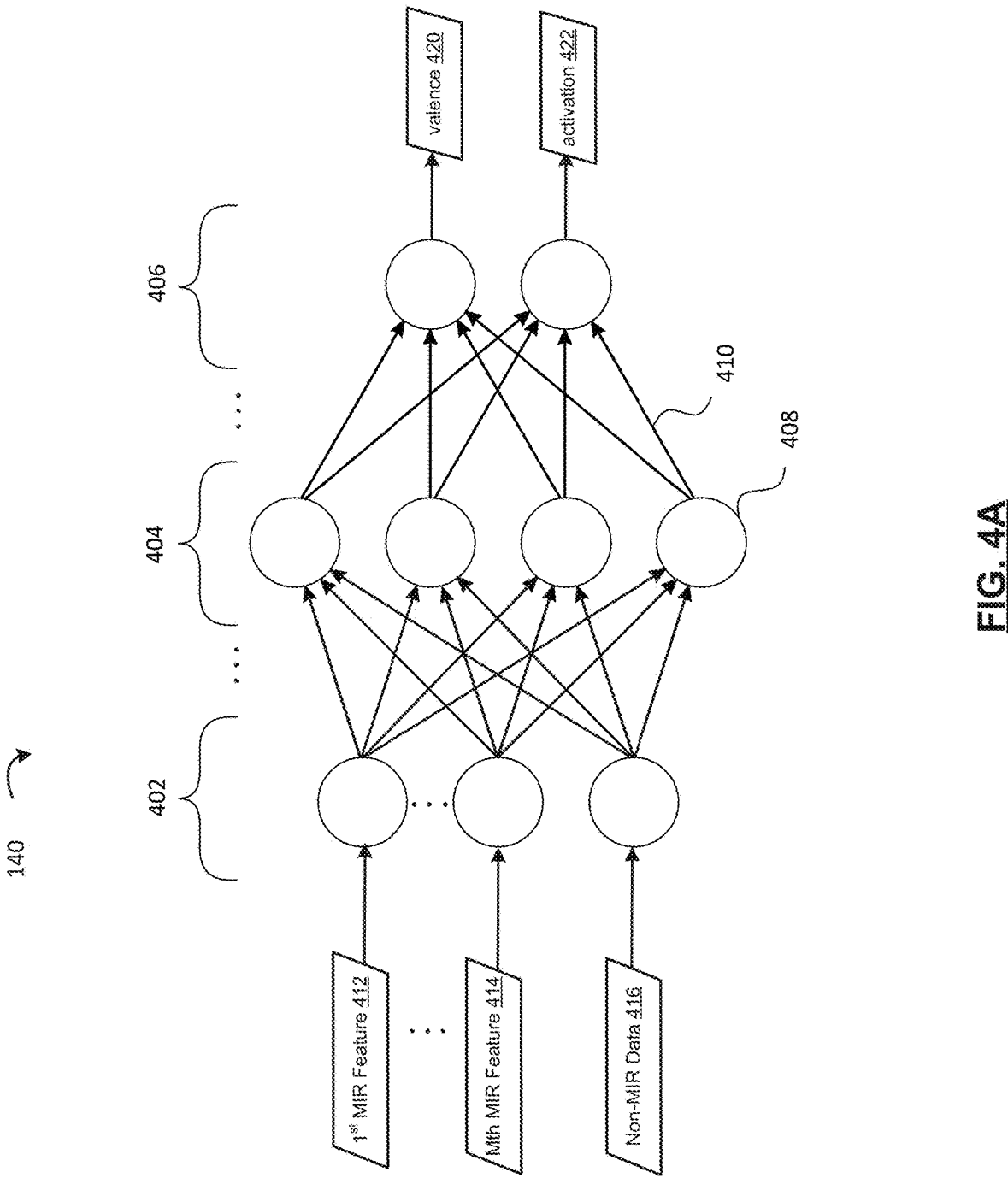
FIG. 4A is a schematic diagram showing a simplified neural network for affective state inference according to example embodiments described herein.
Figure 4B:
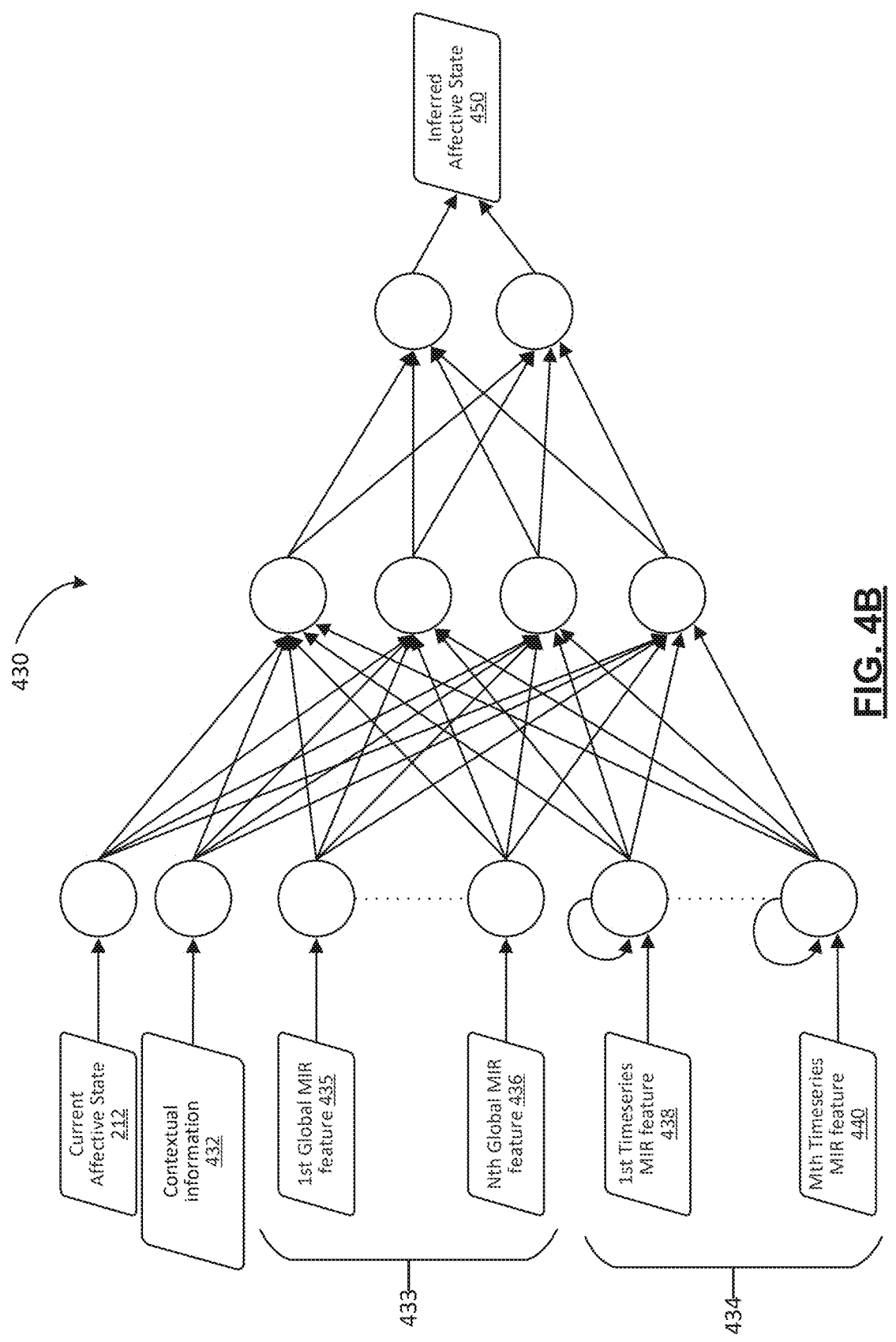
FIG. 4B is a schematic diagram showing a simplified recurrent neural network for affective state inference according to example embodiments described herein.
Figure 5:
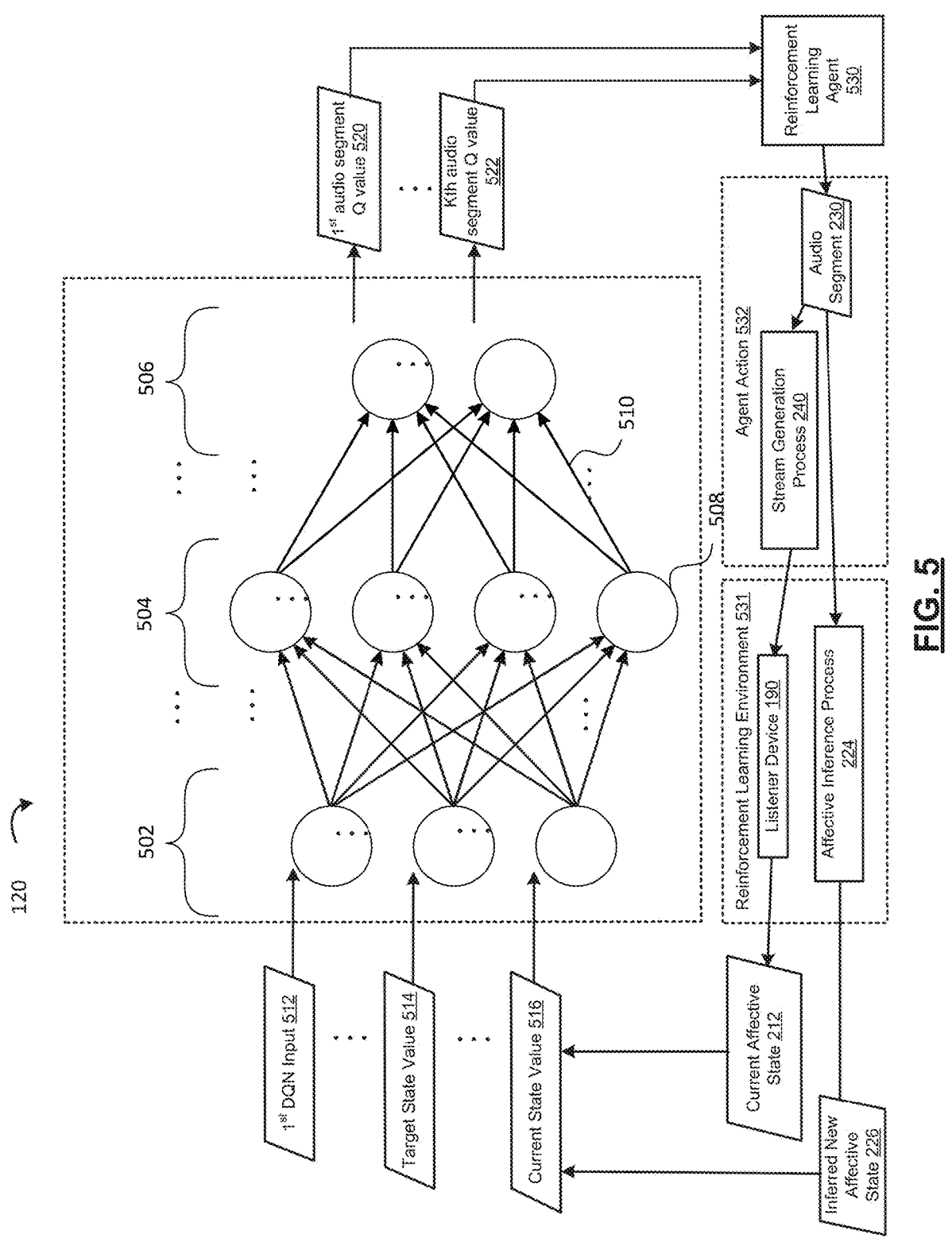
FIG. 5 is a schematic diagram showing a neural network for identifying audio segments likely to achieve target affective responses according to example embodiments described herein.

Example implementations of the affect inference machine learning model and segment identification machine learning model are now described in greater detail, including the processes for training each model, with reference to FIGS. 4A-B and 5 respectively.

FIG. 4A shows a schematic of an example embodiment of an affect inference machine learning model as an affective inference neural network 140. The affective inference neural network 140 comprises at least an input layer 402, one or more intermediate layers 404, and an output layer 406 of neurons 408. The input layer 402 receives data input values (shown here as $1^{st}$ MIR feature value 412 through Mth MIR feature value 414 and one or more non-MIR data values 416) and transforms these inputs using known techniques to provide outputs 410 to neurons in the first intermediate layer 404. The neurons 408 of each of the intermediate layers 404 weight each of the outputs 410 received from the previous layer and transform the weighted output values to produce a further set of outputs 410 to the next layer. The neurons 408 of the output layer 406 similarly weight their received outputs 410 and transform the weighted outputs to generate output values (shown here as valence 420 and activation 422). By adjusting the weights applied to the inputs of each neuron 408 during training, the affective inference neural network 140 can be trained to infer a likely affective response (defined here as an inferred valence value 420 and activation value 422) of a listener to a set of audio features, such as MIR feature values 412 through 414. Additional non-MIR or non-audio feature values may also be used to train and run the affective inference neural network 140: for example, some embodiments may use variables such as the time of day or listener environment to assist the affective inference neural network 140 in making inferences about a user's likely affective response.

In other embodiments, different machine learning models can be used in replacement of the neural networks shown in in FIGS. 4A-B and 5. The affective inference neural network 140 can be replaced by various forms of supervised and unsupervised machine learning systems while maintaining the same core inputs and outputs needed to infer the user's affective state based on a selection of music and/or audio. Similarly, the DQNs 120 can be replaced by various forms of supervised and unsupervised machine learning systems while maintaining the same core inputs and outputs needed to select audio segments based on inferred effectiveness in inducing the desired affective trajectory in the listener.

In some embodiments, a recurrent neural network can be used for the affective inference neural network 140, thereby allowing for MIR features over time series to be used as a series of inputs, and resulting in the output of the inferred state based on a sequence of musical features instead of a mean representation of the time-based MIR features for an entire segment of music. This may allow the predictions of the affective inference neural network 140 to be more granular and over time series, providing a more realistic representation of the musical experience (since human cognition perceives music over time as opposed to a track as a cohesive whole).

FIG. 4B shows an example recurrent affective inference neural network (AINN) 430. The MIR extraction process 225 is used to extract segment MIR features 183 from the audio segment 230 selected by the audio segment identification process 222, referred to here as an N-length array 433 of global MIR features of the audio segment 230 and shown as a $1^{st}$ global MIR feature 435 through Nth global MIR feature 436. Global MIR features may represent musical features of the entire audio segment 230, e.g. tempo. A series of short sub-segments (also called epochs) of the audio segment 230 (e.g., 30-second sub-segments) are also each analyzed for MIR features by the MIR extraction process 225 to generate a plurality of timeseries MIR feature arrays, each timeseries MIR feature array 434 corresponding to a sub-segment and including $1^{st}$ timeseries MIR feature 438 through to Nth timeseries MIR feature 440 for the current sub-segment. The timeseries MIR features 438 ... 440 of the timeseries MIR feature array 434 each represent a feature of the current epoch of the audio segment 230, e.g. mel-frequency cepstrum (MFC) spectrogram values for a specific epoch in time of the audio segment 230.

At each time step, each global MIR feature of the global MIR feature array 433 and each MIR feature of the timeseries MIR feature array 434 for a current epoch (e.g. beginning with the first 30-second sub-segment) is provided as an input to the recurrent affective inference neural network 430, along with other input data such as a current affective state 212 and other data such as contextual information 432. Contextual information 432 may include, e.g., values stored to represent a user's profile (e.g., personality, age, gender, etc.), taste profile (e.g., music preferences), time of day, weather, etc. At each subsequent time step, the timeseries MIR feature array 434 for the subsequent epoch (e.g. the second 30-second sub-segment) is provided as inputs 438 ... 440 along with the other inputs 212, 432, 435 ... 436, and the output of the timeseries neurons is provided as a further set of feedback inputs, thereby providing time-based recurrence. The recurrent affective inference neural network 430 predicts an inferred affective state 450 (e.g., valence and activation values) that will be induced in the listener by listening to the audio segment 230, based on these inputs.

Before being deployed as part of the affective music recommendation system 100, the affective inference neural network 140 may first undergo an initial training process. Some embodiments may carry out the initial training using techniques and/or datasets similar to those described in the following publication: Vempala, Naresh & Russo, Frank. (2012). *Predicting emotion from music audio features using neural networks*. Proceedings of the 9th International Symposium on Computer Music Modeling and Retrieval (CMMR) (hereinafter Vempala), which is hereby incorporated by reference in its entirety. Vempala describes the use of a selected subset of MIR features of a music collection to train a neural network to predict affective response of a human subject listening to the music. Specifically, Vempala uses 13 low- and mid-level MIR features pertaining to dynamics, rhythm, timbre, pitch and tonality: rms, lowenergy, eventdensity, tempo, pulseclarity, zero cross, centroid, spread, rolloff, brightness, irregularity, inharmonicity, and mode. These MIR features of the music are used as inputs to a feedforward neural network, which produces valence and arousal (i.e. activation) output values. Self-reported affective valence and arousal information is collected from the subjects after listening to the music. Backpropagation is then used to train the neural network using a loss function comparing the predicted valence/arousal outputs to the user self-report data.

Example embodiments may perform initial training of the affective inference neural network 140 using a different set of audio features from the 13 features used in Vempala.

Vempala normalizes the various MIR feature values of interest on a scale from 0 to 1. Similarly, example embodiments may normalize the MIR data and/or other audio data or non-audio data used by the affective inference neural network 140.

Once initial training has been completed, the affective inference neural network 140 may be considered effective in predicting listener-independent affective responses to audio features. However, in order to train the affective inference neural network 140 to predict the affective responses of a specific listener, it may be trained using affective feedback from that listener. The deployed affective inference neural network 140 may also use more audio features and non-audio features as inputs in order to identify influences of less universal factors to the affective responses of that listener. By comparing the affective inferences made at step 310 with the updated current affective state data received from the listener at step 322, the affective inference neural network 140 can use backpropagation or other training techniques to update the weights used by its neurons 408 to improve its modeling of the listener's affective responses to sets of audio feature values.

Some embodiments may provide an inference training process allowing a listener to train his or her personalized affective inference neural network 140 on-demand by listening to audio segments and providing affective state data before and afterwards. This data may be used to train the affective inference neural network 140 as described above.

In use or during training, the affective inference neural network 140 may sometimes encounter outliers: audio stimuli that elicit affective responses in the listener that are highly dissimilar to the predictions of the affective inference neural network 140. To avoid overfitting, the feedback data from these outlier stimuli may be segregated from the feedback data used for training. This segregated data may be used by a separate analysis process to extract listener-specific data that may assist in identifying the patterns in the listener's idiosyncratic response to the stimulus. For example, a listener may have an extreme affective response while listening to an audio segment because of other events in the listener's environment unrelated to the audio segment, or the listener may have emotional associations with a specific song that are unrelated to the audio features of that song. These non-audio-feature-related associations may not be used to train the affective inference neural network 140, but may, for example, instead be used to identify non-audio data that could potentially be used as input to the affective inference neural network 140 to assist with the accuracy of future predictions.

FIG. 5 shows a schematic of an example embodiment of an audio segment identification machine learning model as a deep learning neural network or deep Q network (DQN) 120. The DQN 120 comprises at least an input layer 502, one or more intermediate layers 504, and an output layer 506 of neurons 508. As in the affective inference neural network 140 of FIG. 4A, the input layer 502 receives data input values and transforms these inputs using known techniques to provide outputs 510 to neurons in the first intermediate layer 504. The neurons 508 of each of the intermediate layers 504 weight each of the outputs 510 received from the previous layer and transform the weighted output values to produce a further set of outputs 510 to the next layer. The neurons 508 of the output layer 506 similarly weight their received outputs 510 and transform the weighted outputs to generate output values.

The DQN 120 is effectively identical to a standard deep learning neural network with the key differentiation of it being utilized as the core prediction component of a reinforcement learning (RL) agent 530 as it navigates the reinforcement learning (RL) environment 531. This type of deep learning neural network also uses training techniques like backpropagation, but in DQN models reward data 273 is used to drive the training process, as opposed to correlated datasets as seen in the training process of the standard deep learning neural network used in the affective inference neural network 140. Modelled after Q-learning systems, this system replaces a standard Q-table with a Deep Q Network, allowing the RL agent 530 to be trained exponentially faster. In a standard Q-table, the Q-values of all possible actions based on the current state of the environment are shown in a tabular format based on previous sessions during training. This requires multiple iterations of each state-action relationship before the RL agent 530 is able to optimize its performance. When there are a large number of states and actions, this training becomes expensive and inefficient. By replacing the Q-table with a deep learning neural network, or DQN 120, the inputs of the network represent all possible state relationships and the outputs represent the Q-values of all possible actions. These networks allow for relational training that approximate the values of all actions with each iteration, drastically reducing the time it takes to optimize an RL agent's performance. See, e.g., LeCun, Yann & Bengio, Y. & Hinton, Geoffrey. (2015). *Deep Learning*. Nature. 521. 436-44. 10.1038/nature14539, as well as Mnih et al, 2013, *Playing Atari with Deep Reinforcement Learning*, Nature. 518. 529-533. 10.1038/nature14536, which are each hereby incorporated by reference in their entirety.

As shown in FIG. 5, the Q-values 520 . . . 522 are fed to the reinforcement learning agent 530, which takes action 532 by selecting an audio segment 230 and feeding the audio segment 230 to one of two alternative environments: the actual environment, i.e. the user's actual affective state, or a simulated environment, i.e. the affective inference process 224. In the former case, the stream generation process 240 generates the audio stream and sends it to the listener device 190, and the listener device 190 then provides updated current affective state data 212 after the listener has been exposed to the audio stream. In the latter case, the audio segment 530 is fed to the affective inference process 224, which generates an inferred new affective state 226.

The inputs shown in FIG. 5 ($1^{st}$ DQN input 512, target state value 514, and current state value 516) are a partial and simplified list of the inputs used in example embodiments. In some embodiments, the DQN inputs (such as $1^{st}$ DQN input 512) may include the contextual cues 191 described above with reference to FIGS. 2A-2B. An example embodiment may use the following list of inputs at runtime: mode (indicating a target affective state, such as "calm", "focus" or "energized"), step count (indicating the total number of audio segments 230 to be included in sequence in the audio stream 234), current step (indicating which of the sequence of audio segments 230 is currently being identified), initial state valence (the valence value of the listener's current affective state 212 identified at the beginning of the session), initial state activation (the activation value of the listener's current affective state 212 identified at the beginning of the session), updated state valence (the valence value of the inferred new affective state 226 or updated current affective state 212 prior to the current step), and updated state activation (the activation value of the inferred new affective state 226 or updated current affective state 212 prior to the current step).

Users may have drastically different reactions to music that change on any given day depending on how the user is feeling and what their current musical taste preferences are. Accordingly, in some embodiments the system 100 may implement an additional personalization method by providing additional inputs to the Deep Q Network 120 and the Affective Inference Neural Network 140 allowing other factors to influence the prediction process. In some embodiments, the desired musical aesthetic a user is seeking in that moment may be identified and provided to as a further input. For instance, if a user is sad, and they feel like listening to music that loud and rebellious (e.g., Rock music), they would likely have a different reaction to a combination of MIR features, a library of tracks, or a selection of audio segments than if they were sad and feeling like listening to reflective and complex music (e.g., Classical music). This distinction between current affective state (e.g., sad) and current desired emotional content of music (e.g., loud and rebellious vs. reflective and complex) could be represented using data values and provides as further inputs to the neural networks 120 and 140 in FIGS. 4A-B and/or 5 (e.g., a "Current Music Taste Preference" input to input layer 402 or 502).

User profile data can also be leveraged as potential inputs to the neural networks 120 and 140 represented in FIGS. 4A-B and 5 (e.g., one or more "User Profile Data" inputs to input layer 402 or 502). User profile data could include data fields such as user demographic, baseline music taste profile, baseline mood profile, and personality profile. These and other user profile data could potentially all have value when predicting how a user will react to music tracks or MIR features given their current state. Some of this data could be collected from users using the user interface screens described below with reference to FIGS. 8 and 9. Some such data could also be inferred by the system 100 based on the user input provided by users via the user interface screens of FIGS. 6-7; for example, a user's musical genre preferences might be inferred from their genre choices in UI screen 608 in FIG. 6 over multiple sessions.

Contextual information, such as time of day and the user's surroundings (e.g., whether they are in a loud or quiet place), may also be used as a source of relevant data by the system 100 and may be provided as one or more additional data inputs to the input layers 402 and/or 502 of the neural networks of FIGS. 4A-B and/or 5. The user's current environment and context may have a high impact on how music is cognitively received by the user and may provide valuable input data to the system 100. Contextual data may be gathered by the system 100, e.g., by the user interactions shown in screens 604 and 610 of FIG. 6, and screen 1002 of FIG. 10.

The user's current state value 516 may also be provided as an input into the input neurons 402 of FIG. 4A. By using the user's current state value 516 to inform the predictions of the affective inference neural network 140, the system 100 may factor in the current affective state of the user when predicting what their affective outcome will be given exposure to a combination of MIR features. For example, a segment of music could evoke two very different emotions depending on a user's starting emotional state.

During inference training mode, the input layer neurons 502 will receive the output data from the affective inference neural network 140 in order to set the initial weights to the DQN 120. A target state value 514, as well as all other variable parameters (e.g. number of steps), are generated randomly and the outputted audio segment Q values 520 through 522 are then used by RL agent 530 to select an audio segment 230. This audio segment 230 is converted into segment MIR data 183 by a MIR extraction process 225, and the affective inference neural network 140, effectively acting as the RL environment 531, predicts what the next affective state would be based on the action taken by the RL agent 530. This new state (i.e. inferred new affective state 226) is then used as the current state value 516 for the next step of the prediction sequence, and this cycle continues until all steps are completed. This full sequence runs through thousands of iterations where a new target and a new number of steps is randomly generated each time. During initial training, this process is generally done through 200,000-500,000 iterations in order to fully optimize the DQN 120.

In some embodiments, the MIR extraction process 225 extracts segment MIR features 183 from the audio segment 230 in real-time, or a table is referenced of previously extracted features. MIR feature extraction from audio segments may be performed using known techniques.

By adjusting the weights applied to the inputs of each neuron 508 during training, the DQN 120 can be trained to select or identify an audio segment 230 having an optimal Q value 520 . . . 522 relative to the other audio segment candidates, indicating a high likelihood of inducing the target affective state over a series of steps or if utilizing an affective trajectory 218, in an acute fashion per step. Training may take place in two modes: initial training, and re-training or updating during idle time.

Initial training of the DQN 120 is carried out before deployment of each DQN 120. Each user of the affective music recommendation system 100 has a plurality of DQNs (e.g. DQNs 122, 124 through 126) associated with his or her personal account, as well as a personal affective inference neural network 140. The affective inference neural network 140 is trained to model the affective responses of the user (listener) to different combinations of audio features and other non-audio variables as described above. The affective inference neural network 140 then acts to model the environment in which each DQN 120 operates, i.e. it stands in for the user's actual affective responses. The affective inference neural network 140 provides all of the inferred new affective state 226 data, which acts as the current state data 516 used to train the DQN 120. In initial training, the reward function 272 is also fed the inferred new affective state 226 data from an affective inference neural network 140, avoiding the need for a user to provide final affective state data (i.e. current affective state data 212 provided at the end of a session). In initial training, each DQN 120 is walked through a training regimen comprising different input variable combinations. The training regimen may be generated randomly, e.g. by generating random values for each input variable and iterating different sets of random inputs for a predetermined number of reinforcement iterations. In other embodiments, the training regimen may comprise a systematic survey of different input values, e.g. covering the entire affective space, with valence and activation values for both initial and target affective state inputs being changed by predetermined amounts after each iteration of reinforcement. In some embodiments, the inputs to the DQN 120 used during training are different from those used during runtime as described above: for example, rather than tracking the number of steps and the progress toward the final target affective state 214, the DQN 120 may simply evaluate the accuracy of each audio segment selection step in isolation.

In some embodiments, re-training or updating of the DQN 120 during idle time can also be done using a newly updated affective inference neural network 140. The affective inference neural network 140 is updated after a user session using actual updated current affective state feedback from the listener, as noted above. Once the affective inference neural network 140 has been updated, each DQN 120 may use system idle time when the user is not engaged with the system to re-train itself using the updated affective inference neural network 140. The initial training regimen is applied again to each DQN 120 to re-train it using the updated affective inference neural network 140 as its environmental simulation.

In embodiments using a different reinforcement learning approach in place of the DQN 120, the DQN 120 shown in FIG. 5 could potentially be a different reinforcement learning algorithm representation, and all the data being provided as inputs 512, . . . 514, . . . 516 to input layer neurons 502 (such as a step count value or a target state value) could be treated as a vector of input data representing the state of the environment as used by the chosen reinforcement learning algorithm. This input vector would still be treated as the data enabling the inference behavior of the algorithm replacing the DQN 120. In some embodiments, the functions of the DON 120 and reinforcement learning agent 230 could be carried out by a single model or algorithm that would use the input vector 512, . . . 514, . . . 516 to predict the Agent's Action 532, resulting in Audio Segment 230 as described above. The algorithm replacing the DQN 120 and/or RL agent 530 could be a different DQN, a simple Q-table, an actor/critic model, or an environment model/planner implementation within a model-based RL algorithm. Different approaches may provide various advantages and disadvantages, but they could all theoretically provide comparable results.

The use of physiological data 208 to determine a user's current affective state 212 may employ sensors and techniques known in the field of affective computing, such as wearable sensors, cameras, and/or other sensors. Galvanic skin response (GSR), electroencephalography (EEG) signals, breathing patterns, heart rate, pupil dilation, subdermal blood flow, muscle tone, and other biomarkers may be correlated with various affective phenomena in humans. These biomarkers may be detected using biosensors such as GSR sensors, breathing sensors, electrocardiogram or electroencephalogram electrodes, active or passive visual sensors using visible and/or invisible light spectra, eye tracking systems, and electromyogram electrodes. One or more such sensors may be used in conjunction with the system 100 to collect physiological data 208, which may be processed by the affective music recommendation system 100 or by a process external to the system 100 to identify a listener's affective state. In some cases, the physiological data 208 is gathered and/or processed by the listener device 190. Collecting and/or processing the physiological data 208 may be carried out using techniques such as those described in: Shu L, Xie J, Yang M, et al. A Review of Emotion Recognition Using Physiological Signals. *Sensors (Basel)*. 2018; 18(7): 2074. Published 2018 Jun. 28. doi:10.3390/s18072074, which is hereby incorporated by reference in its entirety. In other embodiments, such physiological data can also be used as separate inputs, in addition to the affective state data, when other biomarkers are tied to the desired outcomes from using this system. For example, in embodiments where desired outcomes include a target affective state as well as a target physiological outcome (i.e. heart rate reduction of 10%), physiological data can also be used as an element in representing the current state 516 of the user and the target state 514.

Other data gathered from a listener may also be used to infer affective states. Camera data may be used to analyze facial expressions or other behavioral patterns correlated with affective state or affective response. Speech recordings or transcriptions may reveal patterns of prosody, intonation, or speech content correlated with affective state or affective response. In some embodiments, the listener device 190 or another process internal or external to the system 100 may be used to collect and/or process camera, speech, or other user data to assist in identifying a listener's current affective state 212. Camera data showing a user's face, for example, may be analyzed for affective state information according to techniques such as those described in: Samara, A., Galway, L., Bond, R. et al. Affective state detection via facial expression analysis within a human-computer interaction context. *J Ambient Intell Human Comput* 10, 2175-2184 (2019) doi:10.1007/s12652-017-0636-8, which is hereby incorporated by reference in its entirety.

Figure 6:
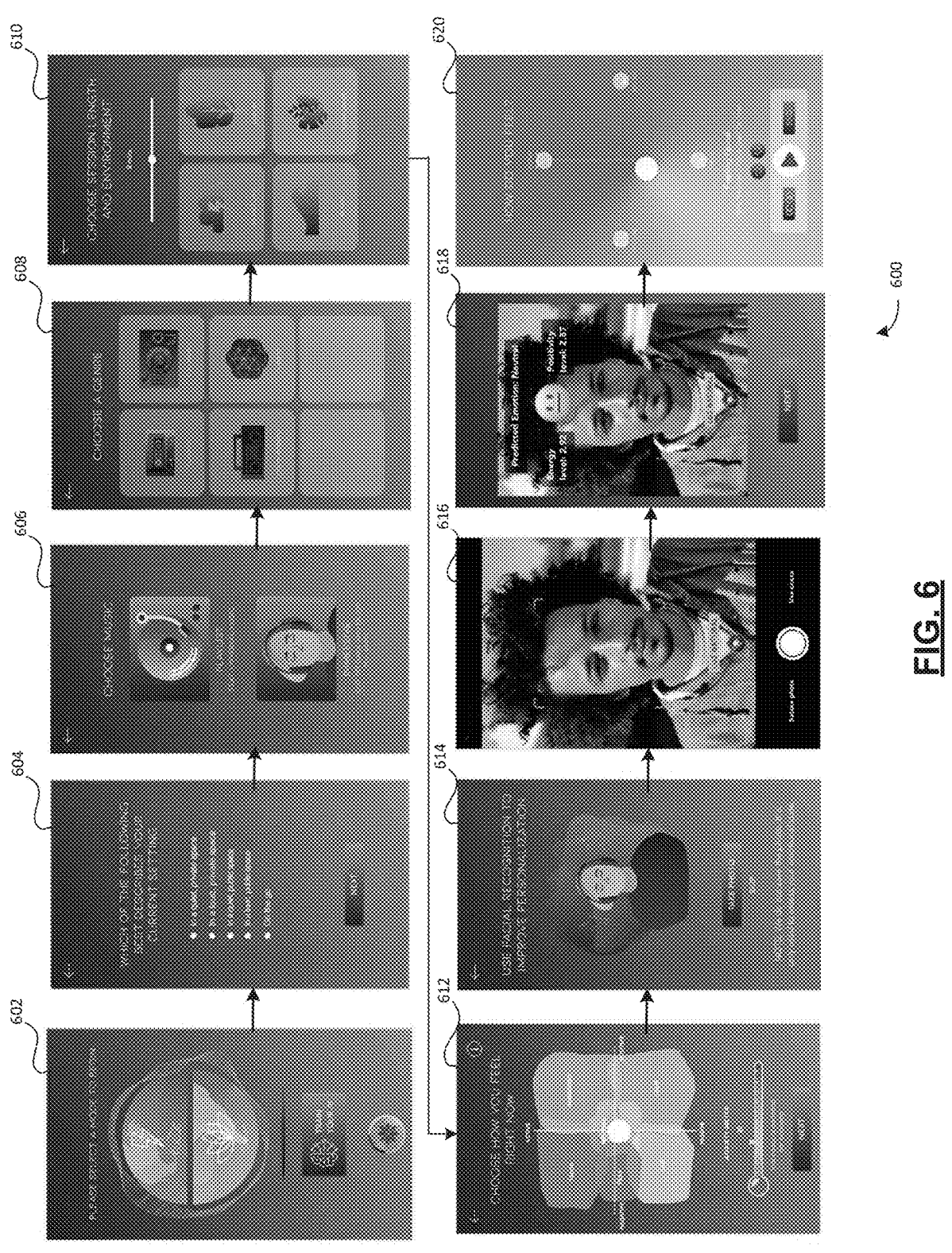
FIG. 6 is a sequence of example user interface screens of a listener device showing a pre-stimulus listener interaction according to example embodiments described herein.

FIGS. 6-10 show example user interface (UI) screens. These screens may be shown to a user on the touchscreen 194 of the listener device 190, and may serve to collect user input as well as providing information to the user. With reference to FIG. 6, a session initiation sequence 600 of UI screens is shown that are presented to a user to begin a session of interaction with the affective music recommendation system 100. The first screen 602 presents a set of mode options to the user, each mode corresponding to a target affective state 214. The modes shown on this screen 602 are "focus" (e.g. corresponding to high-activation) and "calm" (e.g. corresponding to low-activation). A "train your AI" input area is also presented which, when selected may allow the user to enter into an inference training process for the affective inference neural network 140 as described above.

One the user has selected a target affect mode, the system 100 may use this input to determine the target affective state 214 to be used during the user session. A second screen 604 is then presented to the user allowing the user to identify the nature of his or her current setting or environment, e.g. whether the environment is quiet and private, loud and private, quiet and public, loud and public, or varying over time due to travel. A third screen 606 allows the user to select between a playlist mode and an immersive mode. This screen 606 may, for example, allow the user to be presented with stream data 236 showing a playlist (in playlist mode) or simply to have the stream data 236 include the audio stream 234 itself, sent directly to the listener device 190 for auditory presentation without further user interaction. In some embodiments, this mode selection screen 606 may allow the user to specify which subset 220 of audio segments from the music library 184 to use for the user session (and therefore which DQN to select from DQNs 122, 124 to 126).

A fourth screen 608 allows a user to select a genre of music to use for the user session. This may select, or further narrow down, the possible subset 220 of audio segments to use for the user session. A fifth screen 610 allows the user to select a duration for the audio stream 234. The user-selected duration may be used to determine the number of audio segments 230 to include in the audio stream 234, which in turn determines how many segment identification steps are carried out by the DQN 120. In some embodiments, the user may also use this screen 610 to select an ambience track and determine the length of their session (i.e. the number of steps to be taken by DQN 120) or other audio characteristics of the audio stream 234.

A sixth screen 612 allows the user to identify his or her current affective state 212. The illustrated example uses a two-dimensional representation of affective space, with activation as the vertical axis and valence as the horizontal axis. The two-dimensional space is further populated with a plurality of regions corresponding to named affective states: e.g. the green region in the upper right quadrant of the space is named "energized", the red region in the upper left quadrant is named "tense", the white region in the lower left quadrant is named "sad", the blue region in the lower right quadrant is named "calm", the dark grey or black region in the middle left area is named "fear", and the grey region around the center is named "neutral". The user may move a state indication cursor, shown here as a white circle near the center of the space, to a location in the space corresponding to his or her self-evaluated current affective state or mood. Some embodiments may also include additional inputs, such as the anxiety meter slider shown at the bottom of the screen 612, to indicate a third dimension or additional data to supplement the two-dimensional affective stat self-report indication above.

A seventh screen 614 allows a user to provide facial expression data to supplement or as an alternative to the self-reported data from screen six 612. If the user chooses to take a photo, an eighth screen 616 is presented using a camera control interface of the listener device 190. Once the user takes a picture of his or her face at screen eight 616, a ninth screen 618 shows the picture annotated with the system's affect analysis based on, e.g., the user's facial expression.

Some embodiments may train or calibrate a facial affect analysis process or other process for correlating affect with user data (e.g. physiological signals, speech data, and so on as described above) using self-report data collected from user input such as that at screen six 612.

Once the user's current affective state 212 has been identified based on the inputs from screens six 612 and/or nine 618, the system 100 generates the audio stream 234 and sends audio stream data 236 to the listener device 190 as described above. The user may be presented with a tenth screen 620 showing metadata corresponding to the first audio segment in a music control display at the bottom of the screen 620, shown here as the title and duration of the song "Feeling Good", along with music playback controls. At the top and middle of the screen 620, an updated current affective state input area is provided for the user to initiate updates of his or her current affective state during the user session, as described above.

Figure 7:
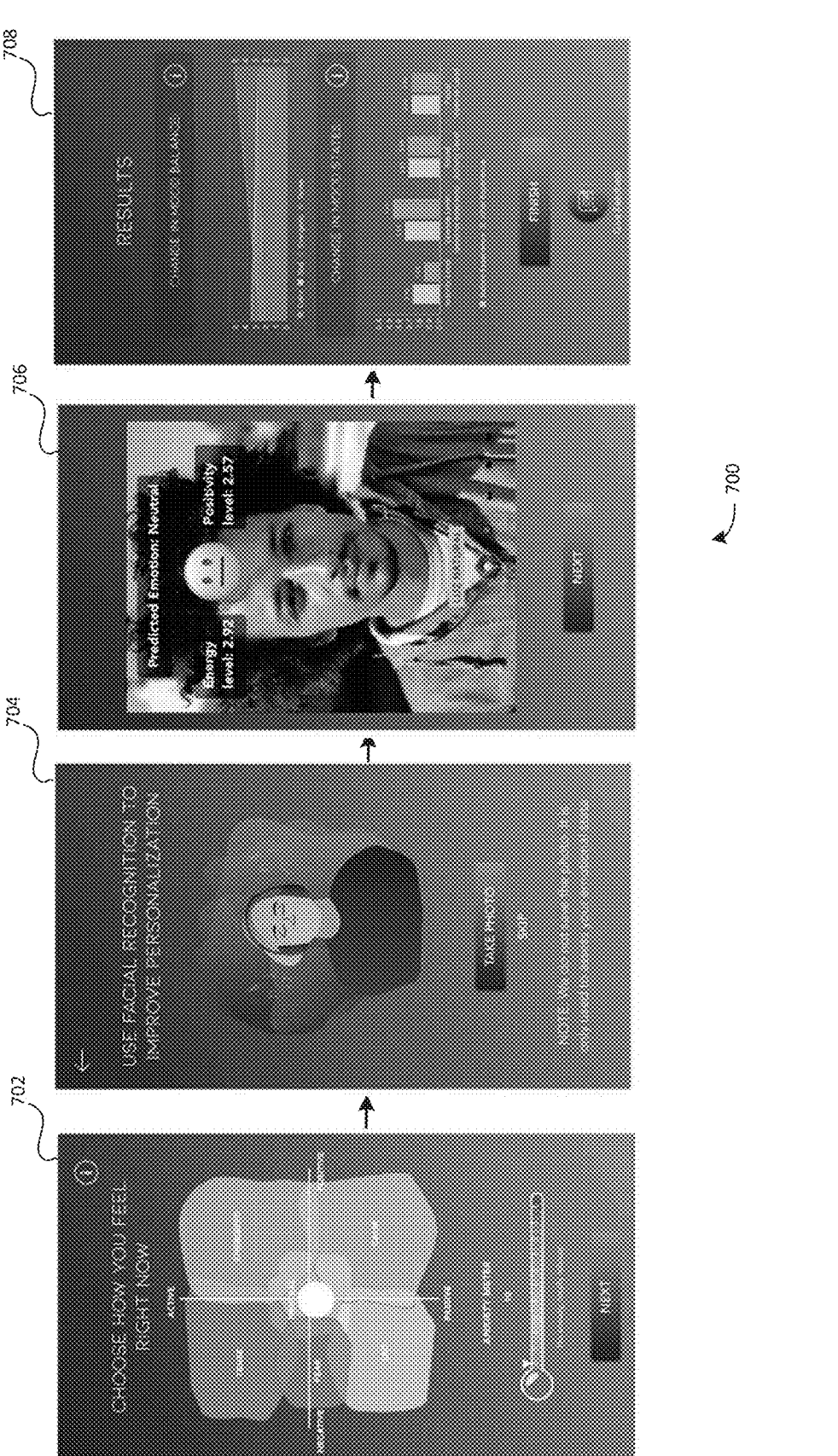
FIG. 7 is a sequence of example user interface screens of a listener device showing a post-stimulus listener interaction according to example embodiments described herein.

FIG. 7 shows a session ending sequence 700 of UI screens that are presented to a user to end a session of interaction with the affective music recommendation system 100. The first screen 702 presents an affective state input display for reporting the user's updated current affective state at the end of the user session, after having listened to the audio stream 234. This updated current affective state data is used to update the affective inference neural network 140 as described above. A second screen 704 presents the option to supplement or replace the self-report data from first screen 702 with facial image data, following the same process as pre-session screens seven 614 through nine 618 to collect and analyze this data and resulting in third screen 706. A fourth screen 708 may then show to the user the affective response results based on the user's initial reported current affective state 212 from screens 612 and 618 and the user's subsequently updated current affective states from screens 620, 702, and 706. A graph at the top of the screen 708 may show the user's affective trajectory over the session and may include identification and/or magnitude of one or more named affective states over time. A set of bar graphs at the bottom of the screen 708 may break down the user's affective response by activity and valence and/or by self-report and facial analysis.

Once the user session has ended, the system 100 may use idle time to re-train the DQNs 120 as described above.

Figure 8:
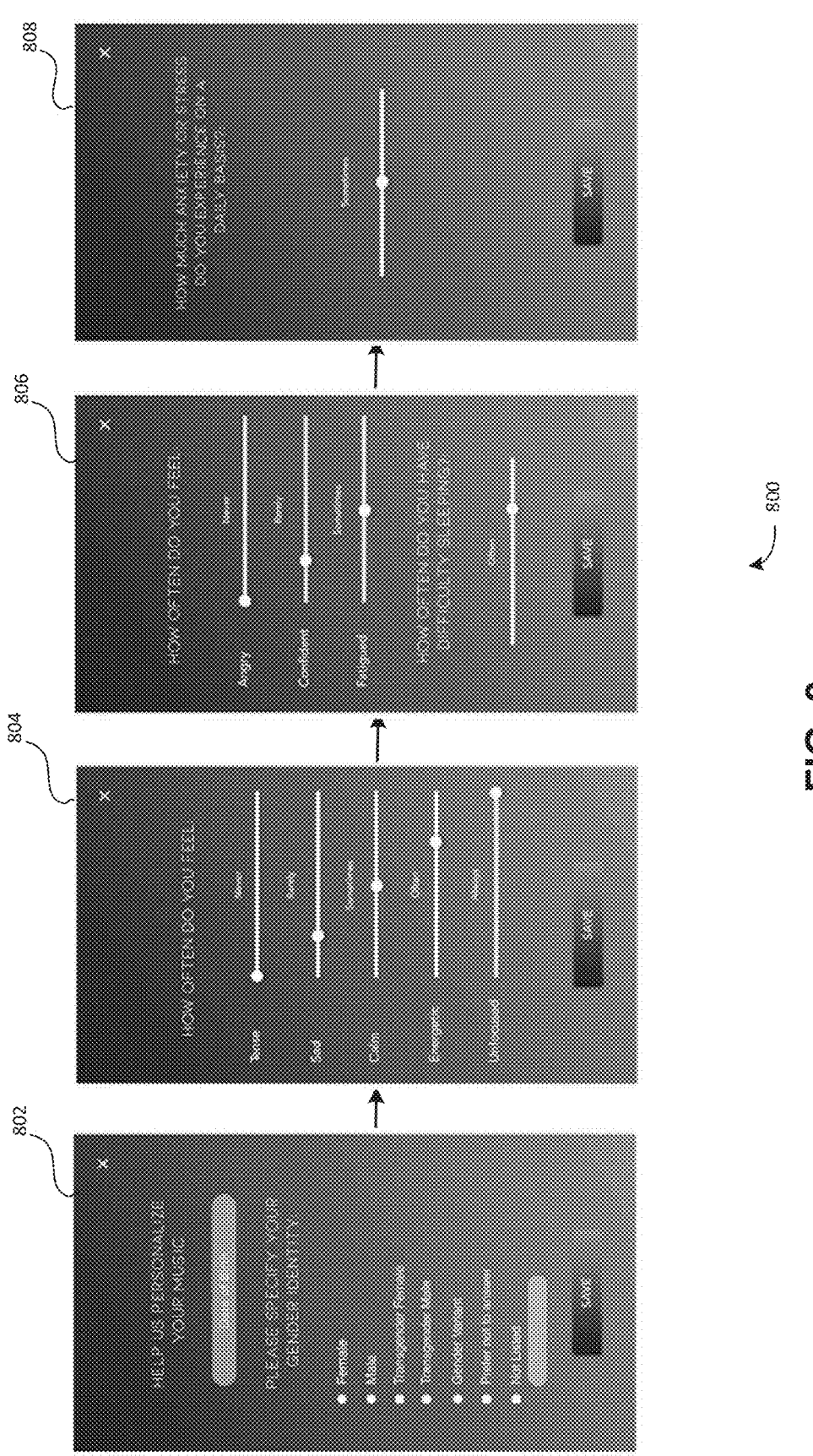
FIG. 8 is a sequence of example user interface screens of a listener device showing a personalization listener interaction according to example embodiments described herein.
Figure 9:
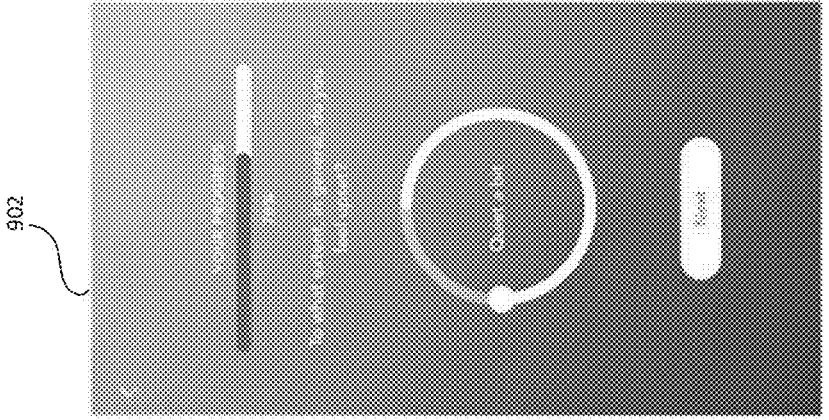
FIG. 9 is an example user interface screen of a listener device presented to a user as part of a profile creation process according to example embodiments described herein.

FIG. 8 shows a user customization sequence 800 of UI screens that are presented to a new user or to a user who has chosen to update or deepen his or her personal profile stored by the system. The first screen 802 prompts the user to provide personal data such as date of birth and gender identity. A second screen 804 prompts the user to identify how often he or she experiences each of a number of named affective states. A third screen 806 prompts the user regarding frequency of an additional set of named affective states and also regarding how often the user has trouble sleeping. A fourth screen 808 prompts the user to identify how often he or she experiences stress or anxiety. Based on the user inputs provided through the sliders and other user input elements in this sequence 800, the system may calibrate or customize the training and/or operation of the various parts of the system 100. For example, a user who frequently feels sad but rarely feels energetic may have his or her affective inference neural network 140 calibrated to normalize the weights given to these states based on a baseline or average set of affective state values specific to the user. The system may also use this user input data to make recommendations to the user for how to employ the system to achieve the user's goals, such as mental health or mood management goals. FIG. 9 shows an example user profile data collection UI screen 902 presented to a user as part of a profile creation process. A progress bar at the top of the UI screen 902 shows how far the user has progressed through the user profile creation process. The bottom part of the UI screen 902 shows an input area for the user to indicate to what extent, in general, they feel upset.

Figure 10:
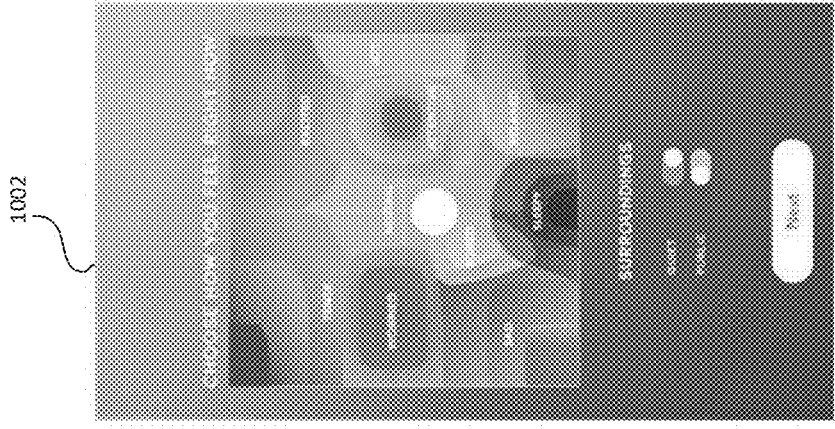
FIG. 10 is an example user interface screen of a listener device showing a contextual information gathering interaction according to example embodiments described herein.
Figure 10:

FIG. 10 shows an example contextual information gathering UI screen 1002. Contextual information used as inputs to the neural networks or reinforcement learning algorithms of FIGS. 4A-B and 5 may be gathered using the contextual information gathering interaction of this screen 1002. The top part of the screen 1002 shows a current affective state input area as a 2-dimensional affective state indicator. The bottom part of the screen 1002 shows a current environment input area as two switches indicating whether the current environment is quiet or loud, and whether it is private or public. The contextual information may be gathered in association with a timestamp, which may be used by the system 100 to determine a time of day.

In some embodiments, multiple systems 100, or multiple versions of various components of the system 100 (such as DQN 120 or affective inference network 140) could be used to interact with different users. The various systems 100 or components could be individualized by the user, and a storage mechanism could be used to store different systems or different models (e.g. 120 or 140) indexed by a user identifier.

Figure 11:
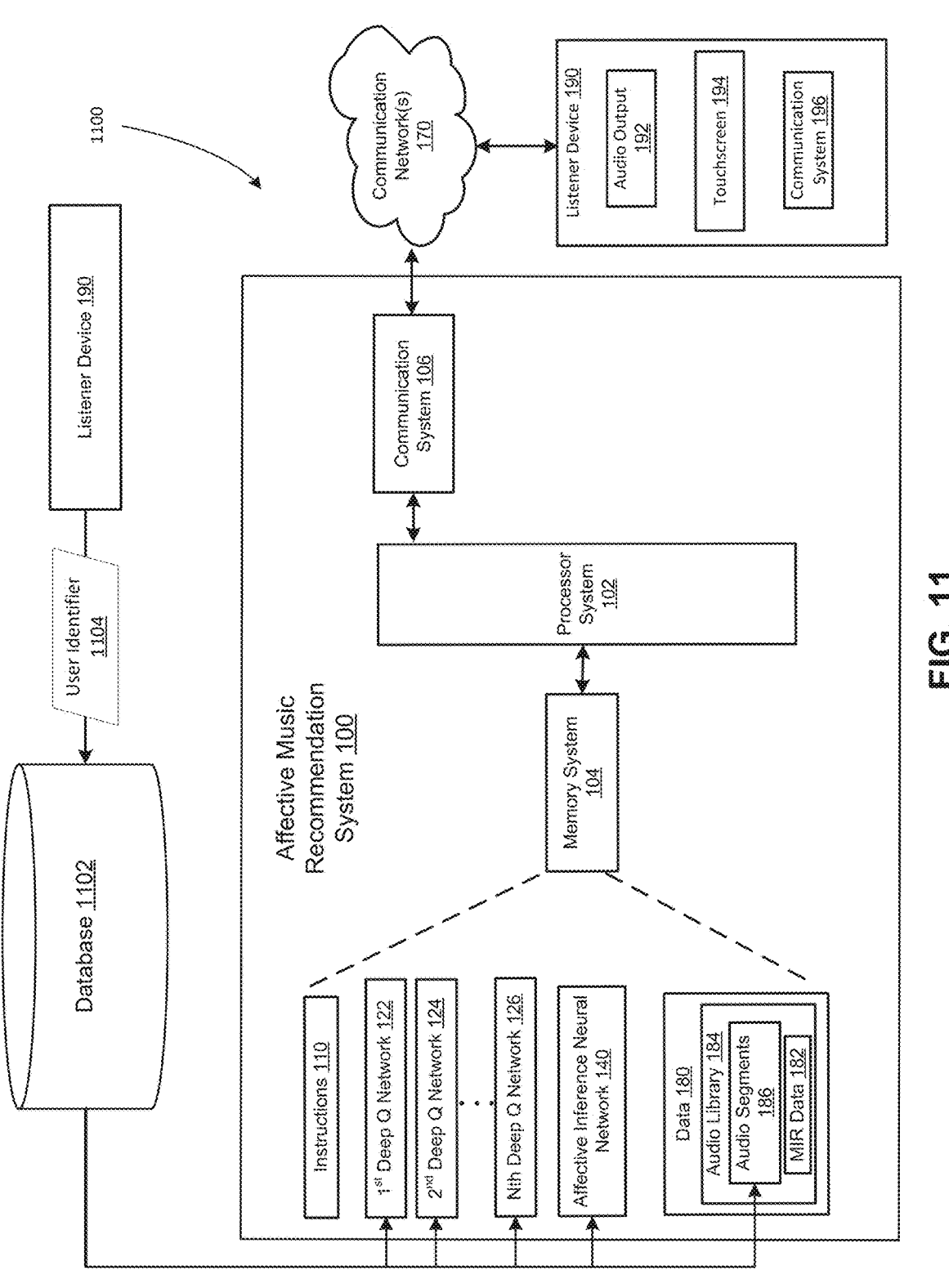
FIG. 11 is a block diagram of an example multi-model system for affective music recommendation according to example embodiments described herein.

FIG. 11 shows an example multi-model system 1100. Each user of such a multi-model system 1100 could possess their own model or models, which could be trained to learn the unique dynamics of how an individual user responds to music. In a multi-model system 1100, a listener's device 190 provides a user identifier 1104 (e.g., a user ID number) to a database 1102 storing individualized machine learning models for individual users, such as individualized DQNs 120 and individually trained affective inference algorithms 140. In some embodiments, a user of such a system 1100 would be able to create their own collections (i.e. subset 220) of audio segments 186 as well, and these could also be stored or identified by the database 1102. The DQNs 122, 124 . . . 126 could be composed of actions (or subsets 220 of audio segments 186) unique to that user, or could be selections from the music library of that user.

In some embodiments of a multi-model system 1100, a DQN 120 and/or subset 220 of audio segments 186 could be selected from the database 1102 by gathering information about a user's baseline music tastes (e.g., as part of the user profile creation process described above with reference to FIGS. 8-9) and matching the user with a DQN 120 and/or subset 220 of audio segments 186 that contain music that aligns with those tastes. Thus, a given multi-model system 1100 as shown in FIG. 11 may be specific to a particular user and a particular subset 220 of audio segments 186 selected from the audio library 184. The subsets 220 of audio segments 186 may be selected based either on the user's choice (e.g. the user's music library) or by an algorithm determining which set would be best for the user in the current context (e.g. based on a user's current affective state 212, setting, and/or environment).

In some embodiments, individual personalization of a multi-model system 1100 takes place in several stages. A user may begin with models that have been trained either based on all users, or based on users of a similar profile (e.g., sharing their music tastes, baseline mood profile, personality profile and/or demographic). A gated process may be used to start the user with these more general models, and gradually train the user's own individual models. Once those individualized models reach a threshold of performance, they would replace the more general models for runtime use.

In embodiments in which personalized models are used, a music enjoyment meter can also be added to provide important input data in the DQN training process. If a user does not like an audio segment, they can annotate the track representing the audio segment. The reward function 272 within the direct training process 270 can factor in either a reward or penalty depending on the rating. This will allow the system to quickly learn whether or not the user enjoys a given audio segment, which could have a major impact on the effectiveness of the audio segment when inducing an affective state in that user.

Figure 12:
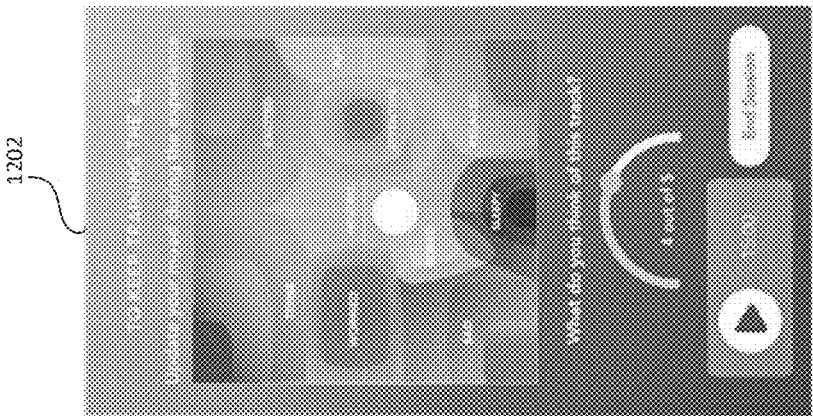
FIG. 12 is an example music enjoyment rating user interface screen 1202 according to example embodiments described herein.

FIG. 12 shows an example music enjoyment rating user interface screen 1202 allowing a user to provide input on their enjoyment of the current audio segment being played. The top portion of the screen 1202 shows an affective state update input area. The bottom portion of the screen 1202 shows playback controls. The middle portion of the screen 1202 shows a music enjoyment input area allowing a user to move a slider to indicate a level of enjoyment of the current audio segment being played.

The elements of a multi-model system 1100 could allow for deep, highly specific personalization over time, starting with contextual personalization, progressing into profile personalization (once enough users in each profile group become active in the network) and even individualistic personalization (once the individual user has enough recorded sessions). Contextual personalization may include data such as initial affective state, current music preference, and time of day. Profile personalization may include data such as personality, demographic, and baseline music taste profile.

In some embodiments, the outputs of the DQN 120 and reinforcement learning agent 230 are selection of MIR features from the library MIR data 182 instead of selection of an audio segment 230 from the audio library 184.

Figure 13:
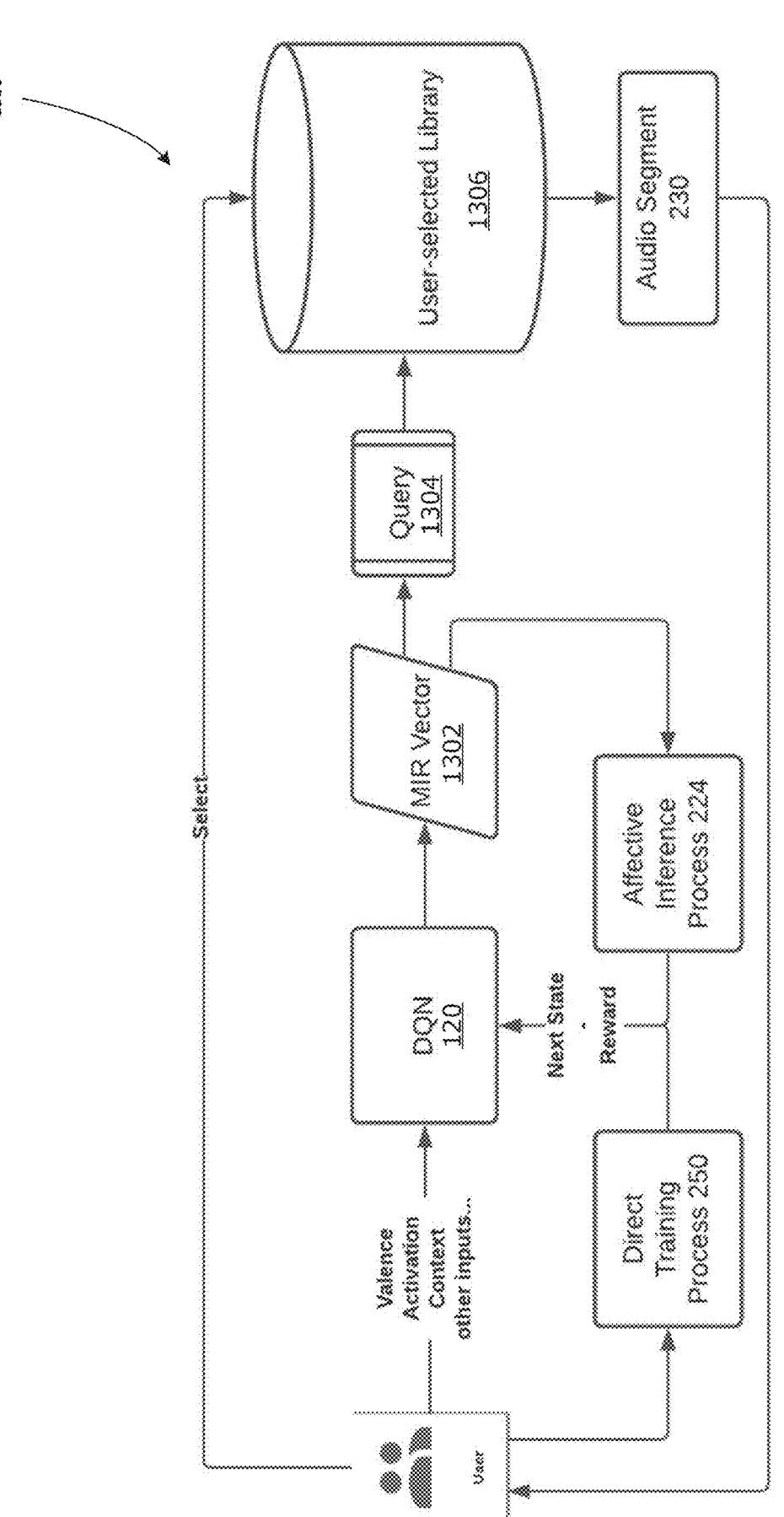
FIG. 13 is an example MIR-feature prediction system according to example embodiments described herein.

FIG. 13 shows an example MIR-feature prediction system 1300. In some such systems 1300, the output neurons 506 of the DQN 120 would include one neuron per MIR feature, which would be used to determine a level or value for each MIR feature. The set of DQN 120 outputs could represent a MIR vector 1302 that could then be matched with an audio segment 230 (e.g., the audio segment of best fit to the MIR features within a given library, such as user-selected library 1306) as part of the agent action 532 by sending a query 1304 including the MIR vector 1302 to the library 1306. These MIR features (e.g., MIR vector 1302) could then be fed into the affective inference process 224, and/or the MIR features could be annotated by the user directly during the direct training process 270. In such embodiments, a user may only one DQN (as the DQN would now be deciding MIR feature combinations), but users may instead have one or more libraries of audio segments 186, depending on the user's current music taste requirements, baseline profile, or libraries (such as library 1306) they've created themselves, from which an audio segment 230 may be selected based on its fit with the MIR features.

Figure 14:
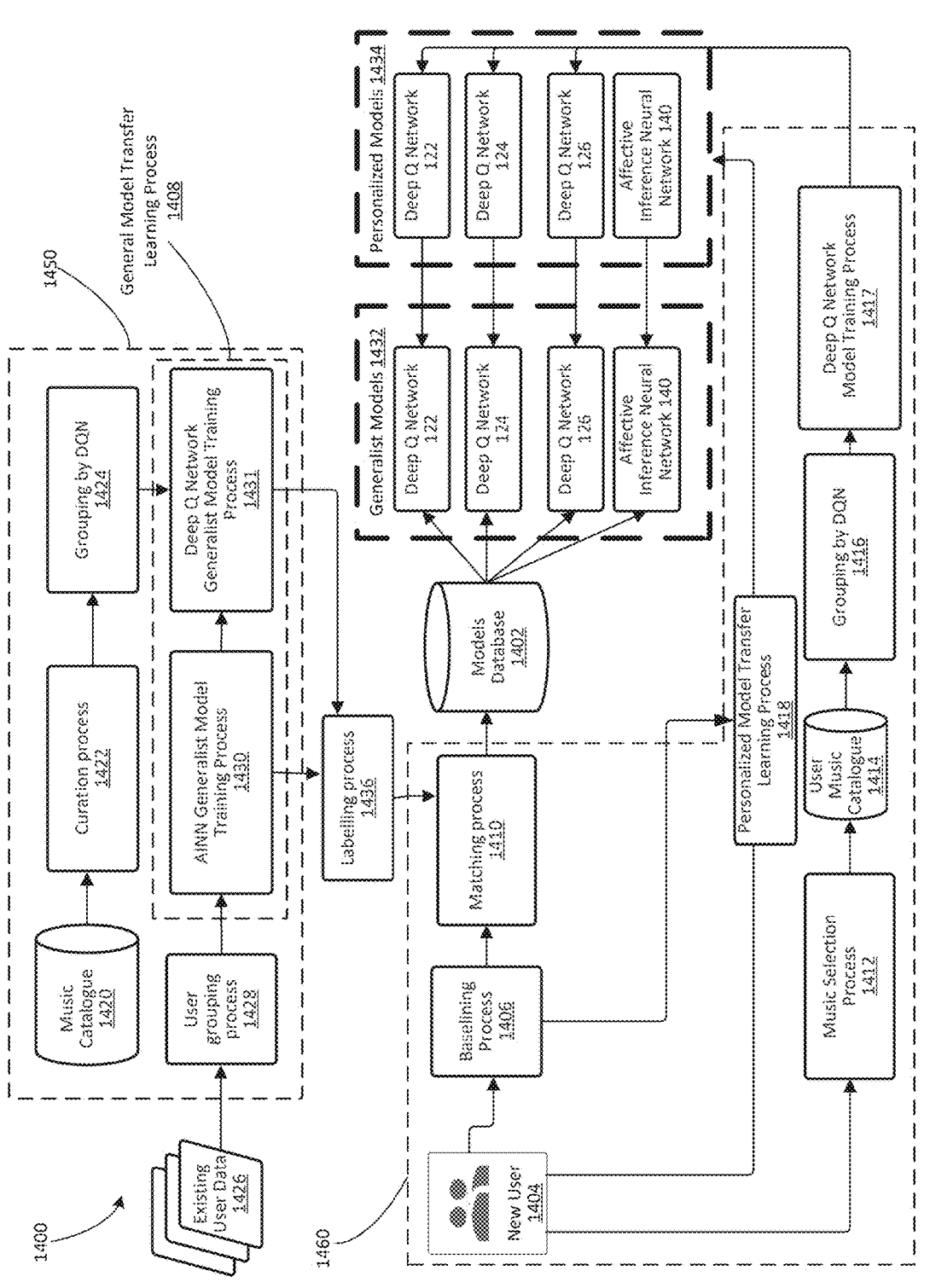
FIG. 14 is a block diagram showing steps and components of an example process for creating a database of music models for a listener according to example embodiments described herein.

FIG. 14 shows steps and components of an example models database generation process 1400 for creating a models database 1402 of affective inference models (e.g., AINN 140) and/or Deep Q Networks 122, 124, 126 specific to a given listener. The models database 1402 may be used, for example, to generate and train the models for each user of a multi-model system 1100.

The models database generation process 1400 includes two stages: a generalist model training process 1450, and a personalized model training process 1460. The models database 1402 is populated with a set of generalist models 1432 and a set of personalized models 1434. Each set of models 1432, 1434 may include, for example, an AINN 140 and a plurality of DQNs 122, 124, 126. The generalist models 1432 may be used to recommend music in inference mode until the personalized models 1434 achieve a performance threshold, at which point the system (e.g. multi-model system 1100) may switch over to using the personalized models 1434 to recommend music to the user.

The generalist model training process 1450 begins by extracting subsets of music tracks from a music catalogue 1420 based on a curation process 1422 using the MIR data of the music tracks. The music catalogue 1420 may be an audio library 184 consisting of music tracks in some embodiments. The music tracks may be audio segments 230 in some embodiments. The MIR data associated with each music track may be stored as library MIR data 182 in the music catalogue 1420 in some embodiments; in other embodiments, the MIR data associated with a music track may be extracted from the music track, e.g. using a MIR extraction process 225.

Thus, in some embodiments the curation process 1422 requires a labelled dataset (i.e. audio library 184) describing the thematic MIR metadata associated with each track. For example, the music catalogue 1420 may include a set of jazz music from 1920s that is about love, and/or a set of rock music from the 1960s that has a generally calming energy. The curation process 1422 can be performed algorithmically using any of a number of known computational methods such as a supervised clustering algorithm.

The subsets of music tracks generated by the curation process 1422 are used by a Group by DQN process 1424 to generate groups of music tracks associated with each generalist Deep Q Network that is to be trained. The relationship between audio segments 230 having particular MIR features and a given DQN is described above with reference to FIG. 2A.

The generalist model training process 1450 also uses existing user data 1426 from an entire user population collected from listening devices 190, as described with reference to FIGS. 2A-2B above. The existing user data 1426 can include user profile data, records of users listening to music correlated with their affective responses, etc. A user grouping process 1428 may cluster or segment the existing user data 1426 to identify groups of types of users or user types. An example of user group or type identification is described in Feiyun Zhu, Jun Guo, Zheng Xu, Peng Liao, Junzhou Huang, "Group-driven Reinforcement Learning for Personalized mHealth Intervention", 2017, arXiv: 1708.04001, https://arxiv.org/abs/1708.04001, which is hereby incorporated by reference in its entirety.

A generalist model transfer learning process 1408 is used to train one or more sets of generalist models 1432. The generalist model transfer learning process 1408 may include an Affective Inference Neural Network (AINN) Generalist Model Training Process 1430 to train a generalist AINN 140 and a Deep Q Network (DQN) Generalist Model Training Process 1431 to train a set of generalist DQNs 122, 124, 126. Various transfer learning techniques are known in the field of machine learning. An example transfer learning process is described by Kieran Woodward and Eiman Kanjo and David J. Brown and T. M. McGinnity: "On-Device Transfer Learning for Personalising Psychological Stress Modelling using a Convolutional Neural Network", 2020, arXiv:2004.01603, https://arxiv.org/abs/2004.01603, which is hereby incorporated by reference in its entirety.

The AINN Generalist Model Training Process 1430 may use the AINNs 140 for users in the various user groups (i.e. the user groups output by the user grouping process 1428) to train the generalist AINN 140 of a set of Generalist Models 1432 using transfer learning. The DQN Generalist Model Training Process 1431 may use the generalist AINN 140 of the generalist models 1432 and the music tracks grouped by DQN output by the Group by DQN process 1424 to train the generalist DQNs 122, 124, 126 of a set of generalist models 1432 using transfer learning. For example, a particular group of users identified by the user grouping process 1428 may be associated with a particular generalist AINN 140 and the existing user data 1426 from those users may be used to train the given generalist AINN 140, whereas a particular subset of music tracks in combination with a user group may be associated with a particular generalist DQN, and the generalist AINN 140 for that user group may be used to train the given DQN.

The personalized model training process 1460 begins with a new user 1404 being added to the system 1100. The new user 1404 may be presented with a baselining process 1406 to initialize a user profile, for example using the user profile creation process described above with reference to FIG. 11. The baselining process 1406 may also elicit user input to assist in identifying the new user's 1404 musical preferences: for example, the new user 1404 may be prompted to fill out a baseline profile, and/or the system 1100 may have the new user 1404 listen to musical clips in rapid succession to understand the new user's 1404 tastes and/or behavioral responses to music.

A matching process 1410 is performed based on the music tastes, personality, user profile, and/or other information gathered during the baselining process 1406. The matching process 1410 can be done algorithmically in some embodiments using machine learning techniques or other ranking or matching algorithms. A set of generalist models (e.g. AINN 140 and DQNs 122, 124, 126) are selected, e.g. from database 1102, that are a good match to the new user 1404 based on the output of the baselining process 1406. A labelling process 1436 is used to facilitate the matching process by labelling the generalist models 1432 based on user groupings (from the user grouping process 1428) and music track subsets (from the Group by DQN process 1424). The label data used by the labelling process 1436 can be any kind of identifying vector. The matching process 1410 may match the new user 1404 with a particular user group based on the data (e.g. user profile data) output by the baselining process 1406, and a set of generalist models 1432 may be selected on the basis of the match and used to initially populate the models database 1402.

A set of personalized models 1430 is then generated for the new user 1404. Initially, the personalized models 1430 may be a copy of the generalist models 1432 selected for the new user 1404 based on the matching process 1410. However, as the personalized models 1430 are trained and thereby personalized using data from the new user 1404, they will improve in accuracy until they reach a performance threshold and are used by the system 100 for inference, as described above.

In a music selection process 1412, the new user 1404 manually creates subsets of music he or she would like the system 1100 to curate. The music selection process 1412 populates a user music catalogue 1414, for example, by allowing the new user 1404 to identify music tracks from a local or remote catalogue or library of music tracks.

A Group by DQN process 1416 of the personalized model training process 1460 operates similarly to the Group by DQN process 1424 of the generalist model training process 1450 described above. Subsets of music tracks from the user music catalogue 1414 are identified and used to group music tracks in association each Deep Q Network of the personalized models 1430 that is to be trained.

Data collected from the new user 1404 is used to train the personalized models 1430, in particular the AINN 140 of the personalized models 1430, after each user experience using a personalized model transfer learning process 1418, similar to the generalist model transfer learning process 1408 described above. The personalized model transfer learning process 1418 may also use the data gathered from the baselining process 1406. The factors used by the personalized model transfer learning process 1418 are described below with reference to FIG. 15.

A DQN Personalized Model Training Process 1417 operates similarly to the DQN Personalized Model Training Process 1417 described above to train the DQNs 122, 124, 126 of the personalized models 1430 using the personalized AINN 140 of the personalized models 1430.

Figure 15:
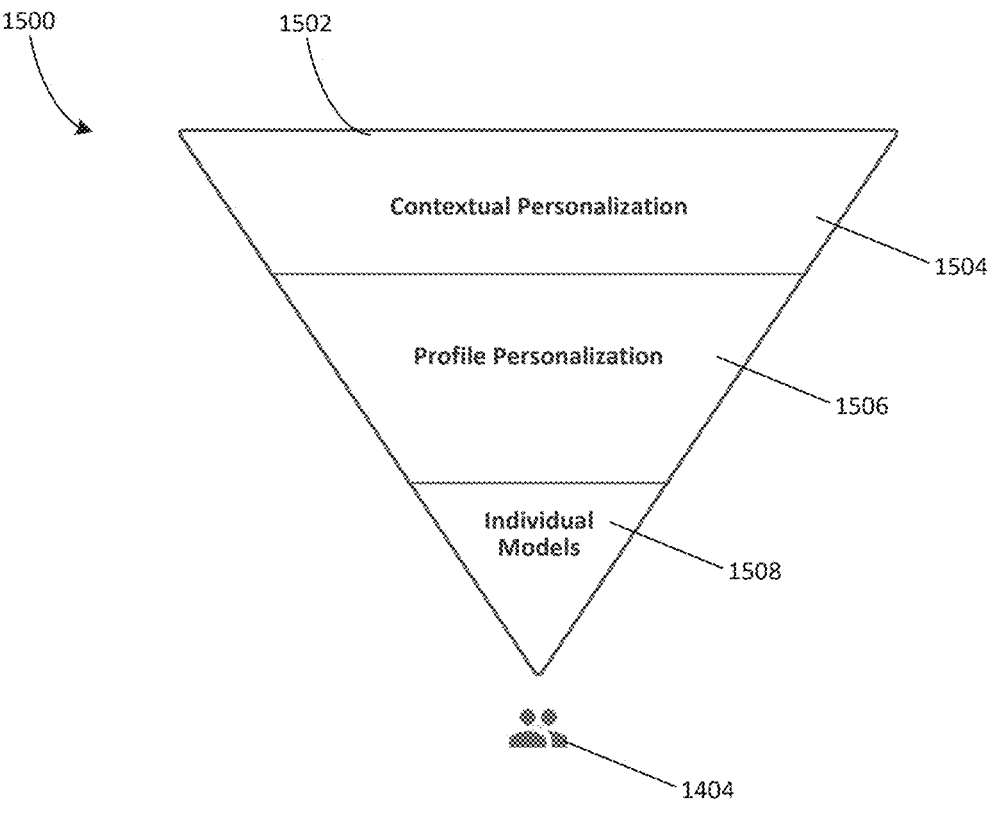
FIG. 15 is a schematic diagram showing personalization factors used by the personalized model transfer learning process of FIG. 14.

FIG. 15 shows personalization factors 1500 used by the personalized model transfer learning process 1418 of FIG. 14. The goal of the personalized model transfer learning process 1418 is to work from the top layer of the pyramid 1502, corresponding to contextual personalization 1504, through the middle layer of the pyramid 1502, corresponding to profile personalization 1506, until the bottom layer of the pyramid 1502 is reached, corresponding to individual models 1508 for each user (e.g. new user 1404).

Contextual personalization 1504 may include personalization of models (e.g. AINN 140 and DQNs 122, 124, 126) based on an initial state (e.g. user's affective state), a user's current expressed music preference, or other environmental variables (e.g. the time of day). Contextual personalization 1504 may thus correspond to factors taken into account in conventional music recommendation systems. Profile personalization 1506 may include personalization of models based on a user's personality, demographic membership, baseline music taste profile, and other general user traits. In some embodiments, profile personalization 1506 may be based on the user's membership within a user group determined by the user grouping process 1428. Individual models 1508 are individual personalized models trained using a particular user's affective responses to accurately infer that specific user's affective response to music, as described above e.g. in reference to FIGS. 2A-2B.

Thus, a hierarchy of personalized models 1430 may be selected and trained using the models database generation process 1400, ranging from slightly personalized using contextual personalization 1504, to more specifically personalized using profile personalization 1506, to very specifically personalized using individual models 1508.

Individual elements of the systems described herein may also be used for applications other than affective music recommendation. The affective inference neural network 140 may be used in the fields of music analytics, marketing, or insights, allowing new content to be evaluated based on its predicted affective impact. For example, the inputs and outputs of the affective inference neural network 140 could be switched, providing a sequence of MIR features that have a likelihood of inducing a target mood state given a certain user profile. The data generated by the various systems described herein may be useful for various purposes within the music industry, such as providing new insights around how the human psyche reacts to music, which can be further classified by demographic groups, user profile groups, and various taste profiles. With enough data, the affective inference capabilities of the systems described herein may be able to create new metadata about music compositions, increasing certainty for functional applications (e.g., film syncing, music therapy, etc.)

Examples of methods, systems, and non-transitory media for affective music composition will now be described with reference to FIGS. 16-30. The described music composition systems can be used at one or more stages of the music composition process to generate a MIR blueprint, a score, a composition lead sheet, a production lead sheet, a mix, and/or a master of a song intended to induce an affective state change in a listener. Various components described above in the context of affective music recommendation, such as affective inference models (e.g. AINNs) and MIR extraction processes, may be used in various embodiments of the music composition systems described herein.

Figure 16:
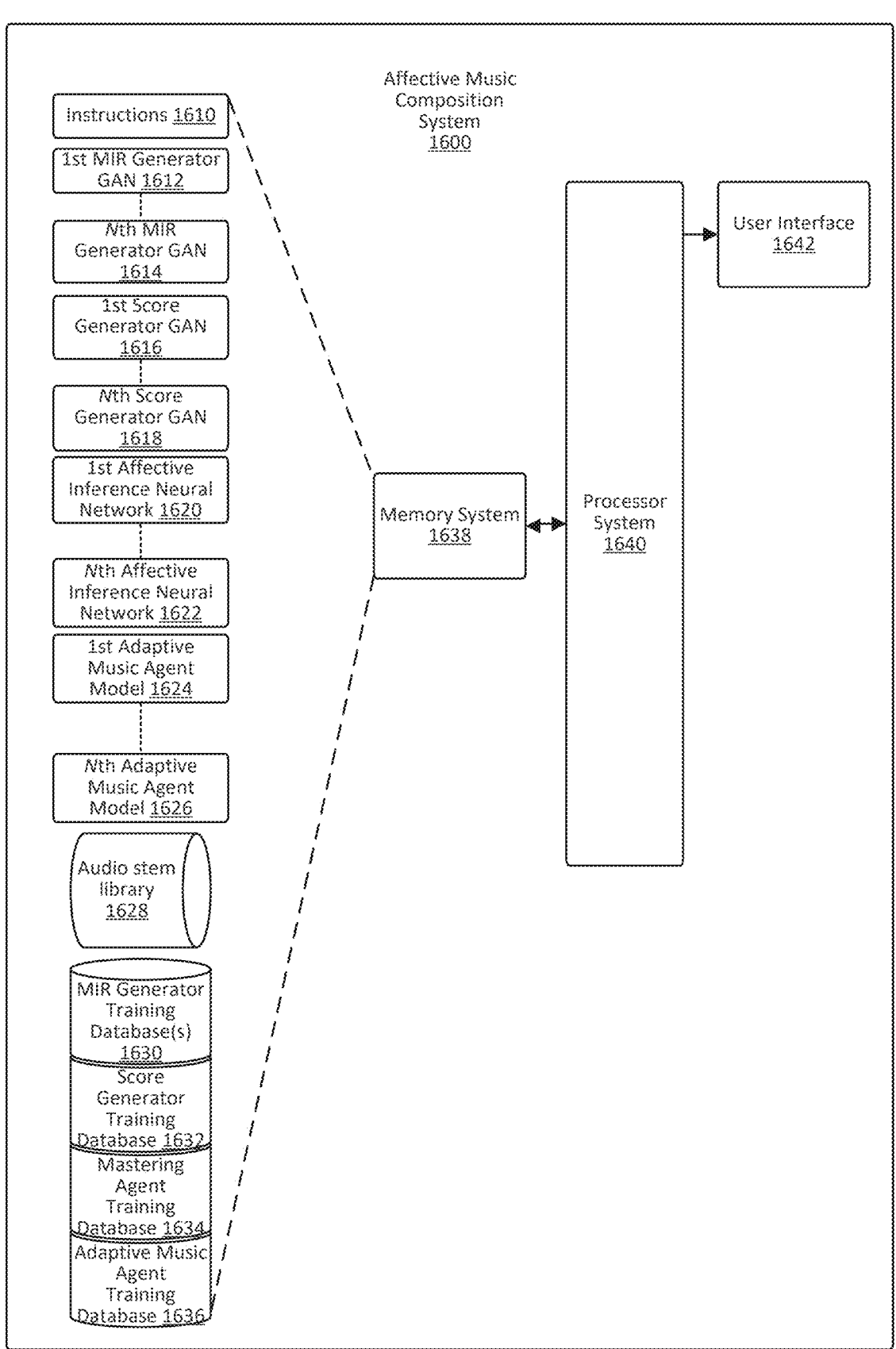
FIG. 16 is a block diagram of an example system for affective music composition according to example embodiments described herein.

FIG. 16 shows an example affective music composition system 1600. The affective music composition system 1600 may be implemented using a computing platform or system including hardware and software components much like the affective music recommendation system 100 of FIG. 1. The example shown here includes a memory system 1638 in communication with a processor system 1640, which is in turn in communication with a user interface 1642 used to interact with users.

The memory system 1638 stores the software and data used to implement the methods and processes for affective music composition described herein: software instructions 1610 executed by the processor system 1640 to implement the techniques described herein, including training and operation of the various models using machine learning techniques; a plurality of MIR generator generative adversarial networks (GANs) used to generate MIR data for different listener profiles, genres, and/or styles, shown as 1st MIR Generator GAN 1612 through Nth MIR Generator GAN 1614; a plurality of score generator GANs used to generate scores for different genres and/or styles, shown as 1st score Generator GAN 1616 through Nth score Generator GAN 1618; a plurality of affective inference models used to predict affective responses for different listener profiles, shown as 1st Affective Inference Neural Network 1620 through Nth Affective Inference Neural Network 1622; and a plurality of adaptive music agent models used to adapt an existing track or a library of audio stems 1628 to achieve a target affective state or trajectory for different listener profiles, genres, and/or styles, shown as 1st Adaptive Music Agent Model 1624 through Nth Adaptive Music Agent Model 1626. It will be appreciated that, whereas each set of models is shown as including N models, the value of N may be different for each set.

The memory system 1638 also stores data including an audio stem library 1628, one or more MIR generator training database(s) 1630, a score generator training database 1632, a mastering agent training database 1634, and an adaptive music agent training database 1636.

The relationships between the various software and data components of the affective music composition system 1600, and their interaction with users via the user interface 1642, are described below with reference to FIGS. 17A-D. The operation of the various subsystems shown in FIGS. 17A-D are then described with reference to FIGS. 18-26.

Figure 17A:
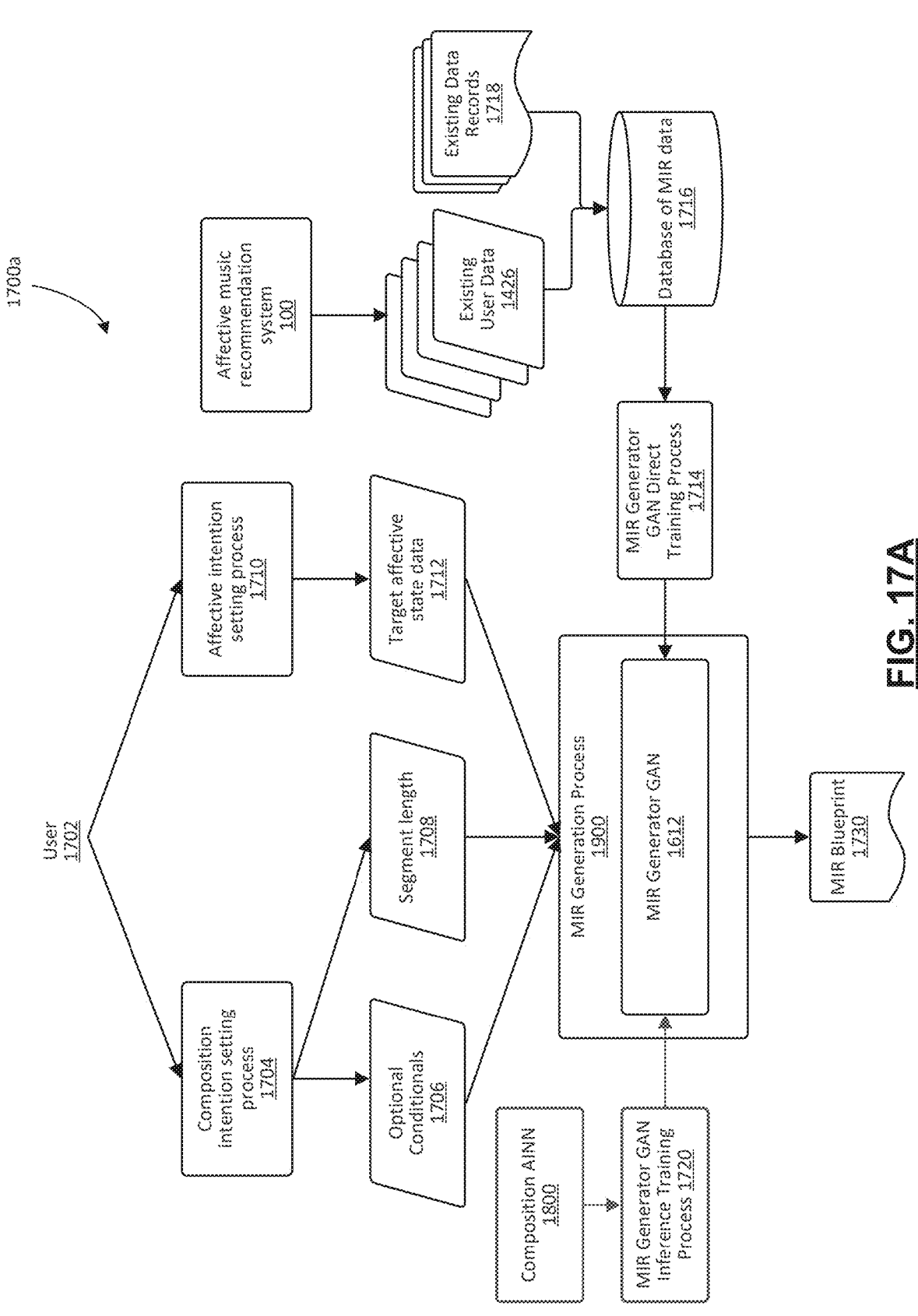
FIG. 17A is a block diagram showing the relationship between processes of a first portion of the example affective music composition system of FIG. 16.

FIG. 17A shows the relationship between processes of a first portion 1700a of the example affective music composition system 1600 of FIG. 16, including a MIR generator process 1900. The MIR generator process 1900 is used to generate a MIR blueprint for an audio segment (e.g., a song) that is intended to induce a specific affective response in listeners. The MIR blueprint generated by the MIR generator process 1900 typically identifies MIR features of the song as a whole, as well as MIR features of each of multiple epochs (i.e., temporal sub-segments) of the audio segment, that will induce the desired affective response. A user 1702 (who could be an artist, producer, or other user involved in music composition or production), interacts with the system 1600 via the user interface 1642. The user 1702 may interact with a composition intention setting process 1704, which informs various subsystems of the system 1600 described below regarding desired characteristics of the musical data to be generated during the composition process. A MIR generator process 1900, shown in FIG. 17A, may be managed by providing information such as: does the user 1702 want to make a full audio segment 230 (e.g. music track) or just a stem (i.e. a group of similar sound sources, such as the string instruments component or lead vocals component of a song)? How long does the user 1702 want the music track or stem to be? The composition intention setting process 1704 determines optional conditionals 1706 used to optionally constrain MIR generation, such as a specified key, tempo, and/or song structure. The composition intention setting process 1704 also determines the segment length 1708 (e.g. the length of the music track or stem).

The user 1702 may also interact with an affective intention setting process 1710, which informs various subsystems of the system 1600 described below regarding desired affective states or trajectories to be induced in listeners of the musical data to be generated during the composition process. The affective intention setting process 1710 may generate target affective state data 1712 indicating how the user 1702 wants listeners to feel after listening to the music generated during the composition process.

The optional conditionals 1706, segment length 1708, and target affective state data 1712 are used as inputs to a MIR generation process 1900, described in greater detail below with reference to FIG. 19.

The MIR generator process 1900 includes a MIR generator GAN, shown here as 1$^{st}$ MIR generator GAN 1612. In some embodiments, the MIR generator process 1900 is implemented as a conditional GAN with a control network; the optional conditionals 1706, segment length 1708, and target affective state data 1712 are used as conditional inputs to the MIR generation GAN 1612. The target affective state data 1712 may also be used as an input to the control network, as described in greater detail below.

The MIR generator GAN 1612 is trained by a MIR generator GAN direct training process 1714, using as training data a database of MIR data 1716 labelled with affective state data and, optionally, other conditionals. The database of MIR data 1716 may be populated or otherwise generated by using various data sources, such as the existing user data 1426 collected from the listening devices 190 of a population of users (as described above with reference to FIG. 14), and/or existing data records 1718 associating MIR data with affective responses and/or other conditional data (e.g., optional conditionals 1706 such as key, tempo, and/or song structure). In some embodiments, the existing user data 1426 may be collected using the affective music recommendation system 100 as described above.

The MIR generator GAN 1612 is also trained by a MIR generator GAN inference training process 1720, using a composition AINN 1800 as described below with reference to FIG. 18.

The MIR generator process 1900 generates a MIR blueprint 1730, which may include a mel-frequency cepstrum (MFC) spectrogram in some embodiments, potentially along with other MIR features. The MIR blueprint 1730 may be used by other components of the affective music composition system 1600 to assist in generating the music data (e.g., score, track, or stem).

Figure 18:
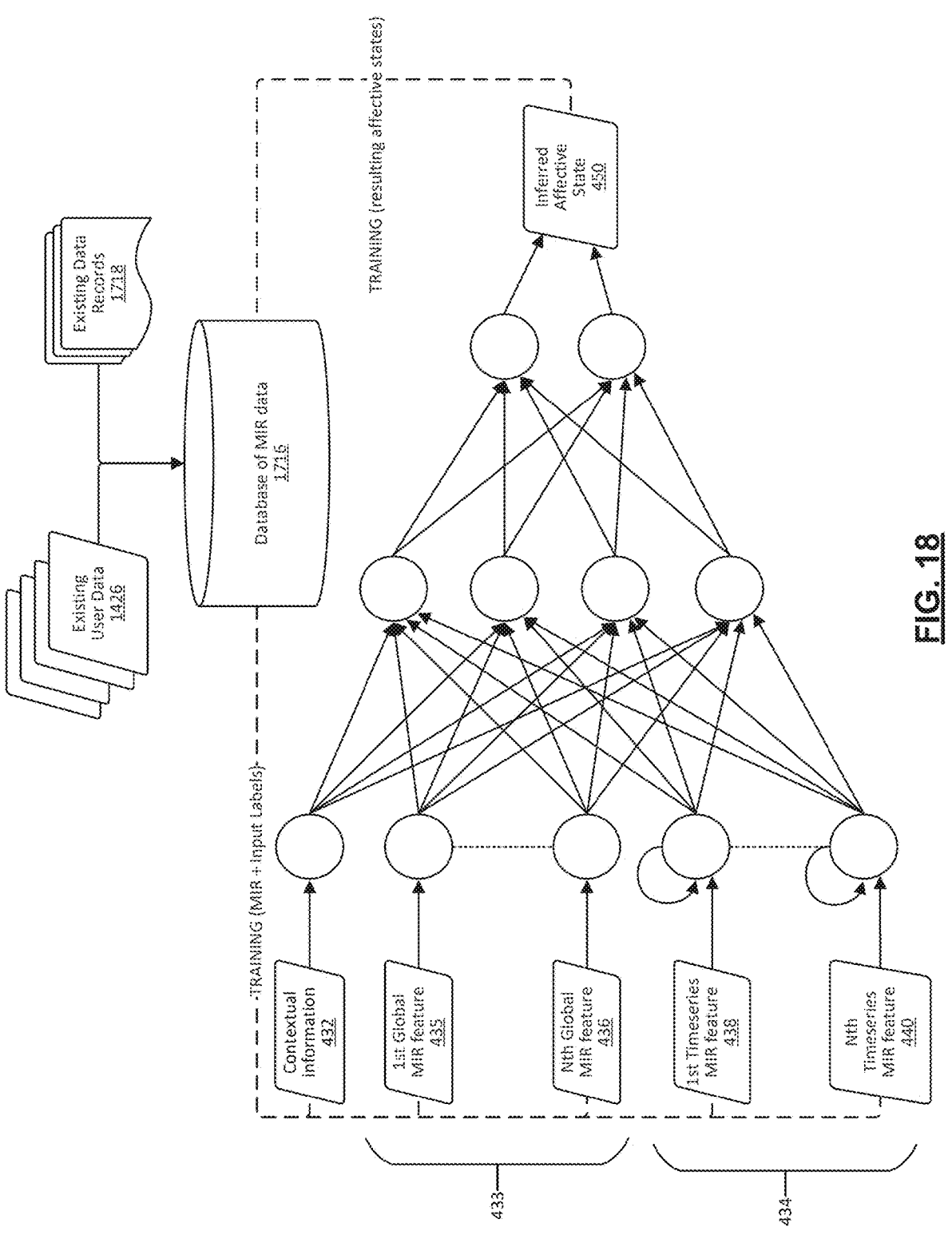
FIG. 18 is a schematic diagram showing a simplified recurrent neural network for affective state inference used by the affective music composition system of FIG. 16.

FIG. 18 shows a simplified recurrent neural network representing a composition AINN 1800 used by the affective music composition system 1600. The composition AINN 1800 operates much like the AINN 140 described above with reference to FIG. 4B. However, instead of using an individual user's current affective state 212 as an input, the composition AINN 1800 is instead trained using training data from the database of MIR data 1716 including MIR data labelled with affective response data, as well as contextual information 432 associated with the MIR data. Thus, the composition AINN 1800 operates in inference mode to predict affective responses of a generic user to a set of MIR features (including global MIR features 433 as well as a time series of epoch-specific MIR features 434) regardless of the user's current affective state.

Figure 19:
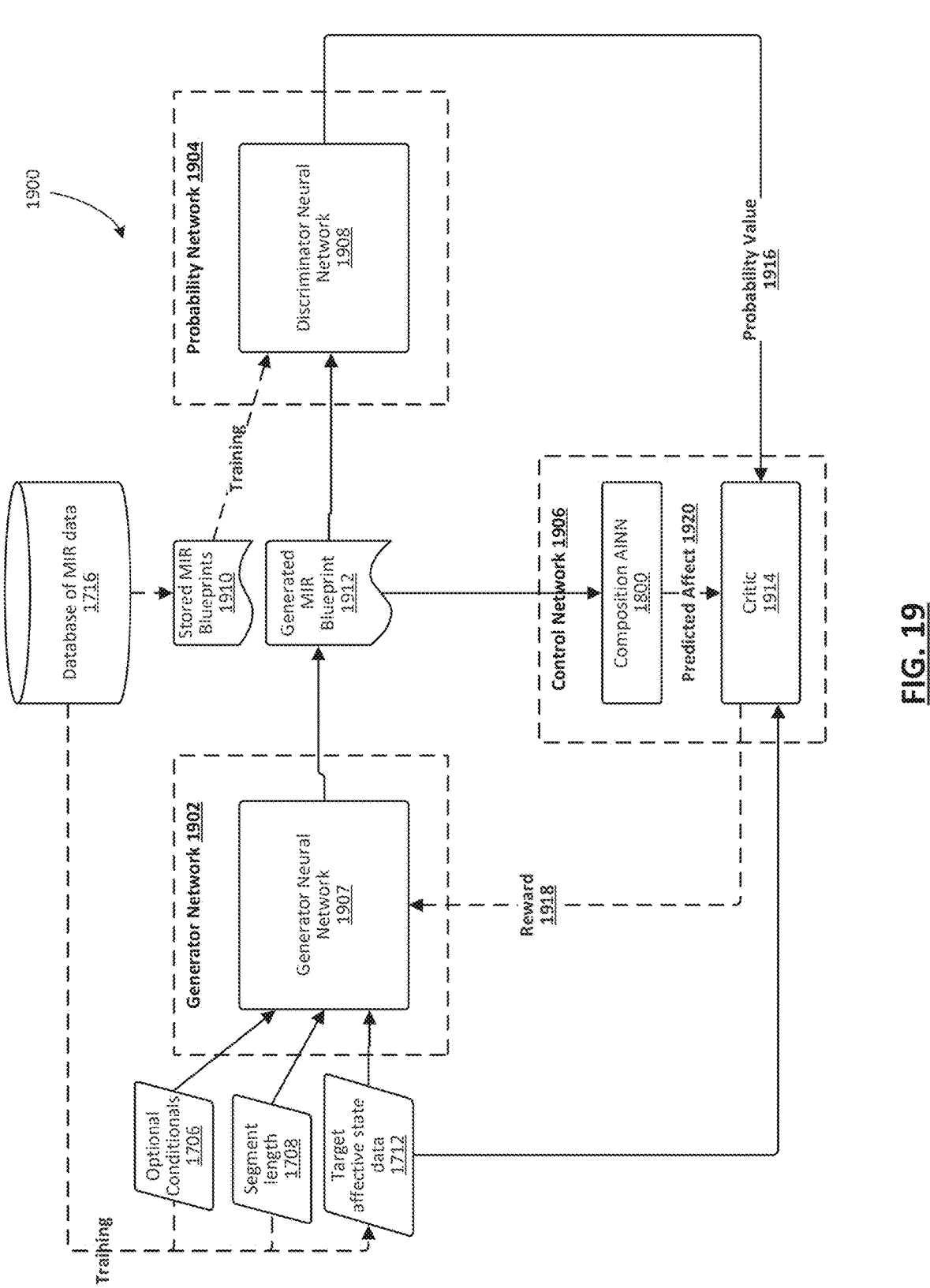
FIG. 19 is a block diagram showing a MIR generator process used by the affective music composition system of FIG. 16.

FIG. 19 shows an example MIR generator process 1900 used by the affective music composition system 1600. The MIR generator process 1900 may be structured as a MIR generator GAN (consisting of generator network 1902 and probability network 1904) with a control network 1906, as described in Cong Jin, Yun Tie, Yong Bai, Xin Lv, Shouxun Liu, "A Style-Specific Music Composition Neural Network", 9 Jun. 2020, Neural Processing Letters (2020) 52:1893-1912, https://doi.org/10.1007/s11063-020-10241-8 (hereinafter "Jin"), which is hereby incorporated by reference in its entirety. The MIR generator GAN itself, and in particular generator network 1902, may be structured as a conditional GAN, as described in Yi Yu, Simon Canales, "Conditional LSTM-GAN for Melody Generation from Lyrics", 2019, arXiv:1908.05551, https://arxiv.org/abs/1908.05551, which is hereby incorporated by reference in its entirety. The generator network 1902 comprises a generator neural network 1907, and the probability network 1904 comprises a discriminator neural network 1908; each neural network 1907, 1908 may be a recurrent neural network (RNN) with long short-term memory (LSTM), a convolutional neural network, a standard multi-layered perceptron neural network, or some other type of neural network or machine learning model. The functionality of the MIR generation process 1900 can also be achieved by other generative deep learning modalities like variational autoencoders (VAE) or simply a recurrent neural network (RNN) on its own. The GAN model has been evaluated as an effective means to execute the needed functionality but additional, similar algorithms may also be effective, particularly as advances in machine learning occur.

The MIR generator process 1900 operates in a training mode having two training phases, or in a MIR blueprint generation mode. In a first training phase of the training mode, the discriminator neural network 1908 of the probability network 1904 is trained to recognize MIR blueprints using actual stored MIR blueprints 1910 from the database of MIR data 1716 (i.e., MIR blueprints corresponding to actual songs composed by human artists).

In the second training phase, the generative network 1902 receives optional conditionals 1706, segment length 1708, and target affective state data 1712 as inputs (i.e., conditionals) from the database of MIR data 1716. The generative network 1902 comprises a generative neural network 1907 configured to generate MIR blueprints (shown as generated MIR blueprint 1912). At the beginning of the training process, each generated MIR blueprint 1912 is essentially random data. However, the probability network 1904 is used to provide feedback to the generative network 1902, mediated by the control network 1906, to train the generative network 1902 to generate more and more plausible MIR blueprints. The discriminator neural network 1908 compares each generated MIR blueprint 1912 to actual stored MIR blueprints 1910 from the database of MIR data 1716. The result of this comparison is a probability value 1916 (e.g., a value from 0 to 1) indicating the inferential likelihood of the discriminator neural network 1908 as to whether the generated MIR blueprint 1912 is a MIR blueprint for an actual song.

The control network 1906 comprises an affective inference model (shown as composition AINN 1800) and a critic 1914 (as described in the Jin reference). The critic 1914 operates to constrain the generated MIR blueprints 1912 to those satisfying target affective criteria. Thus, in the second training phase, the critic 1914 receives three inputs: the probability value 1916 generated by the probability network 1904 based on the generated MIR blueprint 1912, a predicted affect 1920 (i.e., a predicted affective response of a listener to music matching a MIR blueprint) generated by the composition AINN 1800 based on the generated MIR blueprint 1912, and the target affective state data 1712 received from the database of MIR data 1716. The critic 1914 applies a reward function to the probability value 1916, the predicted affect 1920, and the target affective state data 1712 to generate a reward 1918 based on how plausible the generated MIR blueprint 1912 is and how likely it is to satisfy the target affective state data 1712. The reward 1918 is used as feedback to train the generator neural network 1907, thereby improving its ability to generate plausible generated MIR blueprints 1912 that satisfy the target affective state data 1712 specified by the reward function. The reward function of the critic 1914 is driven by an affective inference model, such as composition AINN 1800.

The generative network 1902 and probability network 1904, assisted by the control network 1906, thus jointly constitute a MIR generator GAN (such as 1$^{st}$ MIR generator GAN 1612). In MIR blueprint generation mode, the optional conditionals 1706, segment length 1708, and target affective state data 1712 are provided by the user 1702 via the composition intention setting process 1704 and affective intention setting process 1710 instead of being supplied by the database of MIR data 1716. The generator network 1902 is used to generate generated MIR blueprints 1912 (e.g. MIR blueprint 1730 of FIG. 17A) that match the target affective state data 1712.

Figure 17B:
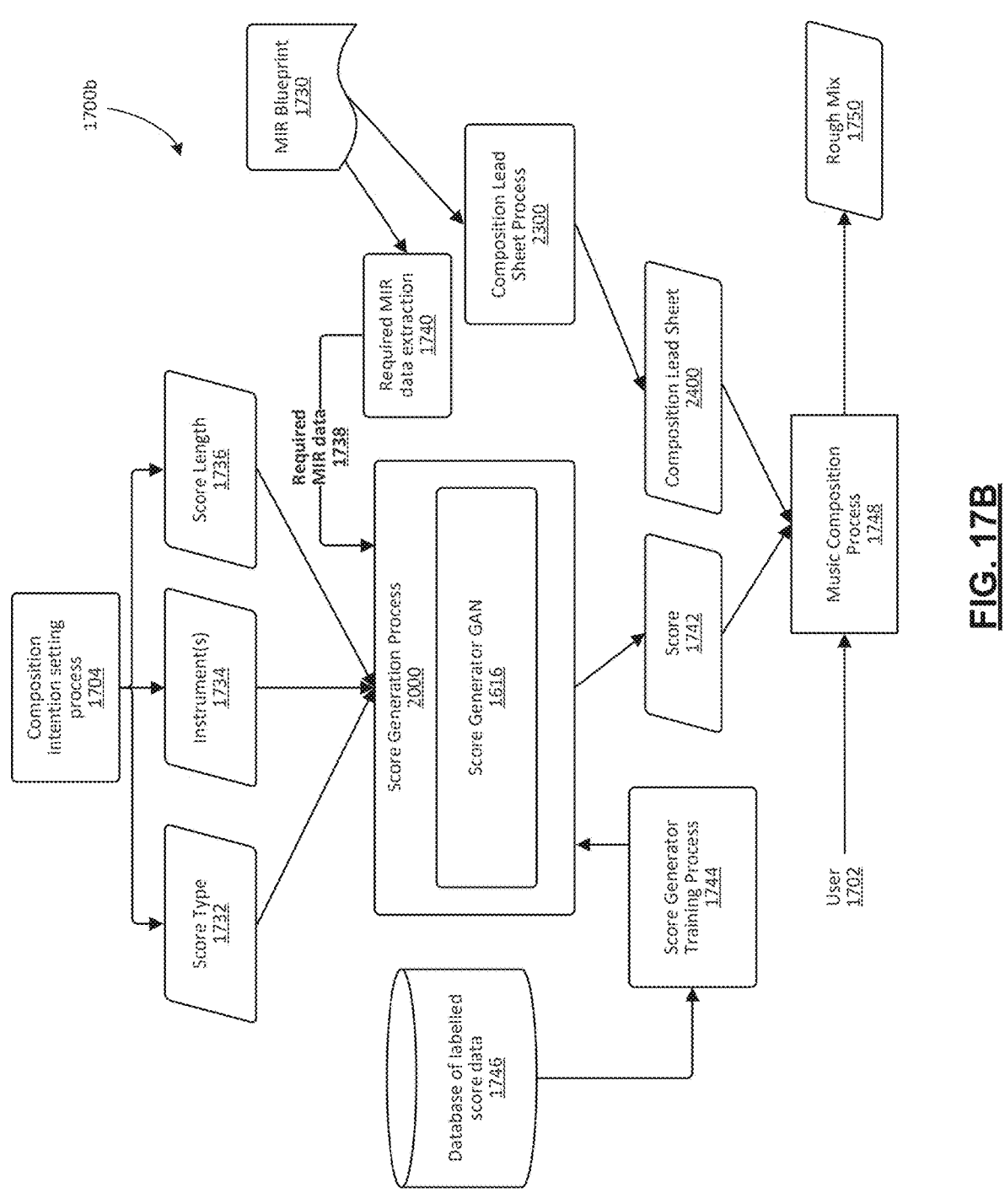
FIG. 17B is a block diagram showing the relationship between processes of a second portion of the example affective music composition system of FIG. 16.

FIG. 17B shows the relationship between processes of a second portion 1700b of the example affective music composition system 1600, including a score generator process 2000. Music composition refers to the writing of a piece of music, and the end result of composition is the generation of a score, i.e. a document identifying what notes should be played by which instruments at what times, and in what ways, to generate the audio characteristics of a song recording. As in FIG. 17A, the user 1702 may interact with the composition intention setting process 1704 to manage the score generator process 2000 by providing information such as: does the user 1702 want a harmonic progression, melody, rhythm, or full score? What instrument(s) does the user 1702 want? How long does the user 1702 want the score to be? The composition intention setting process 1704 thus determines the score type 1732, instruments 1734, and score length 1736. The score type 1732 may specify rhythm, harmonic progress, and/or melody.

A score generation process 2000 receives the score type 1732, instruments 1734, and score length 1736 as conditional inputs. The score generation process 2000 also receives a set of required MIR data 1738 for the score to be generated, which is used as a conditional input and/or input to a control network of the score generation process 2000. The set of required MIR data 1738 may be extracted from a MIR blueprint 1730 generated by the MIR generation process 1900 in some embodiments, or it may be extracted from another MIR blueprint or source of MIR data. In some embodiments, the set of required MIR data 1738 used by the score generation process 2000 may be only a portion of the MIR data contained in the MIR blueprint 1730; in other embodiments, it may include all MIR data contained in the MIR blueprint 1730.

The score generation process 2000 comprises a score generator GAN, shown here as 1$^{st}$ score generator GAN 1616. The score generation process 2000 operates on its inputs to generate as output a score 1742, such as a Musical Instrument Digital Interface (MIDI) score. The operations of the score generation process 2000 on its inputs to generate its outputs is described in greater detail below with reference to FIG. 20.

The score generation process 2000 is trained in a training mode by a score generator training process 1744, using labelled score data provided by a database of labelled score data 1746. The labelled score data may comprise human-composed scores labelled with MIR blueprints and/or other conditional inputs to be used in training the score generator process 200 and the score generator neural network thereof (e.g., 1$^{st}$ score generator neural network 1616).

Figure 20:
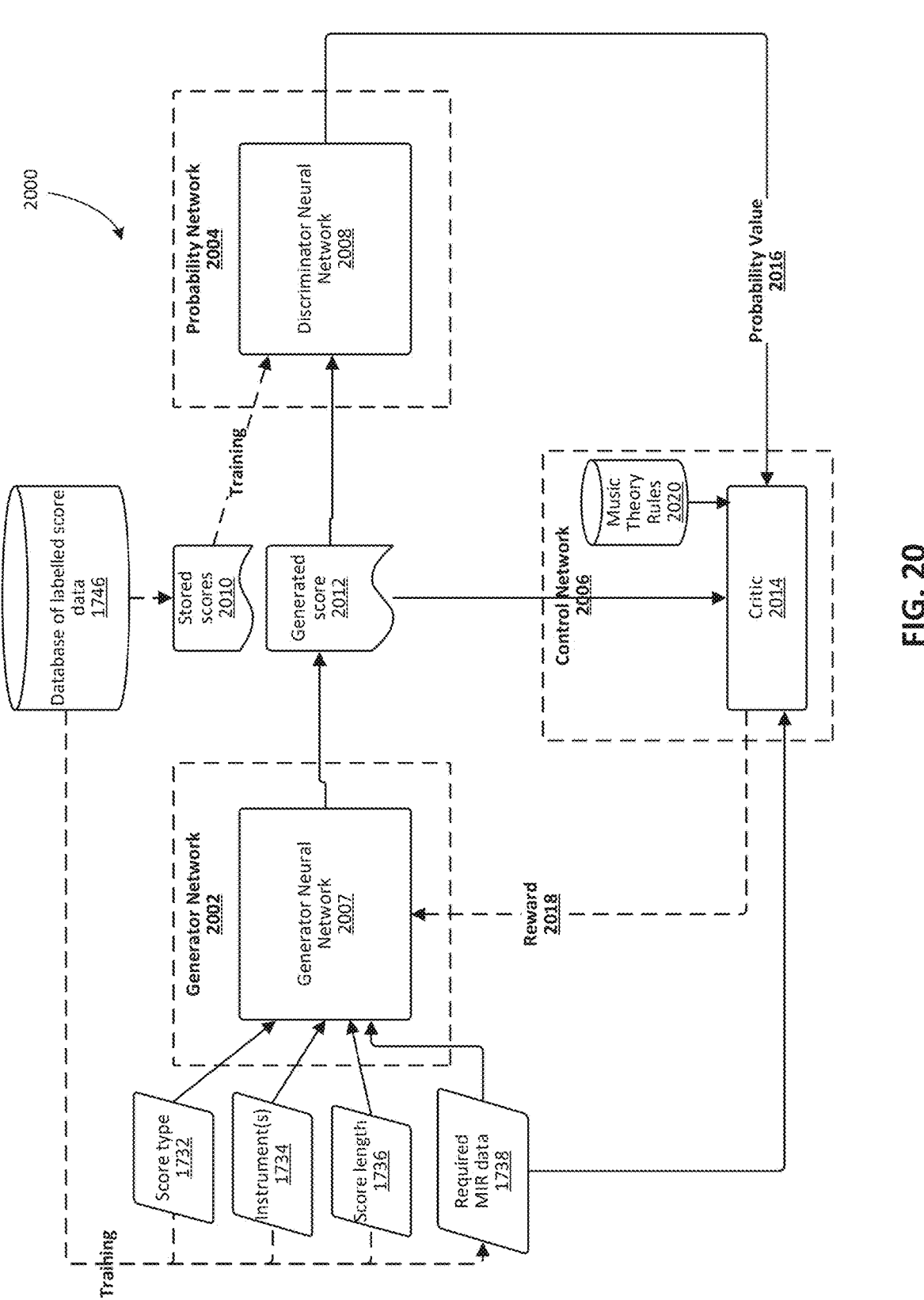
FIG. 20 is a block diagram showing a score generator process used by the affective music composition system of FIG. 16.

FIG. 20 shows an example score generator process 2000 described in reference to FIG. 17B above. The score generator process 2000 may be structured similarly to the MIR generator process 1900: a conditional GAN comprising a generator network 2002 and probability network 2004, with a control network 2006. The generator network 2002 comprises a generator neural network 2007, and the probability network 2004 comprises a discriminator neural network 2008; each neural network 2007, 2008 may be a recurrent neural network (RNN) with long short-term memory (LSTM), a convolutional neural network, a standard multi-layered perceptron neural network, or some other type of neural network or machine learning model. The functionality of the score generation process 2000 can also be achieved by other generative deep learning modalities like variational autoencoders (VAE) or simply a recurrent neural network (RNN) on its own. The GAN model has been evaluated as an effective means to execute the needed functionality but additional, similar algorithms may also be effective, particularly as advances in machine learning occur.

The score generator process 2000 operates in a training mode having two training phases, or in a score generation mode. In a first training phase of the training mode, the discriminator neural network 2008 of the probability network 2004 is trained to recognize scores using actual stored scores 2010 from the database of labelled score data 1746 (i.e., scores composed by human artists).

In the second training phase, the generative network 2002 receives optional required MIR data 1738, score length 1736, instrument(s) 1734, and score type 1732 as inputs (i.e., conditionals) from the database of labelled score data 1746. The generative network 2002 comprises a generative neural network 2007 configured to generate scores (shown as generated score 2012). At the beginning of the training process, each generated score 2012 is essentially random data. However, the probability network 2004 is used to provide feedback to the generative network 2002, mediated by the control network 2006, to train the generative network 2002 to generate more and more plausible scores. The discriminator neural network 2008 compares each generated score 2012 to actual stored scores 2010 from the database of labelled score data 1746. The result of this comparison is a probability value 2016 (e.g., a value from 0 to 1) indicating the inferential likelihood of the discriminator neural network 2008 as to whether the generated score 2012 is an actual score.

The control network 2006 comprises a critic 2014. The critic 2014 operates to constrain the generated scores 2012 to those satisfying a set of music theory rules 2020, which may be stored, e.g. as a database of music theory rules. Thus, in the second training phase, the critic 2014 receives three inputs: the probability value 2016 generated by the probability network 2004 based on the generated score 2012, the music theory rules 2020, and the required MIR data 1738 provided by the database of labelled score data 1746. The critic 2014 applies a reward function to the probability value 2016, the music theory rules 2020, and the required MIR data 1738 to generate a reward 2018 based on how plausible the generated score 2012 is, how likely it is to satisfy the music theory rules 2020, and how close the generated score 2012 is to matching a set of MIR data (i.e. the required MIR data 1738 provided by the database of labelled score data 1746). The reward 2018 is used as feedback to train the generator neural network 2007, thereby improving its ability to generate plausible generated scores 2012 that satisfy the music theory rules 2020 and match the required MIR data 1738.

The generative network 2002 and probability network 2004, assisted by the control network 2006, thus jointly constitute a score generator GAN (such as $1^{st}$ score generator GAN 1616). In score generation mode, the score length 1736, instrument(s) 1734, and score type 1732 are provided by the user 1702 via the composition intention setting process 1704, and the optional required MIR data 1738 is provided by the MIR blueprint 1730 via the required MIR data extraction process 1740, instead of being supplied by the database of MIR data 1716. The generator network 2002 is used to generate plausible generated scores 2012 (e.g. score 1742 of FIG. 17A) that match the MIR blueprint 1730 and obey the music theory rules 2020.

Returning to FIG. 17B, a score 1742 generated by the score generator process 2000 may be used as a score by human artists for subsequent music production processes. However, the score 1742 may also be used by subsequent processes of the affective music composition system 1600 to automate one or more of the subsequent steps of music production. In some embodiments, a user (e.g., the artist or producer who interacted with the system 1600 to generate the score 1742 or another user) may interact with a music composition process 1748 to generate a rough mix 1750 of the music track or stem based on the score 1742 and/or a composition lead sheet 2400. The composition lead sheet 2400 may be generated by a composition lead sheet process 2300 based on the MIR blueprint 1730. The composition lead sheet process 2300 is described in detail below with reference to FIG. 23, and an example composition lead sheet 2400 is described with reference to FIGS. 24A-B.

The user 1702 may interact with the music composition process 1748 through a user interface 1642 such as a digital audio workstation (DAW) or other audio workstation.

Figure 23:
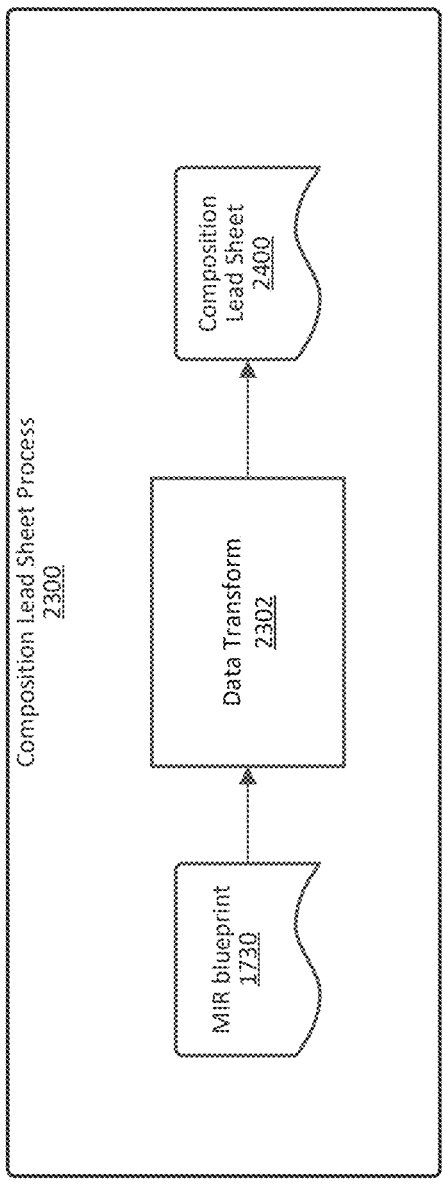
FIG. 23 is a block diagram showing a composition lead sheet process used by the affective music composition system of FIG. 16.

FIG. 23 shows a composition lead sheet process 2300 used by the affective music composition system 1600 of FIG. 16 and shown in FIG. 17B. The composition lead sheet process 2300 performs a data transform 2302 on the MIR blueprint 1730 to generate a composition lead sheet 2400.

Figure 24A:
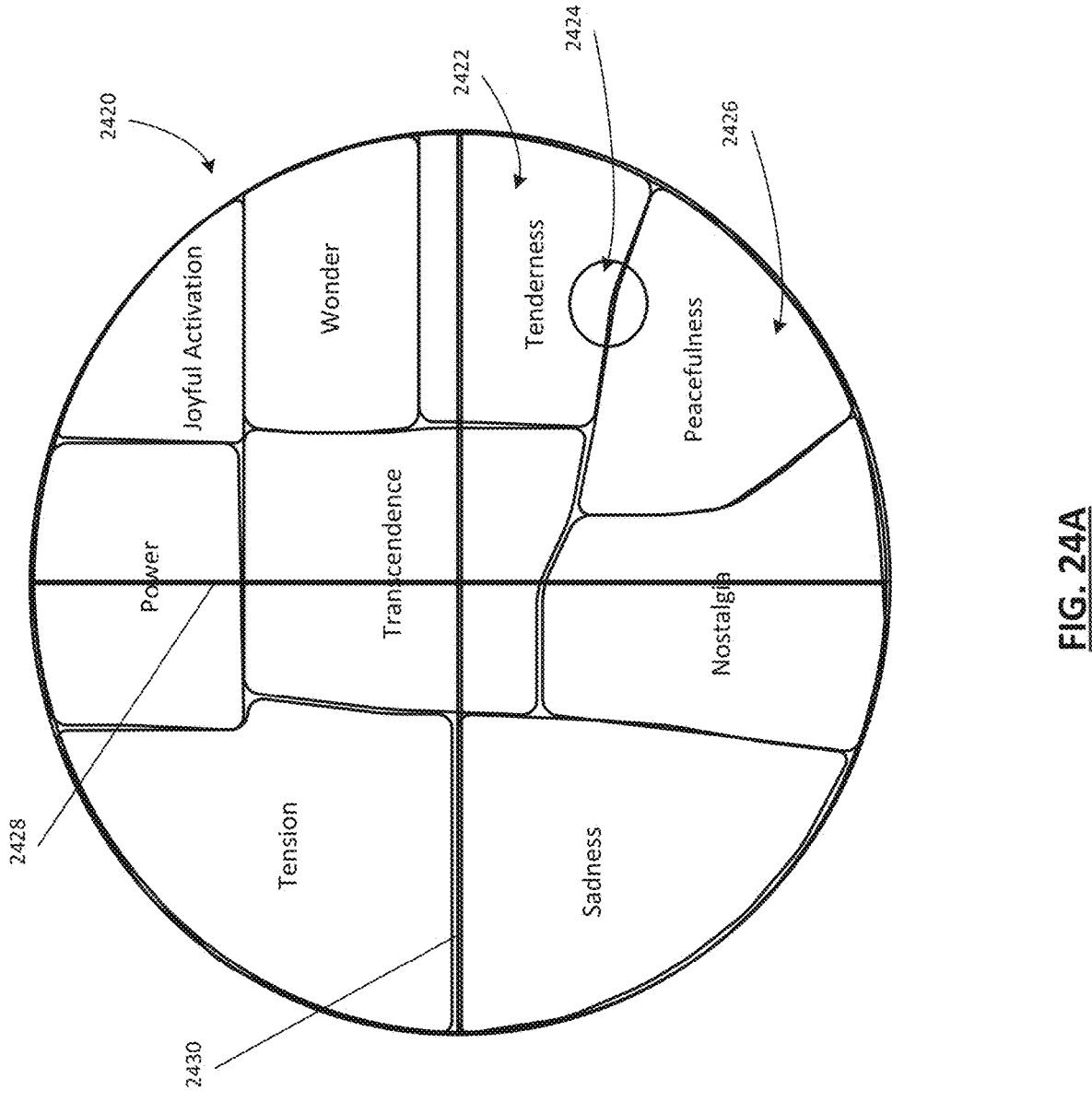
FIG. 24A is an example affective space indicator of a composition lead sheet generated by the composition lead sheet process of FIG. 23.

FIG. 24A is an example affective space indicator 2420 of a composition lead sheet generated by the composition lead sheet process of FIG. 23. The affective space indicator 2420 is similar to the 2-dimensional visual indicators of affective state used by the UI screens in FIGS. 6, 7, 10, and 12: it identifies an affective state 2424 of the composition lead sheet (based on the MIR blueprint 1730) situated within a 2-dimensional affective space wherein the horizontal axis

2430 is valence (positive to the right) and the vertical axis 2428 is activation (high to the top). A number of moods are shown as regions, such as tenderness 2422 and peacefulness 2426. In this example, the affective state 2424 of the composition lead sheet is situated between tenderness 2422 and peacefulness 2426, indicating very positive valence and slightly low activation.

Figure 24B:
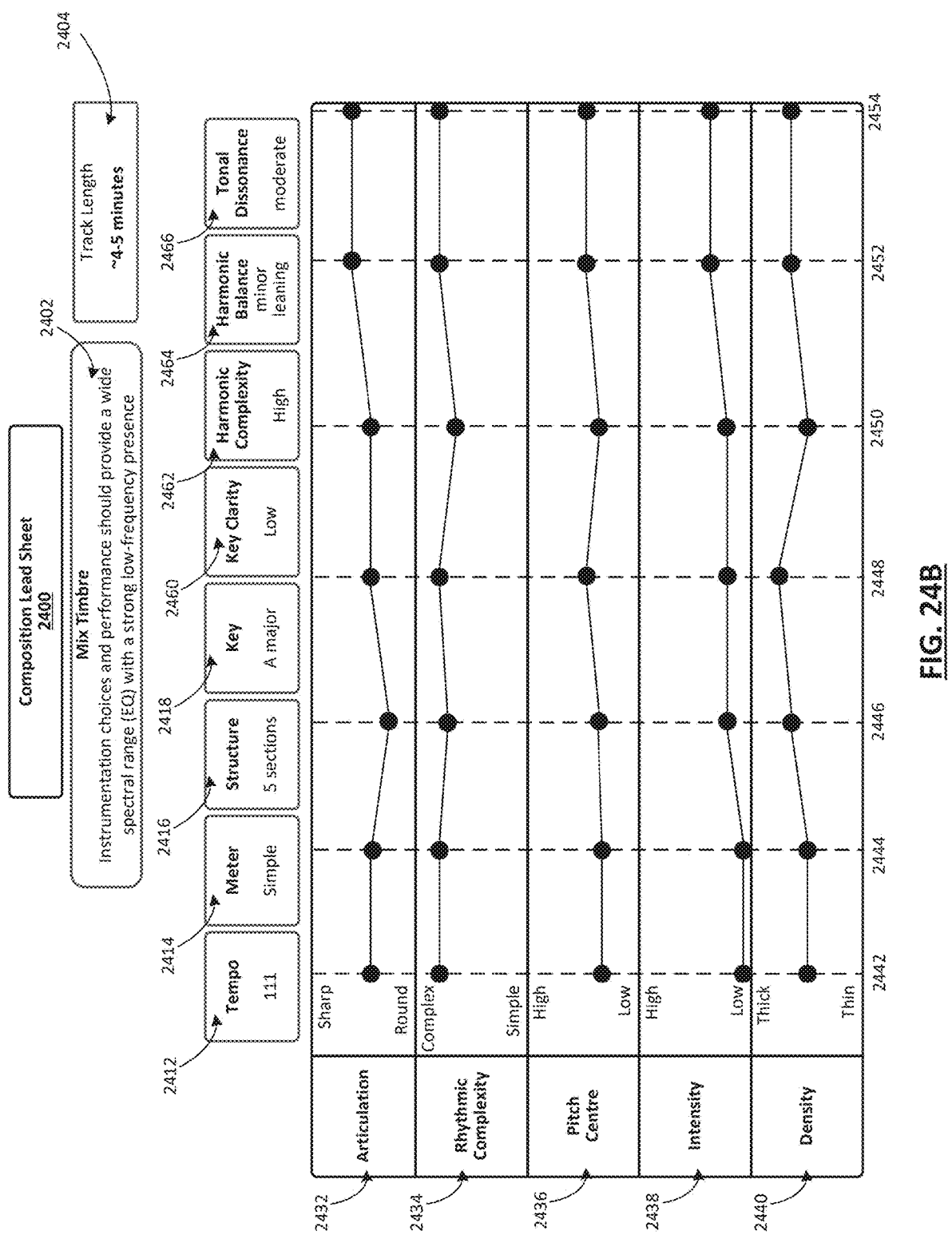
FIG. 24B is an example composition lead sheet generated by the composition lead sheet process of FIG. 23.

FIG. 24B shows an example composition lead sheet 2400 generated by the composition lead sheet process 2300 of FIG. 23. The composition lead sheet 2400 indicates various types of information relating to the composition process to be performed to produce the music segment (e.g. music track or stem).

Various fields indicate characteristics of the music segment as a whole. A Mix Timbre field 2402 provides information relating to the mix timbre, shown here as the text "Instrumentation choices and performance should provide a wide spectral range (EQ) with a strong low-frequency presence". A Tempo field 2412 provides information relating to the music segment length, shown here as the text "111". A Meter field 2414 provides information relating to the music segment length, shown here as the text "Simple". A Structure field 2416 provides information relating to the music segment length, shown here as the text "5 sections". A Key field 2418 provides information relating to the music segment length, shown here as the text "A major". A Key Clarity field 2460 provides information relating to the music segment length, shown here as the text "Low". A Harmonic Complexity field 2462 provides information relating to the music segment length, shown here as the text "High". A Harmonic Balance field 2464 provides information relating to the music segment length, shown here as the text "minor leaning". A Tonal Dissonance field 2466 provides information relating to the music segment length, shown here as the text "moderate".

Several time series of music segment data indicate various characteristics of the music segment at different time epochs 2442, 2444, 2446, 2448, 2450, 2452, 2454 or sub-segments within the music segment, from a first epoch 2442 through a seventh epoch 2454. A Rhythmic Complexity time series 2434 graphs the Rhythmic Complexity of each epoch between Complex (high) and Simple (low). A Pitch Centre time series 2436 graphs the Pitch Centre of each epoch between High (high) and Low (low). An Intensity time series 2438 graphs the Intensity of each epoch between High (high) and Low (low). A Density time series 2440 graphs the Density of each epoch between Thick (high) and Thin (low).

The composition lead sheet 2400 may also include an affective space indicator 2420 or other affective state data as described with reference to FIG. 24A.

Returning to FIG. 17B, the user 1702 interacting with the music composition process 1748 may rely upon the information provided in the composition lead sheet 2400 to guide the preparation of the rough mix 1750, either with or without the assistance of a score 1742. Alternatively, the user 1702 may rely upon the score 1742 on its own in preparing the rough mix 1750.

The rough mix 1750 may be further refined by subsequent operations of the system 1600, as described with reference to the third and fourth portions 1700c, 1700d of the system 1600 shown in FIGS. 17C-D.

Figure 17C:
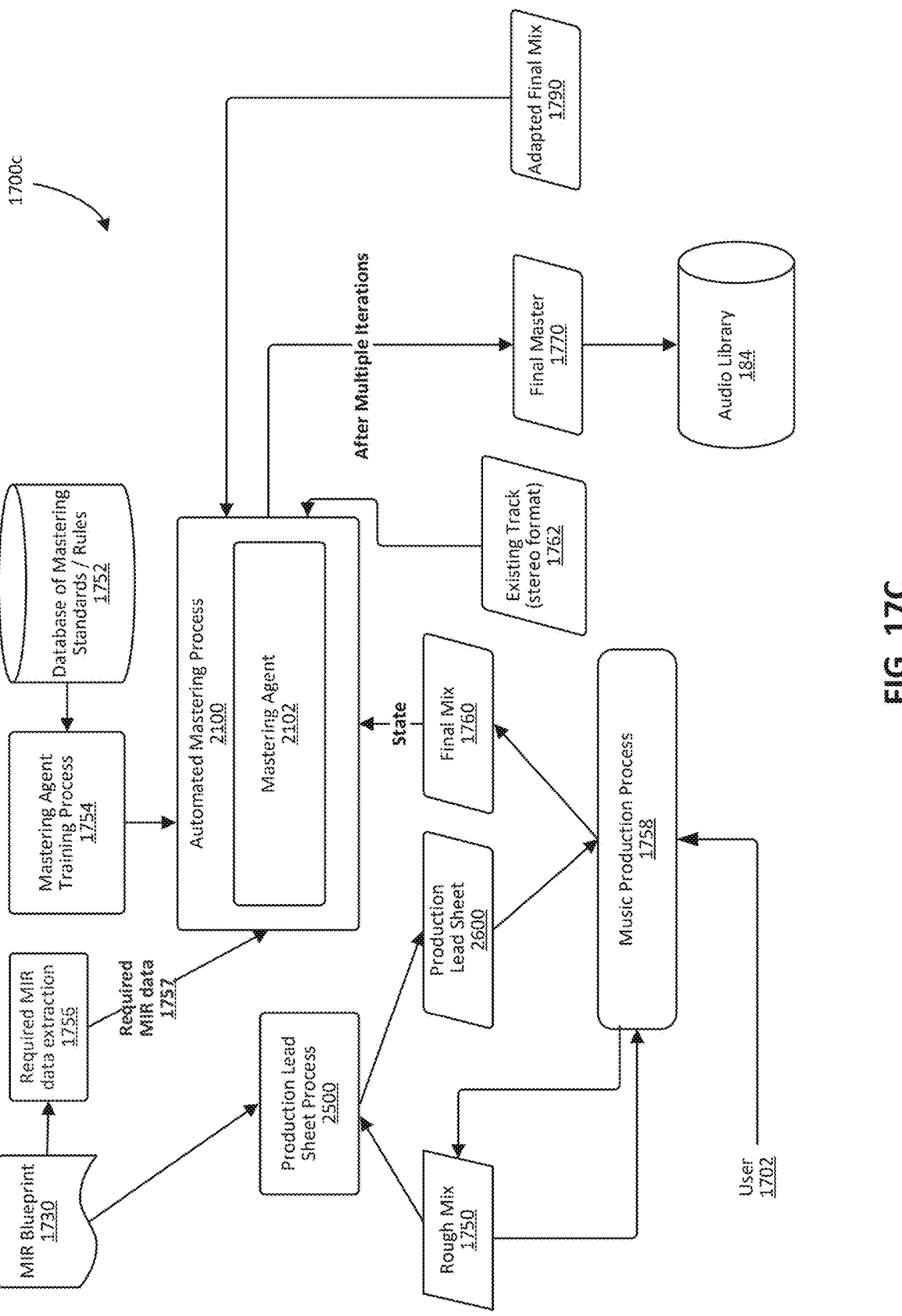
FIG. 17C is a block diagram showing the relationship between processes of a third portion of the example affective music composition system of FIG. 16.

FIG. 17C shows the relationship between processes of a third portion 1700c of the example affective music composition system 1600, including an automated mastering process 2100. Mastering refers to the setting of sound levels and other sound equalization settings of various instrumental tracks (i.e. stems) to generate a master recording (also called a master), i.e. a final, official recording of a song ready for presentation to an audience. The master is used as the source from which all later copies of the song are made. A user 1702—who may be the same user or a different user from the user 1702 interacting with the music composition process 1748, the composition intention setting process 1704, and/or the affective intention setting process 1710—interacts with a music production process 1758 to generate a rough mix 1750 or a final mix 1760. As with the music composition process 1748, the user 1702 may interact with the music production process 1758 through a user interface 1642 such as a digital audio workstation (DAW) or other audio workstation, and the user 1702 may be assisted by a production lead sheet 2600 (described below with reference to FIG. 26) and/or a pre-existing rough mix 1750 (such as a rough mix 1750 generated by the music composition process 1748).

A production lead sheet 2600 may be generated by a production lead sheet process 2500 (described below with reference to FIG. 25) based on a MIR blueprint 1730, such as the MIR blueprint 1730 generated in earlier portions 1700a, 1700b of the system 1600.

An automated mastering process 2100 may be used to automate the mastering stage of music production. The automated mastering process 2100 includes a mastering agent 2102, which may be implemented using a reinforcement learning model, as described in greater detail below with reference to FIGS. 21A-B. The automated mastering process 2100 may perform automated mastering on either the final mix 1760 generated by the music production process 1758, an existing track in stereo format 1762 (to re-master the existing track), or an adapted final mix 1790 (described with reference to FIG. 17D below). The automated mastering process 2100 may, over one or more iterations (described below), generate a final master 1770 based on its inputs, which may be saved in the audio library 184 as a final master music track (i.e., an audio segment). In some examples, the automated mastering process 2100 may be used mid-production: i.e., the user 1702 may interact with the music production process 1758 to cause the automated mastering process 2100 to perform one or more iterations of the mastering process on a human-composed song that has reached the mastering stage.

The mastering agent 2102 may be trained using a mastering agent training process 1754, which uses a database of mastering standards and/or rules 1752 to provide training data. The mastering agent training process 1754, and the operations of the automated mastering process 2100, are described in greater detail with reference to FIGS. 21A-B below.

As in the second portion 1700b of the system 1600, a required MIR data extraction process 1756 may be used to extract from the MIR blueprint 1730 those portions of the MIR data the required MIR data 1757 needed by the automated mastering process 2100 and provide the required MIR data 1757 thereto.

Figure 21A:
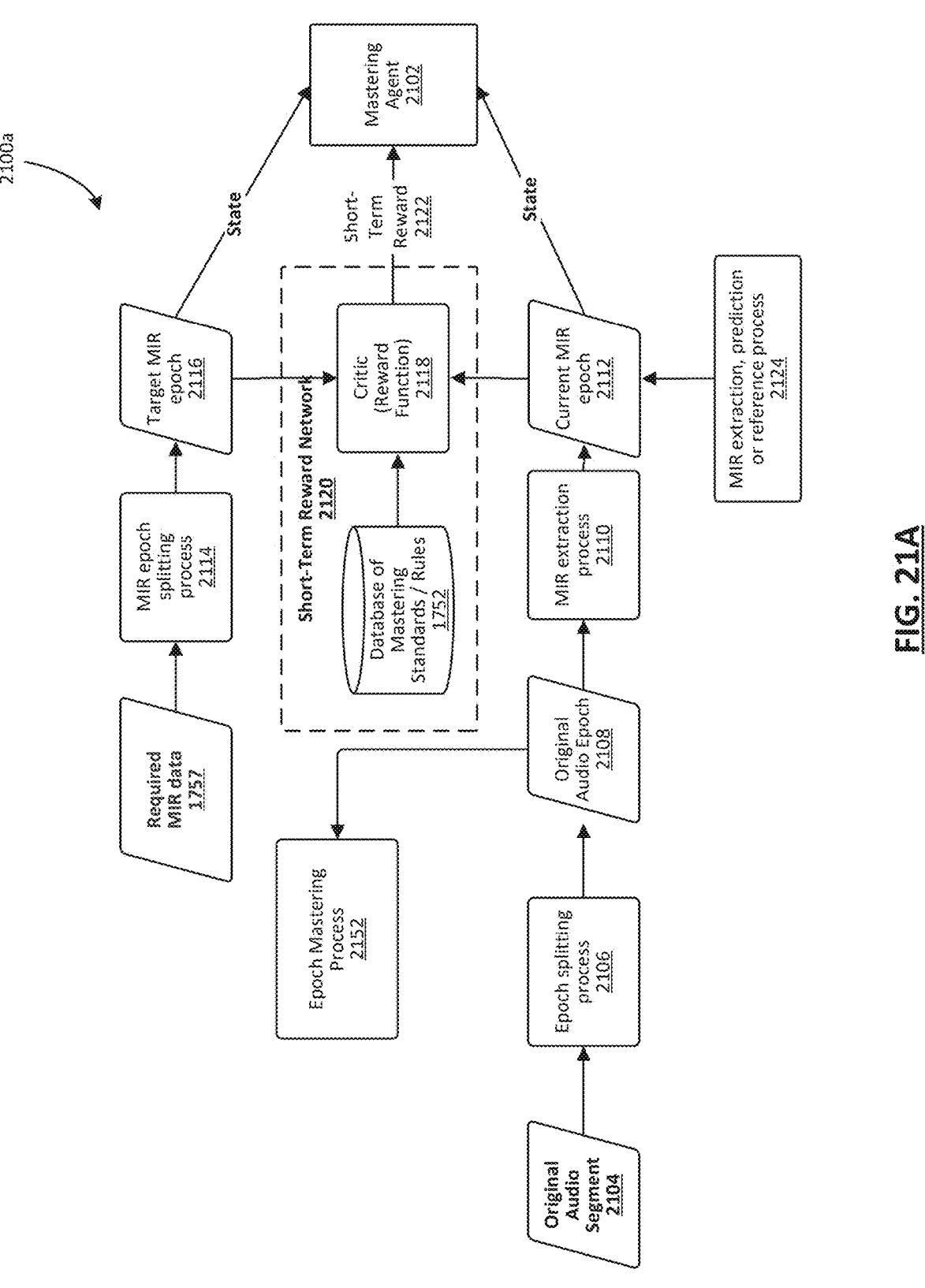
FIG. 21A is a block diagram showing a first portion of a mastering agent used by the affective music composition system of FIG. 16.

FIG. 21A is a block diagram showing a first portion 2100a of an automated mastering process 2100 used by the affective music composition system of FIG. 16. The automated mastering process 2100 operates over multiple iterations, also referred to herein as episodes. The original audio segment 2104 received as input (i.e., the final mix 1760, existing track in stereo format 1762, or adapted final mix 1790) is broken down into n epochs at an epoch splitting process 2106. Each original (pre-mastered) epoch 2108 is sent to an epoch mastering process 2152 for mastering one or more times (referred to as "passes" or "iterations"). In each pass, the epoch mastering process 2152 applies mastering actions (described below) to the epoch 2108 until the epoch 2108 satisfies a MIR target for that epoch. After the first epoch 2108 satisfies its respective MIR target, the mastering of the epoch 2108 is considered complete, and the next epoch 2108 undergoes the epoch mastering process 2152 one or more times until it satisfies its respective MIR target. This cycle continues until each epoch 2108 of the segment 2104 has been mastered.

MIR features are extracted from each original audio epoch 2108 by a MIR extraction process 2110, providing a reference for the starting (i.e. pre-mastering) MIR features of the epoch. The extracted MIR features are referred to as the current MIR epoch 2112. The current MIR epoch 2112 may also take into account additional MIR information generated by a MIR extraction, prediction, or reference process 2124 performed on the mastered audio epoch (described in greater detail with reference to FIG. 21B below). The MIR extraction, prediction, or reference process 2124 may extract MIR data via a tool like MIRtoolbox, reference MIR data from a table of previously extracted MIR features, or predict MIR data using a model that receives raw audio as input and outputs a MIR data prediction.

The MIR features needed by the automated mastering process 2100 are received as the required MIR data 1757. The required MIR data 1757 is broken down into epochs (i.e. time periods) of MIR data corresponding to the MIR features needed for each epoch of the mastered audio segment by a MIR epoch splitting process 2114. These epochs of MIR data are referred to as target MIR epochs 2116, indicating the MIR feature targets for the mastering process for a given epoch. The epoch sizes are synchronized between the epoch splitting process 2106 and MIR epoch splitting process 2114 in order to maintain the same timeline throughout the mastering process.

A short-term reward network 2120 is used to generate a short-term reward 2122 for training the mastering agent 2102. The short-term reward 2122 is used in the reinforcement learning process of training the mastering agent 2102. The short-term reward network 2120 comprises a critic 2118 that applies a reward function to three inputs: the target MIR epoch 2116 indicating the MIR feature desired in the current epoch; the current MIR epoch 2112, indicating the pre-mastered MIR features of the current epoch; and mastering standards and/or rules from the database of mastering standards and rules 1752. The reward function applied by the critic 2118 generates the short-term reward 2122 constrained by the mastering rules and/or standards, and based on whether or not the current MIR epoch 2112 satisfies the MIR features of the target MIR epoch 2116.

The short-term reward 2122 is provided as input to the mastering agent 2102, which may be implemented as a reinforcement learning agent such as a branching recurrent deep Q network (DQN). The branching recurrent DON may include LSTM to implement a memory of the mastering actions performed on each epoch. An example branching Q-learning network is described in Arash Tavakoli, Fabio Pardo, and Petar Kormushev, "Action Branching Architectures for Deep Reinforcement Learning", 2018, arXiv: 1711.08946, https://arxiv.org/abs/1711.08946, which is hereby incorporated by reference in its entirety. An example deep recurrent Q-learning network is described in Matthew Hausknecht and Peter Stone, "Deep Recurrent Q-Learning for Partially Observable MDPs", 2017, arXiv:1507.06527, https://arxiv.org/abs/1507.06527, which is hereby incorporated by reference in its entirety. Additional reinforcement learning algorithms that could be used for the automated mastering process 2100 are model-based actor critic algorithms, A3C algorithms or contextual multi-armed bandit algorithms. Branching deep q-networks paired with deep recurrent q-learning provides an effective algorithmic solution for this functionality.

Figure 21B:
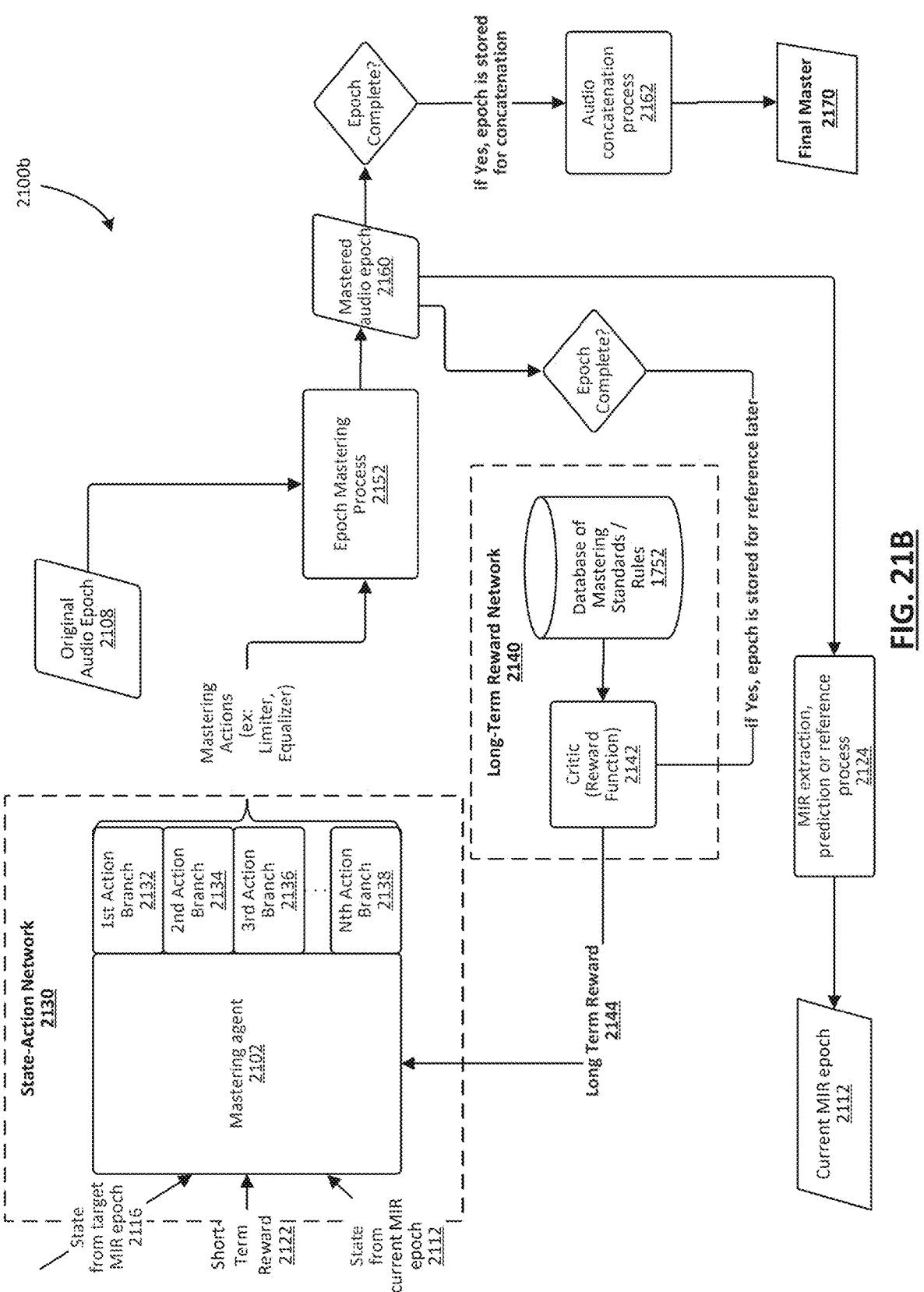
FIG. 21B is a block diagram showing a second portion of a mastering agent used by the affective music composition system of FIG. 16.

FIG. 21B is a block diagram showing a second portion 2100b of the automated mastering process 2100. The mastering agent 2102 is included in a state-action network 2130. The mastering agent 2102 is trained using the short-term reward 2122 as well as a long-term reward 2144 described below. The mastering agent 2102 also receives state data in the form of the target MIR epoch 2116 and the current MIR epoch 2112. By comparing the target MIR epoch 2116 to the current MIR epoch 2112, the mastering agent 2102 makes decisions about the appropriate parameter values to use for each of a plurality of mastering tools to apply to the current original audio epoch 2108 in the current mastering pass. The decisions regarding parameter values for each mastering tool are made by a respective action branch of the mastering agent 2102, shown as a $1^{st}$ action branch 2132, a $2^{nd}$ action branch 2134, a $3^{rd}$ action branch 2136, and so on through an nth action branch 2138, wherein n can be any positive integer. The mastering actions applied by the mastering tools may include mastering actions such as limiting and equalizing.

The epoch mastering process 2152 applies the mastering tool parameter values from each action branch 2132 . . . 2138 to the original audio epoch 2108 being mastered to perform a mastering pass, i.e. a pass of audio mastering. After the mastering pass has been performed, the resulting audio epoch is checked for completion of mastering. If the audio epoch is now considered fully mastered, the mastered epoch is stored for future reference and used as input to a critic 2142 of a long-term reward network 2140. The mastered epoch is also stored for concatenation with other mastered epochs for eventual concatenation by an audio concatenation process 2162 to generate the final master 2170, i.e. the final mastered song consisting of all the mastered epochs concatenated together. The mastered epoch is also provided to the MIR extraction, prediction or reference process 2124 for use in generating the current MIR epoch 2112 as described above.

The long-term reward network 2140 uses its critic 2142 to apply a reward function to one or more stored mastered epochs and mastering standards and/or rules data from the database of mastering standards and rules 1752 to generate a long-term reward 2144, indicating the extent to which multiple epochs over time are satisfying the mastering standards and/or rules.

Once the final master 2170 has been generated, it may be used by the other processes of the system 1600, e.g. by storing it in the audio library 184 as final master 1770.

Figure 25:
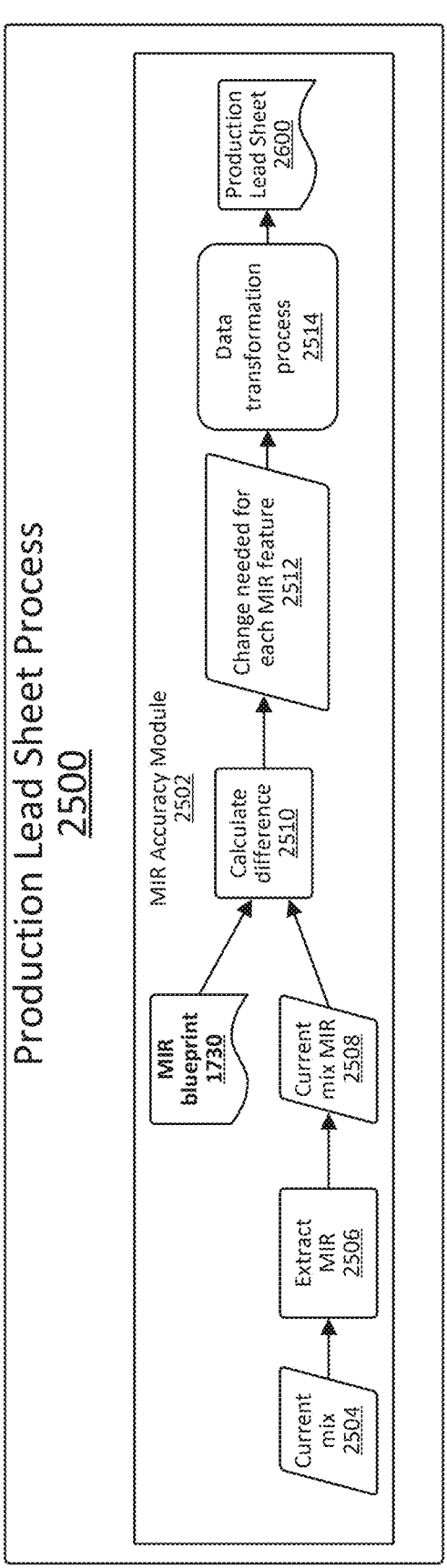
FIG. 25 is a block diagram showing a production lead sheet process used by the affective music composition system of FIG. 16.

FIG. 25 shows an example production lead sheet process 2500 used by the affective music composition system 1600 to generate a production lead sheet 2600, to be used by the music production process 1758. MIR data is extracted from the current mix 2504 received as input (e.g. rough mix 1750) by a MIR extraction process 2506 to generate the current mix MIR data 2508. The MIR blueprint 1730 is compared to the current mix MIR data 2508 an a difference between them is calculated by a difference calculation process 2510 to generate a set of changes needed 2512 for each MIR feature of the current mix MIR data 2508 to match the MIR blueprint 1730. A data transformation process 2514 is performed on the set of changes needed 2512 to generate a production lead sheet 2600. The production lead sheet 2600 may be used, e.g. by the music production process 1758, to direct the producer (i.e. the user 1702) in the producer's production decisions. This process 2500, performed by a MIR accuracy module 2502, may cycle through multiple iterations corresponding to multiple iterations of the automated mastering process 2100.

Figure 26:
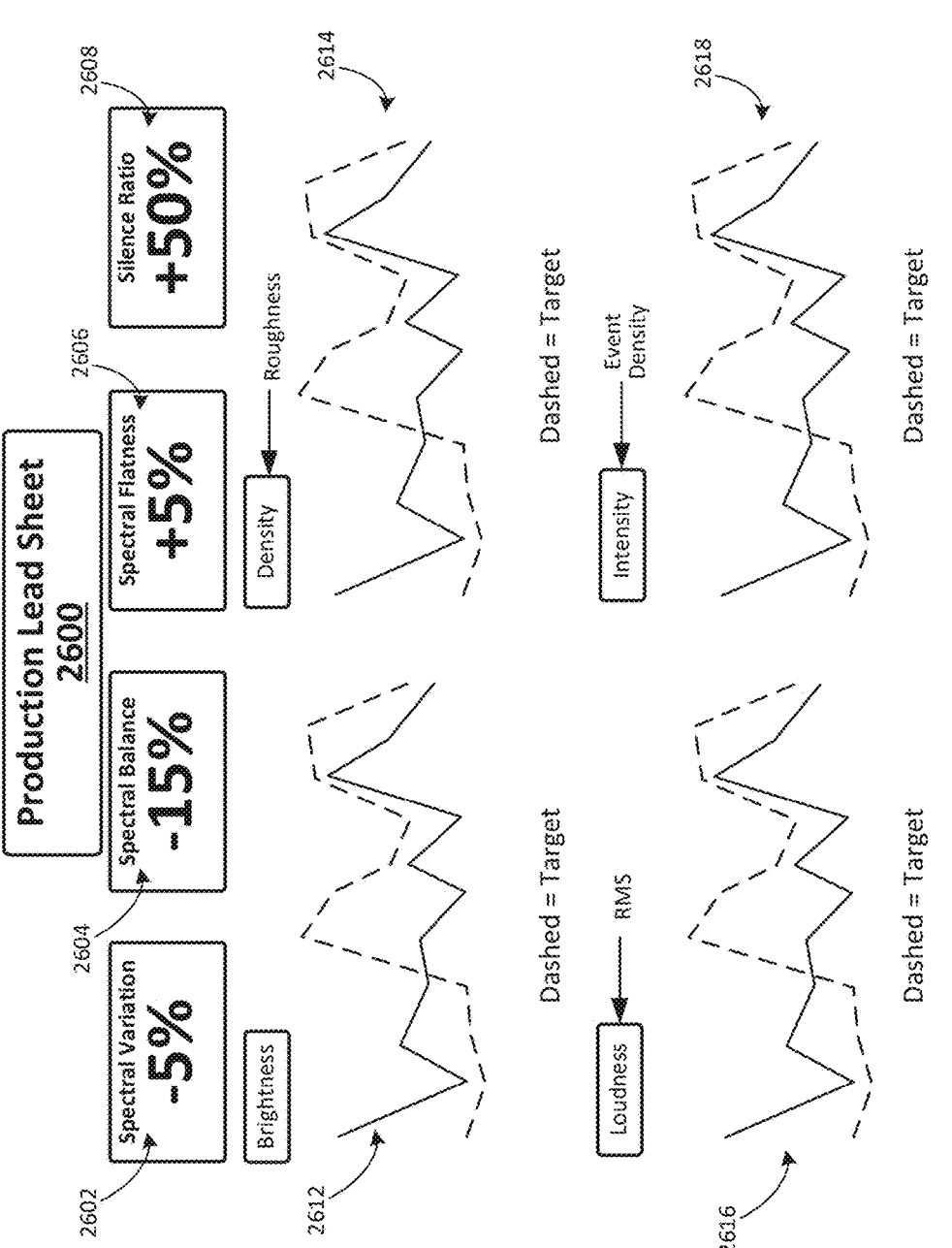
FIG. 26 is an example production lead sheet generated by the production lead sheet process of FIG. 25.

FIG. 26 shows an example production lead sheet 2600 generated by the production lead sheet process 2500. The production lead sheet 2600 includes several global fields indicating the set of changes needed 2512 in the overall MIR data for the audio segment, shown here as percentage changes needed in a spectral variation field 2602, a spectral balance field 2604, a spectral flatness field 2606, and a silence ratio field 2608. The production lead sheet 2600 also includes several time-series graphs indicating the set of changes needed 2512 in the per-epoch MIR data for each epoch of the audio segment, shown here as a brightness time-series graph 2612, a density time-series graph 2614 (indicating roughness), a loudness time-series graph 2616 (measured as root-mean-squared loudness difference), and an intensity time-series graph 2618 (indicating event density). Each graph 2612, 2614, 2616, 2618 shows the current MIR data of the epoch as a solid line and the MIR target (from the MIR blueprint 1730) as a dashed line, with epochs indicated chronologically from left to right. It will be appreciated that the illustrated example shows the same values for each graph for the sake of simplicity, but that an actual production lead sheet 2600 would likely have different time-series values for each graph.

The production lead sheet 2600 may also include an affective space indicator 2420 or other affective state data as described with reference to FIG. 24A.

Figure 17D:
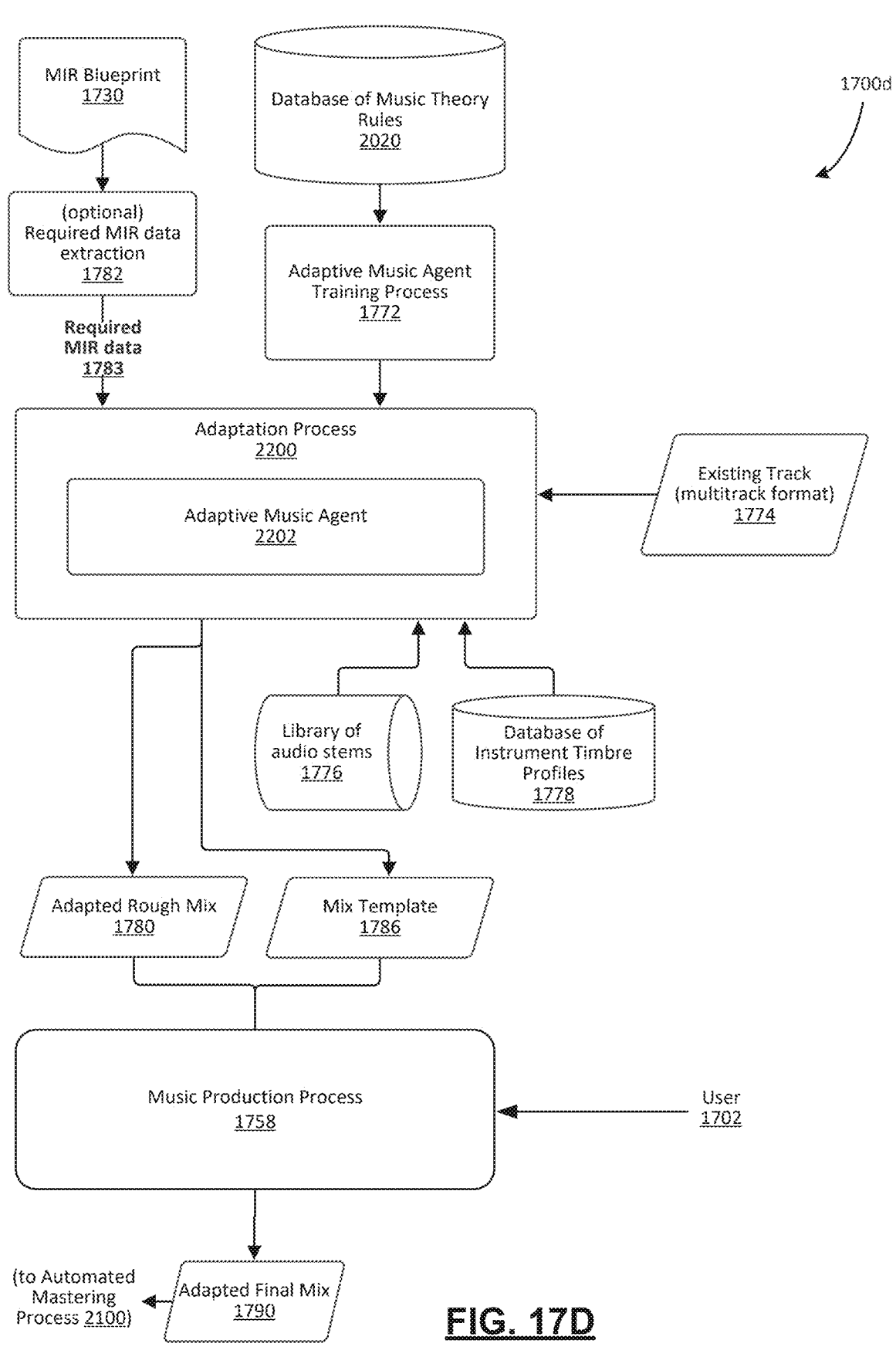
FIG. 17D is a block diagram showing the relationship between processes of a fourth portion of the example affective music composition system of FIG. 16.

FIG. 17D shows the relationship between processes of a fourth portion 1700d of the example affective music composition system 1600, including an adaptation process 2200. Adaptation refers to a process by which a musical composition is arranged for performance with instruments or voices differing from those originally specified. Thus, adaptation may take an existing mix, recording, or composition as input and generate as output a new mix that replaces one or more of the elements specified in the input with new elements. In a first example, referred to as a "remix" example, the input may be an existing track in multitrack format 1774, i.e. an existing song recording (such as final master 1770) formatted such that each instrumental track is segregated from the others (as opposed to a track in stereo format, in which the individual instrumental tracks are combined together into a left channel and a right channel). In a second example described below, referred to as a "new track" example, a library of stems (i.e. instrumental tracks or temporal sub-segments of instrumental tracks) is used as raw material to assemble an adaptation of an existing score.

In the remix example, the adaptation process 2200 receives the existing track in multitrack format 1774 as input, breaks the existing track 1774 into its constituent stems, and swaps in different stems in order to adapt the song of the existing track 1774 to satisfy specific affective response criteria specified by MIR data received as input (shown here as the MIR data 1783 required by the adaptation process). The required MIR data 1783 may be extracted from the MIR blueprint 1730 by a MIR data extraction process 1782. In some embodiments, as in each other MIR data extraction process 1756, 1740, the MIR data extraction process 1782 may be omitted and the required MIR data 1783 may simply be the entirety of the MIR blueprint 1730.

The database of music theory rules 2020 described previously is used by an adaptive music agent training process 1772 to train an adaptive music agent 2202 of the adaptation process 2200, as described in greater detail below with reference to FIGS. 22A-B.

The adaptation process 2200 draws on a library of audio stems 1776 and a database of instrument timbre profiles 1778 to identify and select stems to swap in to replace the original stems of the existing track 1774. Once stems have been swapped in to adapt the existing track 1774 to satisfy the MIR features of the required MIR data 1783, the adaptation process 2200 outputs the new mix as adapted rough mix 1780, and/or outputs a mix template 1786 instructing an artist or producer how to manually adapt the existing track 1774 to achieve the specified MIR features, including an indication of the desired or required MIR features 1783 themselves.

A user 1702 then interacts with the music production process 1758 to generate an adapted final mix 1790. As with the music composition process 1748, the user 1702 may interact with the music production process 1758 through a user interface 1642 such as a digital audio workstation (DAW) or other audio workstation. The user 1702 may be assisted by the mix template 1786 and/or may begin the interaction with the adapted rough mix 1780 as an input.

In some examples, the adaptation process 2200 may be used mid-production: i.e., the user 1702 may interact with the music production process 1758 to cause the adaptation process 2200 to perform one or more iterations of the adaptation process on a human-composed song that has reached the adaptation stage.

Figure 22A:
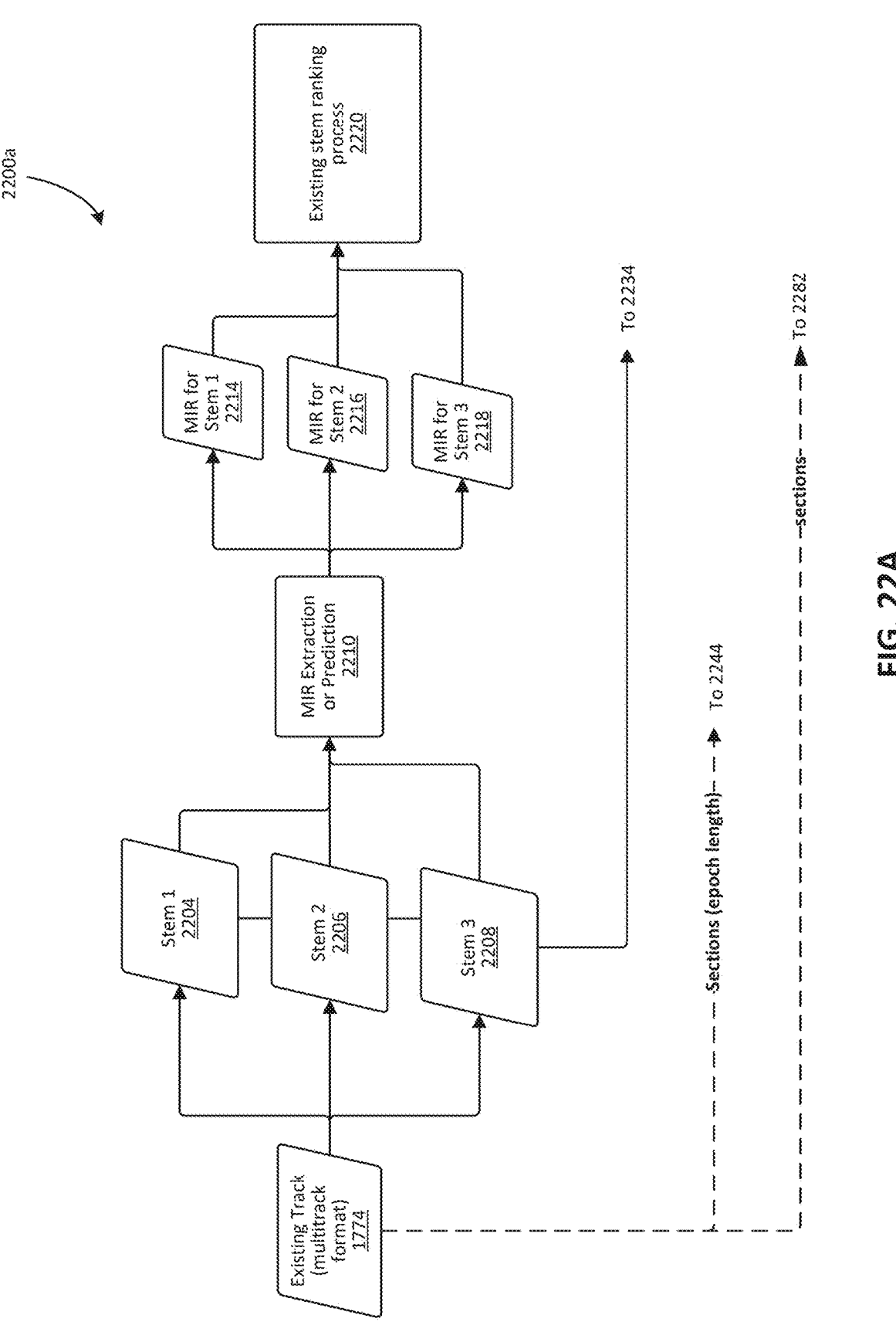
FIG. 22A is a block diagram showing a first portion of an adaptive music agent used by the affective music composition system of FIG. 16.

FIG. 22A is a block diagram showing a first portion 2200a of the adaptation process 2200. The adaptation process 2200 may be used to generate either a music track (referred to as a "track" example) or a MIR template to guide a user or another system in generating a track (referred to as a "template" example). In either of these examples, the track or template being generated may be a remix of an existing track (called a "remix" example) or a wholly new track (called a "new track" example). In a "remix" example, the adaptation process 2200 begins with an existing track 1774 being split into its constituent stems (shown as stem 1 2204, stem 2 2206, and stem 3 2208). These constituent stems 2204, 2206, 2208 have their MIR data extracted or predicted by a MIR extraction or prediction process 2210 using MIR extraction or prediction techniques described above, thereby generating a corresponding set of MIR data for each stem: MIR for stem 1 2214, MIR for stem 2 2216, and MIR for stem 3 2218. The MIR data for each stem of the existing track is then ranked by an existing stem ranking process 2220, which is described below with reference to second portion 2200b. The constituent stems from the existing track 1774 may also be added to the library of audio stems 1776 (not shown).

Figure 22B:
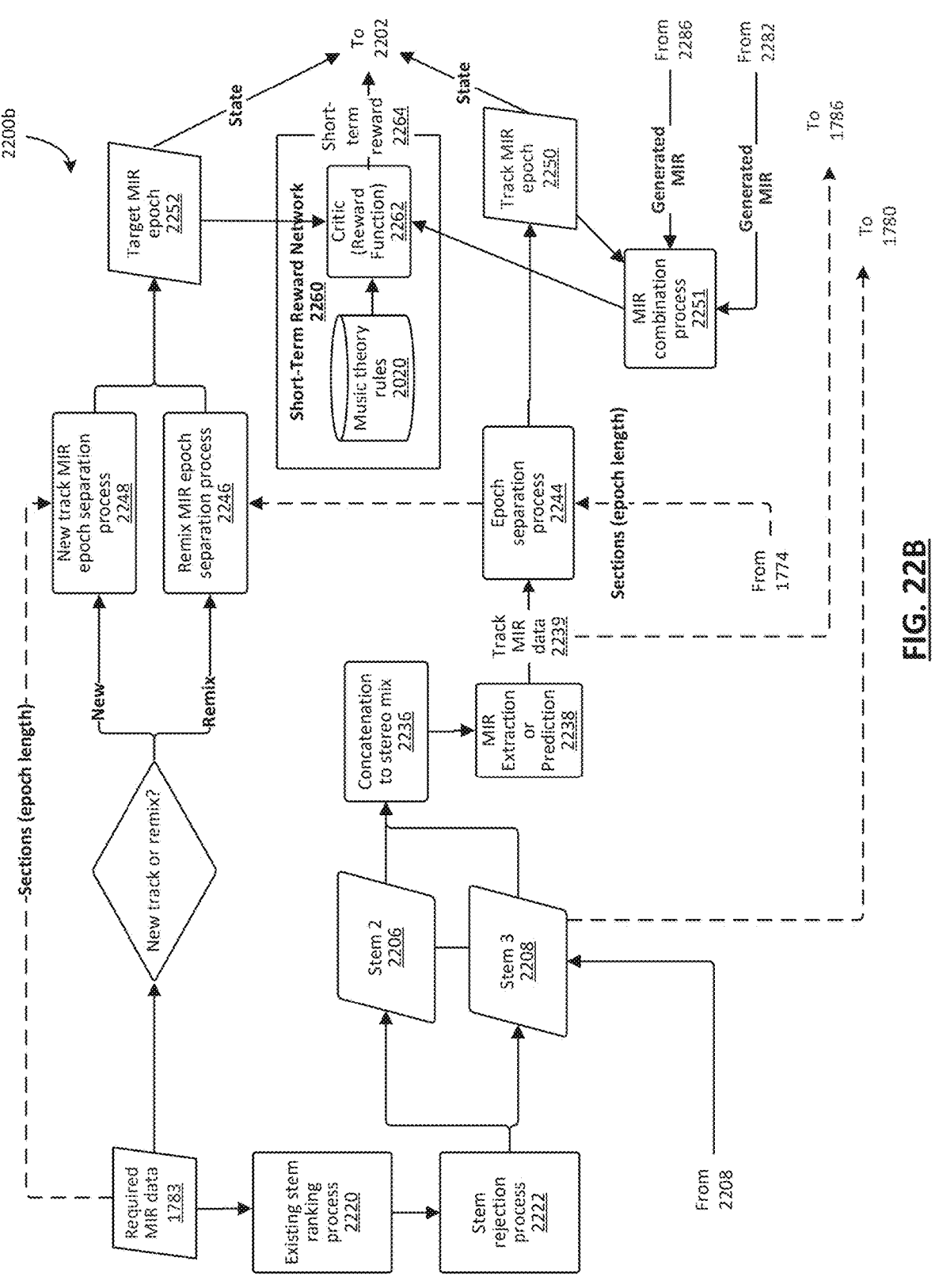
FIG. 22B is a block diagram showing a second portion of an adaptive music agent used by the affective music composition system of FIG. 16.

FIG. 22B is a block diagram showing a second portion 2200b of the adaptation process 2200. The existing stem ranking process 2220 uses the MIR data for each stem 2214, 2216, 2218 to identify which stems of the existing track 1774 are a close match to the required MIR data 1783 and ranks the stems 2204, 2206, 2208 on their similarity to the required MIR data 1783. The ranking process may use a k-nearest neighbors vector similarity calculation, as described by Madison Schott, "K-Nearest Neighbors (KNN) Algorithm for Machine Learning", at https://medium.com/capital-one-tech/k-nearest-neighbors-knn-algorithm-for-machine-learning-e883219c8f26, which is hereby incorporated by reference in its entirety. A stem rejection process 2222 determines which stems to reject based on the rankings generated by the existing stem ranking process 2220 and a set of music theory rules. The stem rejection process 2222 can be performed algorithmically in some embodiments (for example, by using a database of music theory rules 2020 (not shown)), whereas in other embodiments it may be performed by a human producer. The use of music theory rules is important to the stem rejection process 2222, as it may make sense to keep some stems that are fundamental to the song's structure even if they conflict with the MIR blueprint 1730 (or the required MIR data 1783).

The stems of the existing track 1774 that are not rejected (shown here as stem 2 2206 and stem 3 2208) are fed forward to a concatenation process 2236 which concatenates the retained stems (i.e. the stems that were not rejected) into a stereo mix. They are also fed forward for concatenation into a rough mix 1780 of the final remixed track in a "track" example, as described below with reference to the third portion 2200c. A further MIR extraction or prediction process 2238 is used to extract or predict the MIR features of the stereo mix generated by the concatenation process 2236, as described previously, thereby generating track MIR data 2239. The track MIR data 2239 extracted from the retained stems is fed forward for concatenation into a mix template 1786 of the final remixed track in a "template" example, as described below with reference to the third portion 2200c. An epoch separation process 2244 performs a separation of the track MIR data 2239 into track MIR epochs 2250, with the duration of each epoch defined by the durations of sections (as defined by rules such as music theory rules) of the original track 1774.

The required MIR data 1783, in addition to providing an input to the existing stem ranking process 2220, may be used to generate MIR epochs for either a remix of an existing track 1774 or a new track adapting a score using a library of stems. In the remix example, the required MIR data 1783 is broken into epochs based on sections of the track being remixed (i.e. epochs of the existing track 1774): the required MIR data 1783 is separated into epochs by a remix MIR separation process 2246, with the duration of each epoch defined by the durations of the sections of the original track 1774. In the "new track" example, the required MIR data 1783 is broken into epochs having durations based on sections of the MIR blueprint 1730 (or the required MIR data 1783) instead of sections of the existing track 1774 (as there is no existing track 1774 in this example), by a new track MIR separation process 2248.

The next stage proceeds one epoch at a time. Each track MIR epoch 2250 and each corresponding target MIR epoch 2252 is provided, one epoch at a time, as state data to an adaptive music agent 2202, described below in reference to the third portion 2200c. A short-term reward network 2260, similar to the short-term reward network 2120 of FIG. 21A, uses a critic 2262 to apply a reward function to three inputs: the output of a MIR combination process 2251 (described below) from the previous epoch, the target MIR epoch 2252 from the previous epoch, and music theory rules from the database of music theory rules 2020. The reward function of the critic 2262 generates a short-term reward 2264 based on how closely the music theory rules 2020 are obeyed and the extent to which the target MIR epoch 2252 is matched by the track MIR epoch 2250. The short-term reward 2264 generated as input in generating epoch n is thus based on the MIR combination process 2251 and target MIR epoch 2252 of epoch (n−1).

Figure 22C:
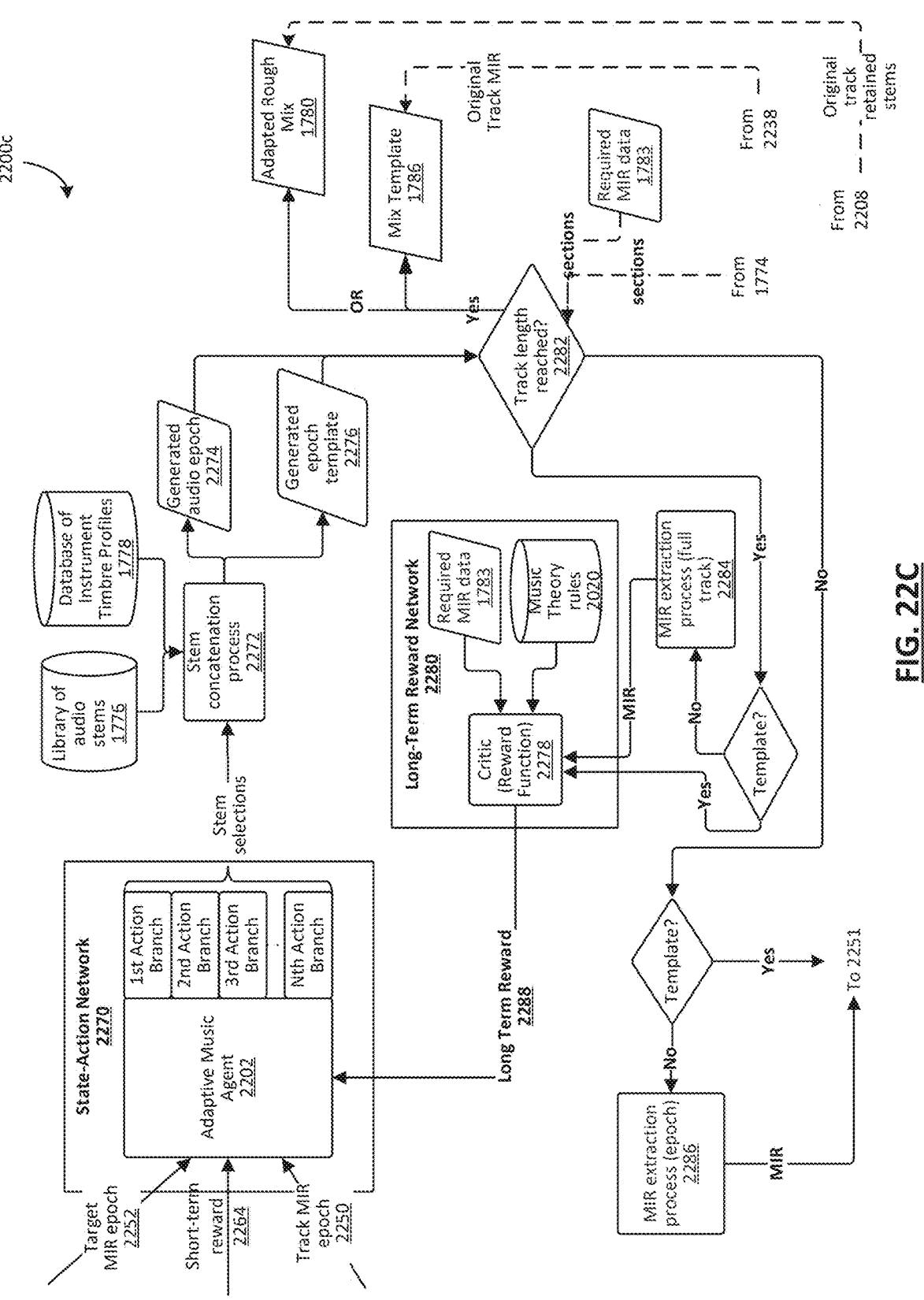
FIG. 22C is a block diagram showing a third portion of an adaptive music agent used by the affective music composition system of FIG. 16.

FIG. 22C is a block diagram showing a third portion 2200c of the adaptation process 2200. A state-action network 2270 comprises an adaptive music agent 2202 configured to select, in response to each epoch of input data (i.e.

each track MIR epoch 2250, each corresponding target MIR epoch 2252, and each corresponding short-term reward 2264), a stem for each of a plurality of action branches (shown as $1^{st}$ action branch, $2^{nd}$ action branch, $3^{rd}$ action branch, and so on through Nth action branch wherein N may be any positive integer). Each action branch corresponds to a layer in the mix: i.e., typically an instrument layer such as drums, bass, guitar, etc. Branches can be omitted if the corresponding instrument already exists in the stems remaining from the existing track 1774 and no additional layers are desired. The stem for each action branch is selected from the available stems provided by the library of audio stems 1776.

In some embodiments, the adaptive music agent 2202 may be implemented as a deep recurrent branching Q-Learning Network with LSTM for memory of actions taken (i.e. stems selected) for all epochs so far. The LSTM records the MIR features of tracks from one or more previous time steps (e.g. epochs), denoted herein as n time steps, namely the n previous target MIR epochs 2252 and n previous track MIR epochs 2250, and providing a state vector of these previous MIR features to a policy of the adaptive music agent 2202. A Planner of the adaptive music agent 2202 receives this state vector and the short-term reward 2264, along with the previous adaptation action taken (i.e. stems selected for each branch, as described below), and the planner updates the policy accordingly. The planner is trained using data from previous adaptation sessions. The adaptive music agent 2202 is trained using reinforcement learning, wherein the library of audio stems 1776 defines the action space, and the short-term reward 2264 and long-term reward 2288 (described below) provide reward feedback. A time step of the adaptive music agent 2202 may correspond to an epoch, such a 4 bars of music. The adaptive music agent 2202, like the MIR generator GAN 1612, the score generator GAN 1616, and mastering agent 2102, uses an actor-critic behaviour for reinforcement learning and deep learning in the described embodiment. In other embodiments, the adaptive music agent 2202 may be implemented using other models, such as a model-based actor critic model, an A3C model, or any other suitable machine learning model.

In a "track" example, a stem concatenation process 2272 concatenates the selected stems, provided by the library of audio stems 1776, to generate a generated audio epoch 2274 (i.e. a mix of stems for the current epoch) consisting of the new stems selected by the adaptive music agent 2202 to be layered over the retained stems of the existing track (in a "remix" example) or the new stems selected to make up the entirety of the song (in a "new track" example). Alternatively, in a "template" example, the stem concatenation process 2272 uses the database of instrument timbre profiles 1778, which includes MIR data associated with different instrument choices for creating a new track or remix template, to generate a MIR profile to create a generated epoch template 2276 for that generated epoch. The generated epoch template 2276 includes MIR data for the epoch.

Once the generated audio epoch 2274 or generated epoch template 2276 has been generated, the length of the generated audio or template is compared at step 2282 to the total desired length of the track or template (based on the sections of the existing track 1774 and/or the required MIR data 1783). If the desired length has been reached, the generated epoch templates 2276 are combined with each other and with the MIR data of the retained stems of the original track (shown as Track MIR data 2239 in second portion 2200*b*) to generate a mix template 1786, or the generated audio epochs 2274 are combined with each other and with the retained stems of the original track (shown as Stem 2 2206 and Stem 3 2208 in second portion 2200*b*) to generate an adapted rough mix 1780. The mix template 1786 or adapted rough mix 1780 is also provided to a long-term reward network 2280 (described below) to train the adaptive music agent 2202. If the adapted rough mix 1780 is provided, it first has its MIR data extracted, predicted, or looked up by a MIR extraction process 2284. As described above, the MIR data can either be extracted via a tool like MIRtoolbox, referenced (i.e. looked up) from a table of previously extracted MIR features, or predicted using a model that inputs raw audio and outputs a MIR prediction. The extracted (or predicted, or looked up) MIR data is then provided to the long-term reward network 2280. The adaptation process then ends. In some embodiments, while the current track or template is being generated, the entire track or template generated thus far (both original and generated stems) may be provided to the long-term reward network 2280 to train the adaptive music agent 2202 before the adaptation process is finished.

If, at step 2282, the total desired length of the track or template has not been reached, the current generated audio epoch 2274 or generated epoch template 2276 is provided as feedback to the MIR combination process 2251. In the "track" example, the current generated audio epoch 2274 is first passed through a MIR extraction process 2286 to extract, predict, or look up the MIR data for the current generated audio epoch 2274, as described above, to generate MIR data corresponding to the current generated audio epoch 2274. In a "remix" example, the MIR combination process 2251 combines the MIR extracted from the retained stems of the original track (i.e. Track MIR data 2239) with the feedback MIR data (from the MIR extraction process 2286 or the generated epoch template 2276) to generate combined MIR data for the epoch, including both retained stems and new stems. This combined MIR data is provided to the critic 2262 to generate the short term reward 2264 for the subsequent epoch: thus, the combined MIR data for epoch (n−1) is provided to the critic 2262, along with the target MIR epoch 2252 for epoch (n−1), to generate the short term reward 2264 used by the adaptive agent 2202 in selecting stems for epoch (n). It will be appreciated that, in a "new track" example, there are no retained stems, as there is no original track being remixed. Thus, the output of the MIR combination process 2251 is simply the feedback MIR data received from the MIR extraction process 2286 or the generated epoch template 2276.

The long-term reward network 2280 comprises a critic 2278 that applies a reward function to three inputs: the required MIR data 1783, music theory rules from the database of music theory rules 2020, and either the MIR data extracted from the adapted rough mix 1780 by MIR extraction block 2284, or the mix template 1786. The reward function generates a long-term reward 2288 based on the music theory rules and the required MIR data 1783 applied to the MIR data of the whole adapted track (or the whole template).

The affective music recommendation system 100 and/or affective music composition system 1600, and/or aspects and components thereof, may be recombined in various configurations to address specific use cases relating to the selection or creation of music to induce specific affective responses in one or more listeners. These use cases may involve therapeutic, entertainment, or lifestyle applications. Several example use cases of the example embodiments described herein will now be described with reference to FIGS. 27-30.

Figure 27:
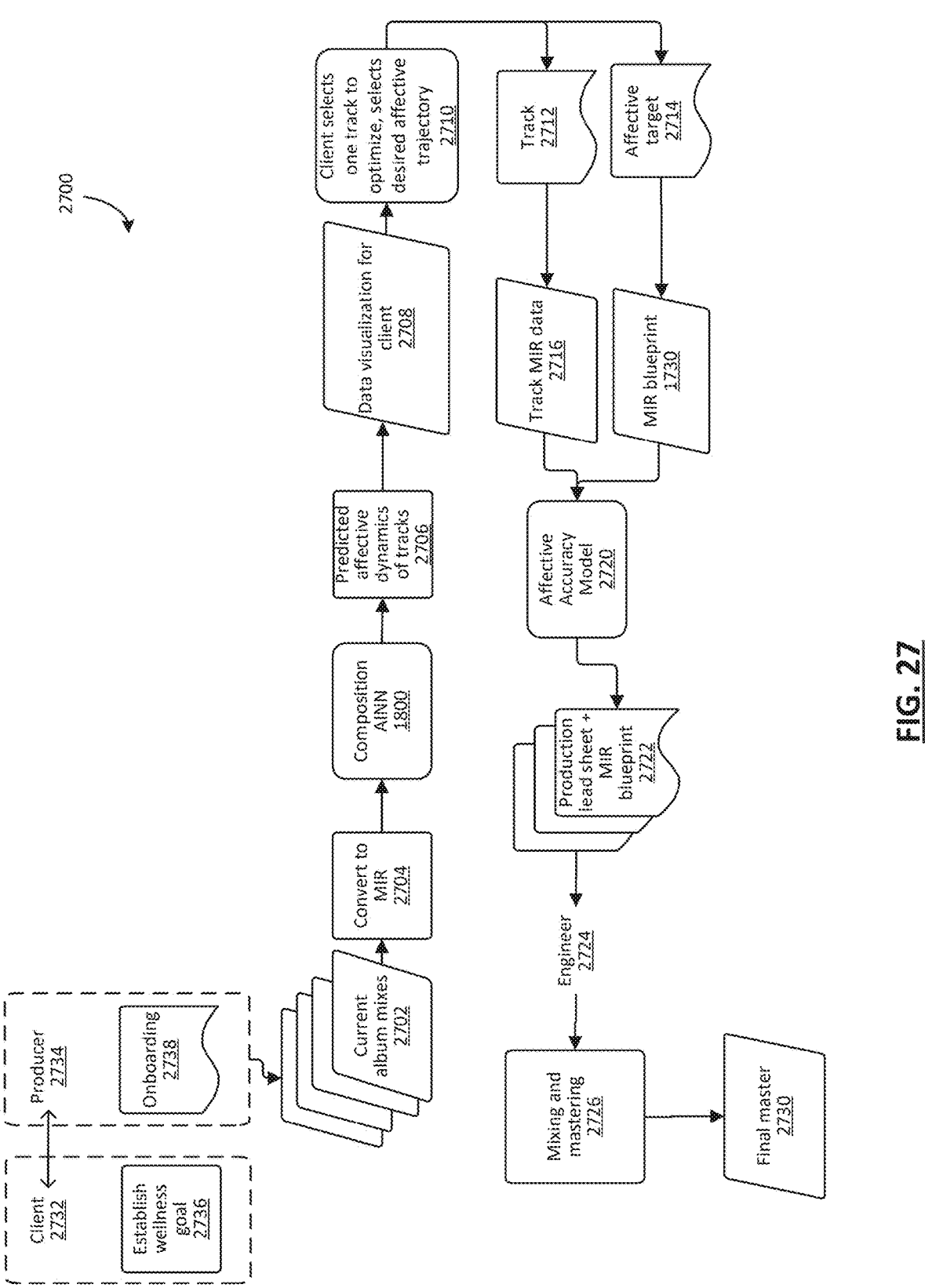
FIG. 27 is a block diagram of an example album remixing use case using embodiments described herein.

FIG. 27 shows an example album remixing use case 2700 using embodiments described herein. A client 2732, who is an artist with an existing album of songs, works with a producer 2734 to establish a set of wellness goals 2736 for the songs of the album with the assistance of an onboarding document 2738 that explains the affective composition process and emotional framework (e.g. the GEMS/Russel Circumplex Model of affect). The producer 2734 receives the current album mixes 2702 (i.e. the mixes of the songs on the album) form the client 2732 and provides them to a MIR extraction process 2704 to convert them to MIR data. A trained affective inference model, such as composition AINN 1800, is used to generate predicted affective dynamics of the tracks 2706. The predicted affective dynamics 2706 are transformed into a visualization 2708 of the songs' emotional dynamics. The client 2732 reviews the visualization 2708 and selects a first track to optimize along with a desired affective trajectory to be induced by the selected track at step 2710, thereby providing track 2712 and the affective target 2714 (e.g. the desired affective trajectory) as inputs to the subsequent processes of the use case 2700. The track MIR data 2716 of the track 2712 is provided as a first input to an affective accuracy model 2720 (such as MIR generation process 1900). A MIR blueprint 1730 corresponding to the affective target 2714 is used as the second input to the affective accuracy model 2720. The affective accuracy model 2720 is used to generate a production lead sheet (such as production lead sheet 2600 produced by the affective music composition system 1600) and MIR blueprint identifying MIR features that need to be changed, shown jointly as documents 2722, which are used by an engineer 2724 to perform mixing and mastering processes (such as via the music production process 1758 of the affective music composition system 1600) to generate a final master 2730 of the selected track that is configured to achieve the desired affective target. In this example, mastering techniques are applied to the track's segments (e.g. modifying the timbre of the piano), ambience tracks are added to the mix to better meet the MIR targets, and binaural entrainment (2 Hz) is added to the track.

Figure 28:
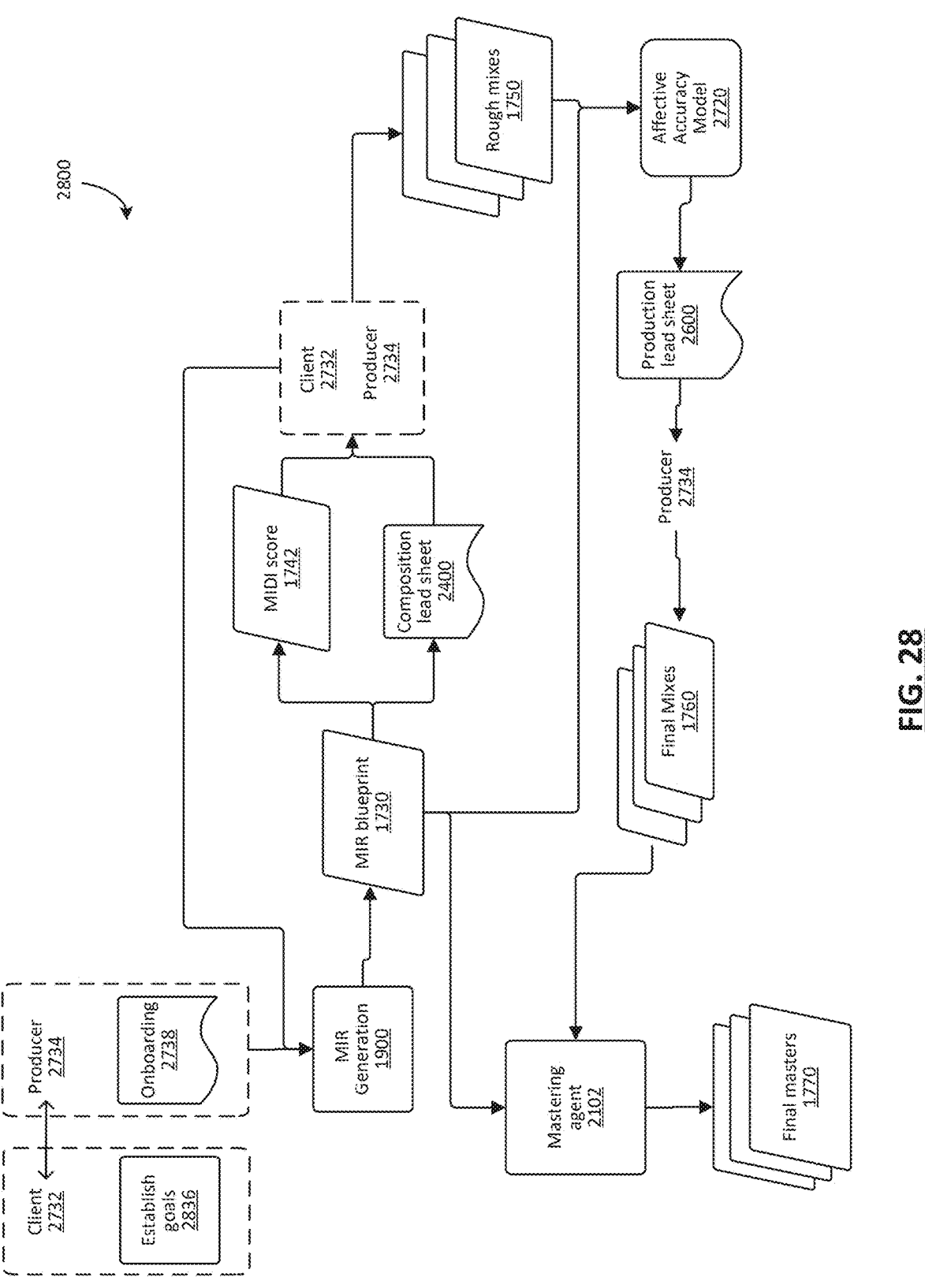
FIG. 28 is a block diagram of an example music remixing use case to target wellness playlists using embodiments described herein.

FIG. 28 shows an example music composition use case 2800 to target wellness playlists using embodiments described herein. The same onboarding process is used as in use case 2700, but in this example the goal establishment step 2836 includes picking playlists (e.g., playlists of an existing online music service) to target and strategize wellness goal for the client's 2732 album, an emotional trajectory of the tracks is selected, and the track lengths and the number of tracks needed are identified. For example, a nostalgic track and a peacefulness track are selected to target a "chill" playlist, two "focus" tracks and one melancholy track are selected to target a "sad beats" playlist, all of which are 3 minutes+/−20 seconds in duration.

Composition of each selected track begins by using the MIR generation process 1900 of the composition system 1600 to generate a MIR blueprint 1730 for the track. A score (e.g. MIDI score 1742) and a composition lead sheet 2400 are generated (e.g., using composition system 1600), and the producer 2734 and client 2732 may refine the score 1742 and composition lead sheet 2400 over one or more additional iterations of the process by changing various parameters in accordance with the MIR blueprint 1730. For example, the MIDI score 1742 may be adjusted to provide track-level chord progressions and melodies in line with the goals 2836.

The producer 2734 and client 2732 work together to generate rough mixes 1750 of the various tracks. An affective accuracy model 2720 uses the rough mixes 1750 and MIR blueprint 1730 to generate a dataset of musical features needed to change and create a production lead sheet 2600. The producer 2734 then applies mixing techniques (e.g., using the music production process 1758) to the tracks to better meet the MIR targets set out by the production lead sheet to generate a set of final mixes 1760. The mastering agent 2102 may then be used to perform automated mastering of the final mixes 1760 to generate the final masters 1770.

Figure 29:
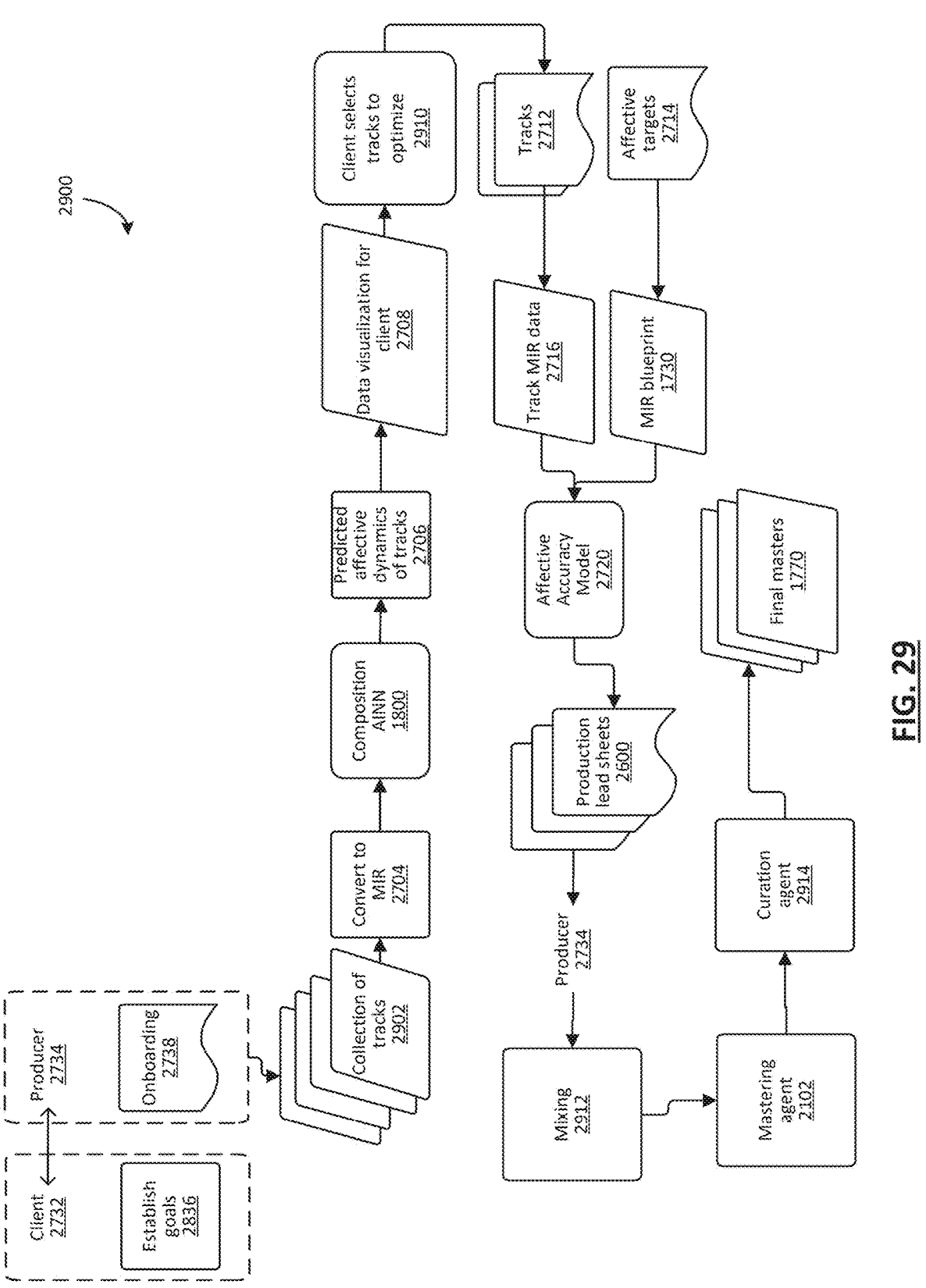
FIG. 29 is a block diagram of an example music collection remixing use case to generate multiple albums with distinct affective targets using embodiments described herein.

FIG. 29 shows an example music collection adaptation use case 2900 to generate multiple albums with distinct affective targets using embodiments described herein. The client 2732 is an artist with a collection of existing songs, and who wants to release the songs as three albums, each album having a specific set of affective targets. The artist 2732 works with the producer 2734 to set the goals 2836 as in use case 2800. The collection of tracks 2902 is received from the client 2732 and provided to the MIR extraction process as in use case 2700. The use case 2900 proceeds as use case 2700 for each track, but the client 2732 selects multiple tracks 2712 to optimize at step 2910, generally by selecting tracks that are close to the desired affective goals.

The affective targets 2714 chosen by the client 2732 during onboarding 2836 are used to generate a MIR blueprint 1730 for each track. The track MIR data 2716 for each track 2712 is provided to the affective accuracy model 2720 along with the MIR blueprint 1730 for each track to generate a production lead sheet 2600 for each track identifying musical features that need to change. The producer 2734 uses the production lead sheets 2600 to perform mixing 2912, the output of which (e.g. rough mixed 1760) is provided to the mastering agent 2102, the output of which is curated by a curation agent 2914 to generate the final masters 1770. The curation agent 2914 may be a Deep Q Network from the affective music recommendation system 100 that has been trained with the composition AINN 1800.

Figure 30:
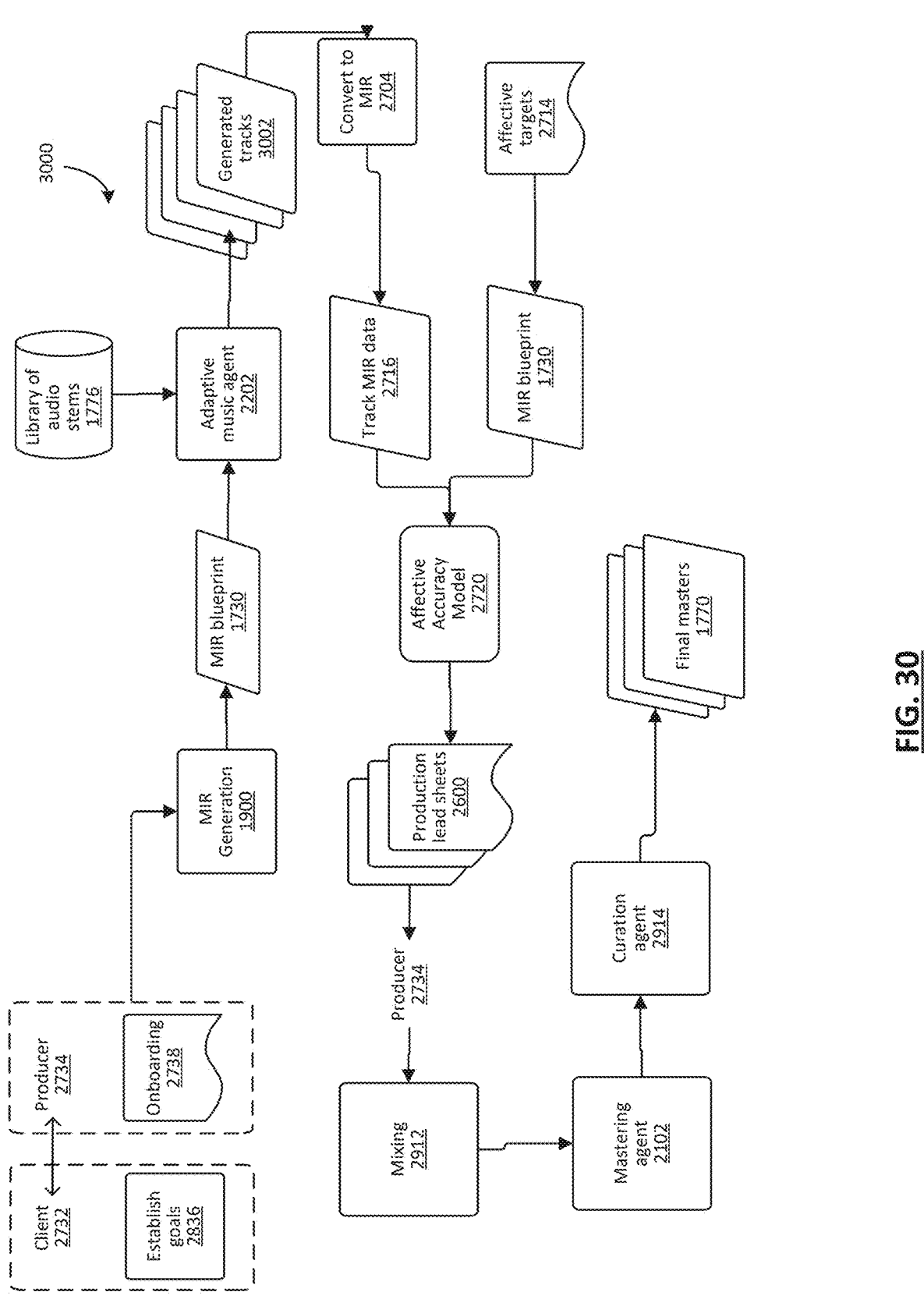
FIG. 30 is a block diagram of an example music adaptation use case to generate affective music using a library of existing stems using embodiments described herein.

FIG. 30 shows an example music adaptation use case 3000 to generate affective music using a library of existing stems using embodiments described herein. The client 2732 provides a library of unused stems 1776 to be used to generate new songs for the albums. The MIR generation process 1900 is used to generate MIR blueprints 1730 based on the affective targets 2714. The adaptive music agent 2202 draws on the library of stems 1776 to generate generated tracks 3002 intended to match the MIR blueprints 1730. At this stage, the tracks 3002 may be shared with the client 2732 for approval and to give the opportunity to add additional elements. The tracks 3002 are then converted to MIR data at 2704 to generate track MIR data 2716. The MIR blueprints 1730 and track MIR data 2716 are used by the affective accuracy model 2720 to generate production lead sheets 2600 for the tracks. The producer 2734 performs mixing 2912, followed by using the mastering agent 2102 and curation agent 2914 to generate the final masters 1770.

In some embodiments, the described systems and methods may use non-auditory stimuli and non-audio data instead of or in addition to the audio data and auditory stimuli described above. Tactile or visual data could be used in some embodiments to collect and predict user affective responses to tactile or visual stimuli using techniques analogous to those above.

In some embodiments, the audio segments may comprise monaural or binaural beat data, either by themselves or integrated with other auditory data. Monaural and binaural beats have been shown to have the capacity to induce specific affective responses in humans under some conditions. See, e.g. the comparative literature study by Chaieb et al., "Auditory Beat Stimulation and its Effects on Cognition and Mood States", *Frontiers in Psychiatry*, Vol. 6, 2015, https://www.frontiersin.org/article/10.3389/fp-syt.2015.00070, which is hereby incorporated by reference in its entirety.

Although the present disclosure may be described, at least in part, in terms of methods and devices, a person of ordinary skill in the art will understand that the present disclosure is also directed to the various components for performing at least some of the aspects and features of the described methods, be it by way of hardware components, software or any combination of the two. Accordingly, the technical solution of the present disclosure may be embodied in the form of a software product. A suitable software product may be stored in a pre-recorded storage device or other similar non-volatile or non-transitory computer- or processor-readable medium, including DVDs, CD-ROMs, USB flash disk, a removable hard disk, or other storage media, for example. The software product includes instructions tangibly stored thereon that enable a processing device (e.g., a personal computer, a server, or a network device) to execute examples of the methods or systems disclosed herein.

The skilled person will also appreciate that the output of the methods and devices described above, namely the audio stream 234 including the audio segments 230 themselves, may be stored as music data (such as an audio file) on a storage medium such as non-volatile or non-transitory computer- or processor-readable medium, including DVDs, CD-ROMs, USB flash disk, a removable hard disk, or other storage media. The music may also be stored on other digital or analog storage media appropriate for use in audio applications or audio playback or broadcast devices, such as cassette tapes, vinyl records, or any other storage medium for digital or analog music data. In one embodiment, an audio stream may be identified as being likely to induce a specific affective trajectory, either user-specifically or user-independently, and this audio stream may be stored for later listening by a user.

In the described methods or block diagrams, the boxes may represent events, steps, functions, processes, modules, messages, and/or state-based operations, etc. While some of the above examples have been described as occurring in a particular order, it will be appreciated by persons skilled in the art that some of the steps or processes may be performed in a different order provided that the result of the changed order of any given step will not prevent or impair the occurrence of subsequent steps. Furthermore, some of the messages or steps described above may be removed or combined in other embodiments, and some of the messages or steps described above may be separated into a number of sub-messages or sub-steps in other embodiments. Even further, some or all of the steps may be repeated, as necessary. Elements described as methods or steps similarly apply to systems or subcomponents, and vice-versa. Reference to such words as "sending" or "receiving" could be interchanged depending on the perspective of the particular device.

The above-described embodiments are considered to be illustrative and not restrictive. Example embodiments described as methods would similarly apply to systems, and vice-versa.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

The invention claimed is:

1. A processor-executed method for generating an audio stream for inducing an affective state change in a listener, comprising:
identifying a current affective state of the listener;
identifying a target affective state of the listener;
identifying an affective trajectory from the current affective state to the target affective state;
using a trained segment identification machine learning model to identify a first audio segment likely to induce in the listener a desired affective response corresponding to at least an initial portion of the affective trajectory when the first audio segment is presented to the listener as an auditory stimulus;
using a trained affect inference machine learning model to infer an inferred new affective state based on the current affective state and a set of audio feature values of the first audio segment;
identifying an updated affective trajectory from the inferred new affective state to the target affective state;
using the trained segment identification machine learning model to identify a subsequent audio segment likely to induce in the listener a subsequent desired affective response corresponding to at least an initial portion of the updated affective trajectory when the subsequent audio segment is presented to the listener as an auditory stimulus;
generating the audio stream based at least in part on the first audio segment and the subsequent audio segment;
sending audio stream data based on the audio stream to a listener device; and
causing the audio stream to be presented to the listener via at least one speaker of the listener device.

2. The method of claim 1, wherein:
the trained affect inference machine learning model is trained using training data comprising:
training audio feature data corresponding to a plurality of training audio segments, and
affective state data gathered from one or more human subjects in association with exposure of each human subject to each of a plurality of audio stimuli corresponding to the plurality of training audio segments.

3. The method of claim 2, wherein:
the one or more human subjects comprises the listener.

4. The method of claim 3, further comprising, after sending the audio stream data to the listener device:
receiving updated current affective state data from the listener; and
training the trained affect inference machine learning model using runtime training data comprising:

audio feature data corresponding to each of the first audio segment and the subsequent audio segment; and the updated current affective state data.

5. The method of claim 4, wherein:

the audio feature data comprises music information retrieval (MIR) data.

6. The method of claim 2, wherein:

the trained segment identification machine learning model comprises a reinforcement learning model.

7. The method of claim 2, wherein:

the trained segment identification machine learning model comprises a deep learning neural network.

8. The method of claim 2, wherein:

the training audio feature data comprises music information retrieval (MIR) data.

9. The method of claim 1, wherein:

identifying the listener's target affective state comprises:

receiving target affective state data from the listener via the listener device; and identifying the listener's target affective state based on the target affective state data.

10. A non-transitory processor-readable medium containing instructions for executing the method of claim 1.

11. A non-transitory storage medium containing the audio stream generated by the method of claim 1.

12. The method of claim 1, wherein:

the trained segment identification machine learning model is trained using reward data received from the trained affect inference machine learning model; and the trained affect inference machine learning model generates the reward data by:

inferring an inferred affective response of the listener to a set of audio feature values of the audio stream; and generating the reward data based on a comparison of the inferred affective response to the desired affective response.

13. The method of claim 1, wherein:

the audio stream data comprises recommendation data recommending the audio stream.

14. The method of claim 1, wherein:

the audio stream data comprises the audio stream.

15. The method of claim 1, wherein:

identifying the listener's current affective state comprises:

receiving affective self-evaluation data from the listener via the listener device; and identifying the listener's current affective state based on the affective self-evaluation data.

16. The method of claim 1, wherein:

identifying the listener's current affective state comprises:

receiving physiological data correlated with one or more physiological states of the listener; and identifying the listener's current affective state based on the physiological data.

17. A system comprising:

a processor system; and a memory system having stored thereon instructions executable by the processor system to cause the system to perform the method of claim 1.

18. The method of claim 1, wherein:

the set of audio feature values of the first audio segment comprises music information retrieval (MIR) data.

\* \* \* \* \*